(12) United States Patent
Monassevitch et al.

(10) Patent No.: US 7,892,244 B2
(45) Date of Patent: Feb. 22, 2011

(54) SURGICAL COMPRESSION CLIPS

(75) Inventors: Leonid Monassevitch, Hadera (IL);
Boaz Shenhav, Tel Aviv (IL); Boaz Harari, Tel Aviv (IL); Amir Perle, Haifa (IL); Michael Arad, Tel Aviv (IL); Shahar Millis, Pardes Hanna (IL); Kobby Greenberg, Even Yehuda (IL); Alex Geller, Kfar Saba (IL); Amir Szold, Tel Aviv (IL); Shlomo Lelcuk, Savion (IL); Doron Kopelman, Caesarea (IL); Amol Bapaye, Pune (IN); Dror Rosner, Holon (IL)

(73) Assignee: Niti Surgical Solutions Ltd., Netanya (IL)

( * ) Notice: Subject to any disclaimer, the term of this patent is extended or adjusted under 35 U.S.C. 154(b) by 1089 days.

(21) Appl. No.: 11/647,913

(22) Filed: Dec. 29, 2006

(65) Prior Publication Data
US 2007/0213747 A1 Sep. 13, 2007

Related U.S. Application Data

(60) Provisional application No. 60/780,446, filed on Mar. 9, 2006.

(51) Int. Cl.
*A61B 17/08* (2006.01)
(52) U.S. Cl. .................................. 606/151; 606/157
(58) Field of Classification Search .................. 606/151, 606/157, 158; 289/277, 278
See application file for complete search history.

(56) References Cited

U.S. PATENT DOCUMENTS

| | | | |
|---|---|---|---|
| 5,002,562 A | 3/1991 | Oberlander | |
| 5,062,846 A | 11/1991 | Oh et al. | |
| 6,352,503 B1 | 3/2002 | Matsui et al. | |
| 6,428,548 B1 | 8/2002 | Durgin et al. | |
| 6,849,078 B2 | 2/2005 | Durgin et al. | |
| 2001/0025181 A1 | 9/2001 | Freedlan | |
| 2002/0072759 A1 | 6/2002 | Fry | |
| 2003/0093091 A1 | 5/2003 | Paolitto et al. | |
| 2005/0096548 A1 | 5/2005 | Talish et al. | |
| 2005/0165429 A1 | 7/2005 | Douglas et al. | |
| 2007/0060951 A1 | 3/2007 | Shannon | |

FOREIGN PATENT DOCUMENTS

| | | |
|---|---|---|
| DE | 20316925 U1 | 8/2004 |
| WO | 2004080314 A1 | 9/2004 |

*Primary Examiner*—Julian W Woo
(74) *Attorney, Agent, or Firm*—Pearne & Gordon LLP

(57) ABSTRACT

A surgical clip assembly which includes a pair of generally linear compression elements for securing tissue between them and for applying to the secured tissue a compression force. The clip assembly has an initial, open position in which the linear compression elements may be positioned about tissue to be secured between them. The assembly also has a final, closed position where the compression elements are substantially parallel to each other, applying a compressive force to the secured tissue. The clip assembly also includes a force means disposed between the pair of compression elements and operative to transmit operational forces between them.

20 Claims, 54 Drawing Sheets

SURGICAL COMPRESSION CLIPS

CROSS REFERENCE TO RELATED APPLICATION

This application claims the benefit of U.S. Provisional Application No. 60/780,446, filed Mar. 9, 2006.

FIELD OF THE INVENTION

The present invention relates to the field of surgical compression clips generally, and, in particular, to the field of surgical compression clips, at least partially formed from shape memory material.

BACKGROUND OF THE INVENTION

Several methods are known in the art for joining tissue portions at the site of organ resections, particularly gastrointestinal (GI) tract resections, or at the site of other types of tissue perforations or tissue openings. These include threads for manual suturing, staplers for mechanical suturing, tissue adhesives and compression rings and clips.

While manual suturing is universally known and relatively inexpensive, the degree of success depends considerably on the skill of the surgeon. Another disadvantage of this technique is that post-operative complications are common. Further, suturing an organ results in lack of smoothness of the tissue therein, which, when the sutured organ is part of the gastrointestinal tract, hampers peristalsis in the sutured area. Finally, suturing is both labor and time consuming.

Increasingly, stapling is being used for suturing. Staplers for mechanical suturing ensure a reliable joining of tissue and reduce the time needed for surgery compared with manual suturing. However, after healing, metal staples remain in place along the perimeter of the suture, which reduces elasticity of the junction and adversely affects peristalsis when the sutured organ is part of the gastrointestinal tract. These complications often lead to strictures and inflammatory reactions to the foreign bodies left behind. Staples also often lead to undesired leakage of blood and other body liquids into the region of resected tissue further resulting in severe infection. Additionally, stapling mechanisms generally are relatively large and fairly rigid, limiting the maneuverability of an endoscope used in conjunction with the stapling mechanism. This lack of maneuverability restricts an endoscopic approach to many locations within the body.

Junctions using compression devices, such as rings (or loops) and clips, ensure the best seal and post-operative functioning of the organs. The compression force exerted by compression rings is applied only momentarily at the tissue junction and is reduced as the tissue is crushed. Clips made of memory alloys enable portions of tissue to be pressed together with increasing pressure as they are heated, due to the inherent properties of the alloys. Their design is cheap and they are small in size. Moreover, when used in the GI tract they are often self-evacuated.

A major disadvantage of known clips is that they permit compression of only approximately 80-85% of the junction perimeter, thus requiring additional manual sutures, which reduce the integrity of the seal of the junction during the healing period and its elasticity during the post-operative period. Furthermore, this additional suturing is problematic inasmuch as it has to be carried out across a joint which includes a portion of the clip, thereby rendering difficult the sealing and anastomosis of the organ portions.

The compressive force exerted by clips generally is not equal at both ends of the clip because of the clips' typically asymmetric construction. Similarly, compression does not act along a line between the two compressing portions holding the tissue to be compressed. This can lead to the clip disengaging from the closure site before closure is complete and scar tissue mature.

Typically, clips do not necessarily have a securing mechanism against slipping off the tissue. Clips as currently designed may also affect the maneuverability of an endoscope.

DEFINITIONS

"Proximal" relates to the side of a clip or device closest to the user, while "distal" refers to the side of a clip or device furthest from the user.

"Lesion" may be used in place of the word "polyp" "perforation", hemorrhoid, tissue adjacent to a resected site, or openings within tissue generated by any surgical procedures, without any intent at differentiating these different types of lesions, except where specifically indicated.

"Gastrointestinal tract" or its equivalents are used in the specifications and claims without intent of being limiting. Other organ systems, and lesions found therein, are also contemplated as being treatable with the compression clips and devices described in the present specification.

"Hinge spring" is one type of a "force applier" and this latter term may be used herein interchangeably with hinge spring without any intent at differentiating between these terms, except where specifically indicated. Accordingly, the latch described herein, as well as elements having other shapes, may also be considered to be force appliers if they are used for, and their operation is based on, their being formed from and possessing the force applying properties of shape memory materials. Hinge springs may be described herein as "hinge members", "force means" and "hinge members" again without any attempt at differentiating between these terms except where specifically indicated.

"Endoscope" as used herein should be construed as including all types of invasive instruments, flexible or rigid, having scope features. These include, but are not limited to, colonscopes, gastroscopes, laproscopes, and rectoscopes. Similarly, the use of "endoscopic" is to be construed as referring to all types of invasive scopes.

SUMMARY OF THE INVENTION

The present invention seeks to provide an improved surgical compression clip having force appliers/force means formed of a shape memory alloy material. These clips may be used for joining tissue at the resection site in resections of many kinds, as well as for closing various other types of organ perforations. They may be used inter alia in polypectomies, gastrectomies and gastroplastic procedures.

It is an object of the present invention to provide a surgical compression clip which exerts a constant compressive force irrespective of thickness of the compressed tissue, and irrespective of the changes it undergoes during the wound healing process. Such a clip reduces the chances of liquid leakage after resection while ensuring proper healing and closure of the resected site. Typically, but without intending to be limiting, no foreign body is left behind after tissue closure is complete.

It is a further object of the present invention to provide a clip that ensures protection against the clip being expelled before tissue closure is complete.

Another object of the present invention is to provide a non-unitary surgical clip which exerts a constant compressive force along the entire profile of the surfaces of the clip's clamping elements. The clip is made of shape memory material which provides a constant compressive force over large elongations.

In yet another object of the present invention a surgical compression clip is provided that produces continuous clamping compression of tissue adjacent to a resected site. The continuous compression is effected along a continuous line, thereby preventing undesired post-surgery fluid leakage and bleeding. Such a continuous line is impossible to attain when using surgical staples.

It is a further object of the present invention to provide a surgical compression clip and a system for applying the clip that reduces the risk of tissue perforation when all tissue layers proximate to a lesion are resected.

The surgical clips described herein may find particular use in various types of resections of a suspect lesion, such lesion arising in, for example, but without intending to be limiting, the bowel, rectum, appendix, gallbladder, uterus, stomach, esophagus, etc.

In one aspect of the present invention there is provided a surgical clip assembly which comprises a pair of generally linear compression elements for securing tissue therebetween and for applying to the secured tissue a compression force. The clip assembly has an initial, open position in which the linear compression elements may be positioned about tissue to be secured between them, and a final, closed position whereat the compression elements are substantially parallel to each other, thereby to apply a compressive force to the secured tissue. The clip further comprises a force means disposed between the pair of compression elements and operative to transmit operational forces therebetween.

In embodiments of the present invention the force means is typically formed of a shape memory material.

In some embodiments of the clip assembly of the present invention, the force means includes one or more active hinge members disposed between the linear-compression elements. In some embodiments, each of the linear compression elements has first and second end portions, and the one or more active hinge members are disposed in proximity to a predetermined one of the first and second end portions.

In some embodiments, the assembly further includes a pair of generally linear securing elements, wherein each of the linear compression elements is associated with one of the pair of generally linear securing elements. The securing elements are operative for securing tissue to be compressed by the compression elements and the securing elements and form a securing line when grasping the tissue. The securing line is not collinear with the line of compressive force produced by the compression elements. Typically, the securing elements include a gripping portion having a serrated profile formed of a plurality of teeth-like projections over at least part of the length of the securing elements. The teeth-like projections of the profile are not necessarily uniformly distributed along the length of the gripping portion although in some embodiments they may be. In some embodiments, the assembly further includes one or more receiving structures sized and configured to disengageably receive an attachment element of a clip applier. The clip applier exerts a force counter to the force exerted by the one or more hinge members and is operable for bringing the clip assembly from its closed position to its open position or vice versa.

In some embodiments of the clip assembly, the pair of securing elements and the pair of compressing elements are formed from material selected from the group of materials consisting of: an insulative material and an insulative-coated metal material. In some embodiments, the compressing elements and securing elements are integrally formed with each other. In instances where these are not integrally formed, they may be joined by a method chosen from the group of methods consisting of: welding, gluing, a mechanical clip, fixating joint or a mechanical press.

In another embodiment of the clip assembly, the one or more active hinge members includes first and second hinge members, disposed in proximity to the first and second end portions, respectively, of the linear compression elements. In some embodiments the clip assembly may further include a pair of generally linear securing elements, wherein each of the linear compression elements is associated with one of the pair of generally linear securing elements. The securing elements are operative for securing tissue to be compressed by the compression elements and the securing elements forming a securing line when grasping the tissue. The securing line is not collinear with the line of compressive force produced by the compression elements. In a further embodiment of the clip assembly of the present invention, the securing elements include a gripping portion having a serrated profile formed of a plurality of teeth-like projections over at least part of the length of the securing elements. In some embodiments, the compressing elements and securing elements are integrally formed with each other. In instances where they are not integrally formed, they may be joined by a method chosen from the group of methods consisting of: welding, gluing, a mechanical clip, fixating joint or a mechanical press.

In an embodiment of the present invention, the first and second hinge members each has a generally planar body that includes two legs each having an end portion. Each of the hinge members has located at each of its end portions a connector having a single insertable end portion. The connector is positioned substantially transversally to the planar body. The clip assembly further includes a pair of generally linear securing elements, wherein each of the linear compression elements is associated with one of the pair of generally linear securing elements. The single insertable end portion of the connectors is pivotably connected to the compression elements, allowing concurrent mechanical communication between the hinge members and the compression elements.

In another embodiment of the clip assembly of the present invention, the first and second hinge members each has a generally planar body that includes two legs. Each leg has an end portion. Each of the hinge members has located at each of its end portions a connector having a single insertable end portion. The connector is positioned substantially transversally to the planar body. The clip assembly further includes a pair of generally linear securing elements, and each of the linear compression elements is associated with one of the pair of generally linear securing elements. The single insertable end portion of the connectors is pivotably connected to the securing elements, thereby allowing concurrent mechanical communication between the hinge members and the securing elements.

In yet another embodiment of the clip assembly of the present invention, the first and second hinge members each has a generally planar body that includes two legs each having an end portion. Each of the hinge members has located at each of its end portions a connector having first and second insertable end portions. The connectors are positioned substantially transversally to the planar body. The clip assembly further includes a pair of generally linear securing elements. Each of the linear compression elements is associated with one of the pair of generally linear securing elements. The first end portions of the connectors of the hinge members is pivotably connected to the securing elements, allowing concurrent mechanical communication between the hinge members with the two securing elements. The second insertable end portions of the connectors are pivotably connected to the compressing elements, allowing concurrent mechanical communication between the first and second hinge members and the two compressing elements.

In another embodiment of the clip assembly, the connectors of the first and second hinge members are joined to the legs of the hinge members on an inner surface of the legs. This produces a preloaded clip assembly when the connectors are pivotably connected to one or more of the compressing elements and one or more of the securing elements.

In yet another embodiment, the clip assembly further includes one or more gap forming elements positioned on one or more end portions of one or more compression elements. The gap forming element creates a gap between the compression elements when the clip assembly is in its closed position.

In one embodiment of the present invention, the two legs of the first and second hinge members are each of the same length. In another embodiment of the present invention, the two hinge members are identical but the legs of the hinge members are of different lengths.

In a further embodiment of the clip assembly, one of the compression elements has a hollow tubular structure with an elongated slot at each of its ends positioned on the side of the one of the compression elements proximate to the hinge members. A projection translationally rides in each of the slots and is pivotally connected to the hinge elements and the one compression element mentioned above. When the projections riding in the slots ride away from each other, the longer of the legs of each of the hinge members travel in opposite directions from each other. This causes the hinge members to bring the clip assembly to its open position. When the projections ride in the slots towards each other the longer of the legs of each of the hinge members travel toward each other causing each of the hinge members to bring the clip assembly to its closed position.

In yet another embodiment of the clip assembly of the present invention, the clip assembly further includes two joined threaded bolts positioned inside the hollow compression element. Each of the bolts has a different handedness and each has a threaded cylinder with an extension fitted thereon. Each of the extensions is pivotably connected to one leg of a different one of the hinge members. The extensions are operable as the projections for riding along the elongated slot when the threaded bolts are rotated. When rotating the joined bolts in one direction, the projections, being in mechanical communication with the bolts, travel in the slots in a direction away from each other. This brings the clip assembly to its open position. When rotating the joined bolts in a second direction, the projections travel in the slots in a direction toward each other thereby bringing the clip assembly to its closed position.

In another embodiment of the invention, each of the hinge members has a connector positioned near the end portion of one of its legs. The connector serves as the projection for insertion into and translationally riding in the slots. The clip assembly further includes wires connected to the connectors. When the wires are pulled in one direction the connectors travel in the slots in a direction away from each other thereby bringing the clip assembly to its open position. When the wires are released, the connectors travel in the slots in a direction toward each other, bringing the clip assembly to its closed position.

In another embodiment of the clip assembly, the assembly further includes one or more receiving structures sized and configured to disengageably receive an attachment element of a clip applier. The clip applier exerts a force counter to the force exerted by the one or more hinge members and is operable for bring the clip assembly from its closed position to its open position or vice versa.

In another embodiment of the present invention, the one or more active hinge members includes a single member, disposed in proximity to the first end portions of the linear compression elements. When the clip assembly is in the open position, the linear compression elements form a jaws-like arrangement and the second end portions of the linear compression elements are spaced apart so as to permit positioning of the compression elements about tissue to be secured therebetween. In instances of this embodiment, the single hinge member is fixably connected to the first end portions of the linear compression elements.

In other embodiments of the present invention, there is a selectably movable latch member positioned within a first of the two compression elements and extending past its second end portion. There is an engagement means on the second end of the second compression element for engaging and holding the latch member in force producing engagement when the pair of compression elements are brought close to each other, and when the latch member is moved to engage with the engagement means.

In another embodiment of the present invention, the assembly further includes a wire extending between the second end portion of each of the two compression elements. The wire is releasably connected to the latch member and has an extension extending via the second end portion of the second compression element through the first compression element. The extension is operative to draw the wire taut when tissue is positioned between the two compressing elements. The taut wire thereby prevents the tissue from moving out from between the pair of compression elements while the clip assembly is brought to its closed position.

BRIEF DESCRIPTION OF THE DRAWINGS

The present invention will be more fully understood and its features and advantages will become apparent to those skilled in the art by reference to the ensuing description, taken in conjunction with the accompanying drawings, in which:

FIGS. 14 and 15 show isometric views of a second embodiment of a surgical compression clip constructed according to the present invention, wherein FIG. 14 and FIG. 15 show the clip in its closed and open positions, respectively;

Similar elements in the Figures are numbered with similar reference numerals.

DETAILED DESCRIPTION OF THE PREFERRED EMBODIMENTS

Figure 1A:
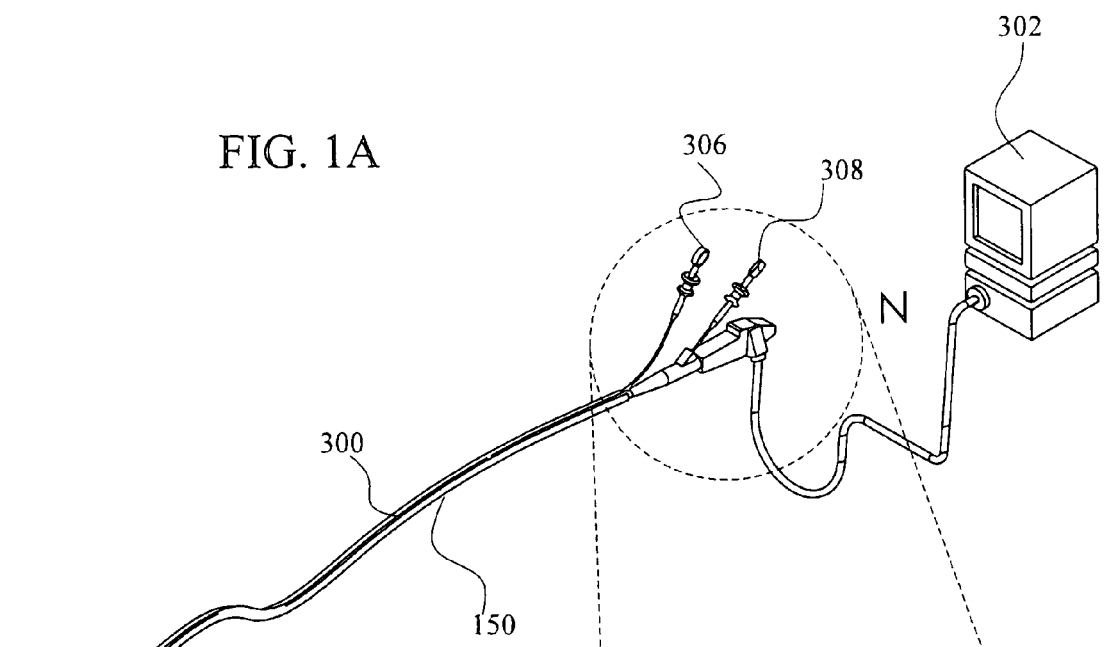
FIG. 1A is an overall isometric view of an endoscopic system constructed according to the present invention.

The present application should be read in conjunction with co-pending U.S. application "Endoscopic Full Thickness Resection Using Surgical Compression Clips", filed by the same applicant and inventors concurrently on Dec. 29, 2006. This document is herein incorporated by reference in its entirety.

The present invention describes non-unitary surgical compression clips, which lessen the likelihood of internal leakage of bodily fluids which often occurs when staple suturing is used. These clips, when used, also lessen the likelihood of bleeding and do not leave any permanent foreign body inside the body cavity after tissue closure and healing is complete.

The non-unitary, i.e. compound, surgical compression clips described herein, typically have one or more elements, generally two or more elements, made of a shape memory material, such as a nickel-titanium (Ni—Ti) alloys. The clip includes two compressing elements connected operationally by at least one of the shape memory elements. Typically, the clip also includes securing elements with which to hold the tissue being compressed. Also typically, the compressing elements are linear as are the securing elements. When tissue to be joined is held between the two compressing elements, a constant compressive force acts between the two elements, these latter being connected at both of their ends by the shape memory elements. The constant force is a result of the well-documented long plateau region of the shape memory material's stress-strain hysteresis curve. In this plateau region, the force is constant irrespective of the extent of the deformation. This is a consequence of properties exhibited by shape memory materials. Additionally, stress-induced strain is recoverable in these materials; in the case of nitinol, 6-8% of the strain can be recovered.

Discussions of the stress-strain curves of shape memory materials and its stress induced strain can be found in many publications. See for example "Shape Memory Materials", edited by K. Otsuka and C. M. Wayman, Cambridge University Press 1998, p. 62 and; H. Tobushi et al in "Deformation Behaviour of Ni—Ti Superelastic Alloy Subjected to Strain Variation" in SMST-94: The Proceeding of the International Conference on Shape Memory and Superelastic Technology, edited by A. Pelton, D. Hodson and T. Duerig, 1995, pp. 389-391.

It should be noted that the line of compressive force produced by the compression elements of the clips of the present invention is not collinear with the line exerted by the securing elements on the tissue to be resected. These are two different lines of action, separated by a distance. Were they to be co-linear the healing of the tissue at the compression site may be compromised. Additionally the arrangement of non-colinearity allows for more homogeneous tissue compression by the compression elements. Any penetration of the teeth for securing the tissue is compensated for by the continuous compression line more proximate to the body cavity wall.

The shape memory elements, which act as force appliers, are typically made of nickel-titanium (Ni—Ti) alloys but other shape memory materials may also be used. The other elements of the clip, i.e. the compressing elements and the securing elements (and possibly separate toothed elements for attachment to the securing elements when there is no integrally formed toothed edge on the securing elements) may also be made of a shape memory material such as a nitinol alloy, but that is not essential. Other metals or alloys, such as stainless steel or other titanium alloys, and even certain plastic materials may also be used. The compression clips described herein are typically attached to an applier and brought to tissue adjacent to a resection site, or to tissue adjacent to a perforation to be joined, or to any tissue having an opening requiring closure.

It should be noted that the line of compressive force produced by the compression elements of the clips of the present invention is not collinear with the line exerted by the securing elements on the tissue to be resected and/or closed. These are two different lines of action, separated by a distance. Were they to be co-linear the clip could easily disengage before scar tissue matured at the compression site. Additionally, the non-collinear arrangement allows for more homogeneous tissue compression by the compression elements. Furthermore, any penetration of the teeth on the securing elements for securing the tissue is compensated for by the clip's continuous compression line being further away from the resected site or the opening to be closed.

The surgical clips described herein may be used with standard commercially available endoscopes. Dedicated or specially designed endoscopes can be used but are not necessary.

Additionally, using the compression clips of the present invention is not limited to any particular direction or shape of resection incision; both radial and longitudinal incisions are contemplated by the present invention.

The surgical clips described herein have additional advantages. The compression force ensures continuous compression of the tissue at the resected site, independent of the variation in tissue thickness. No foreign bodies are left behind in the body cavity as the clip is typically self-evacuating. Finally, since the invention makes use of shape memory materials, the clip may be of relatively small dimensions and there is no need for large instruments, such as currently employed stapler firing mechanisms. This permits easier advance of the clip and its applier to a site requiring closure.

Before explaining several embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1B:
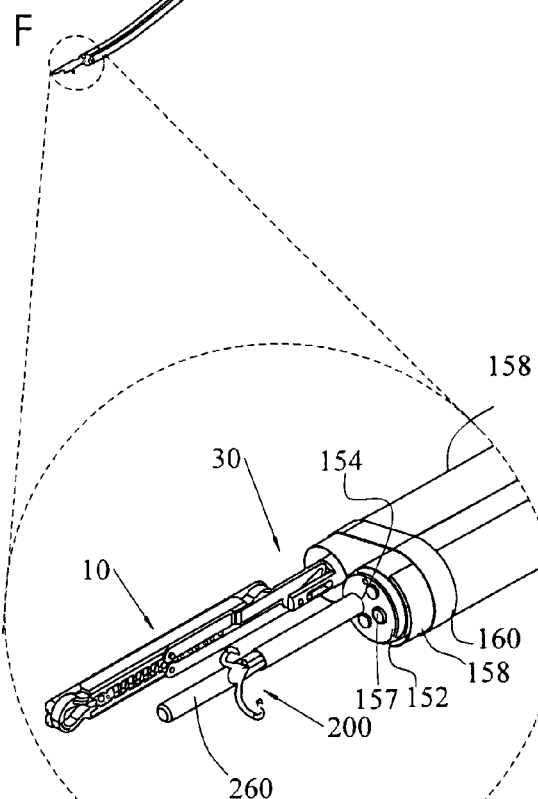
FIG. 1B is an enlarged view of the distal end of the endoscopic system shown in FIG. 1A.
Figure 1C:
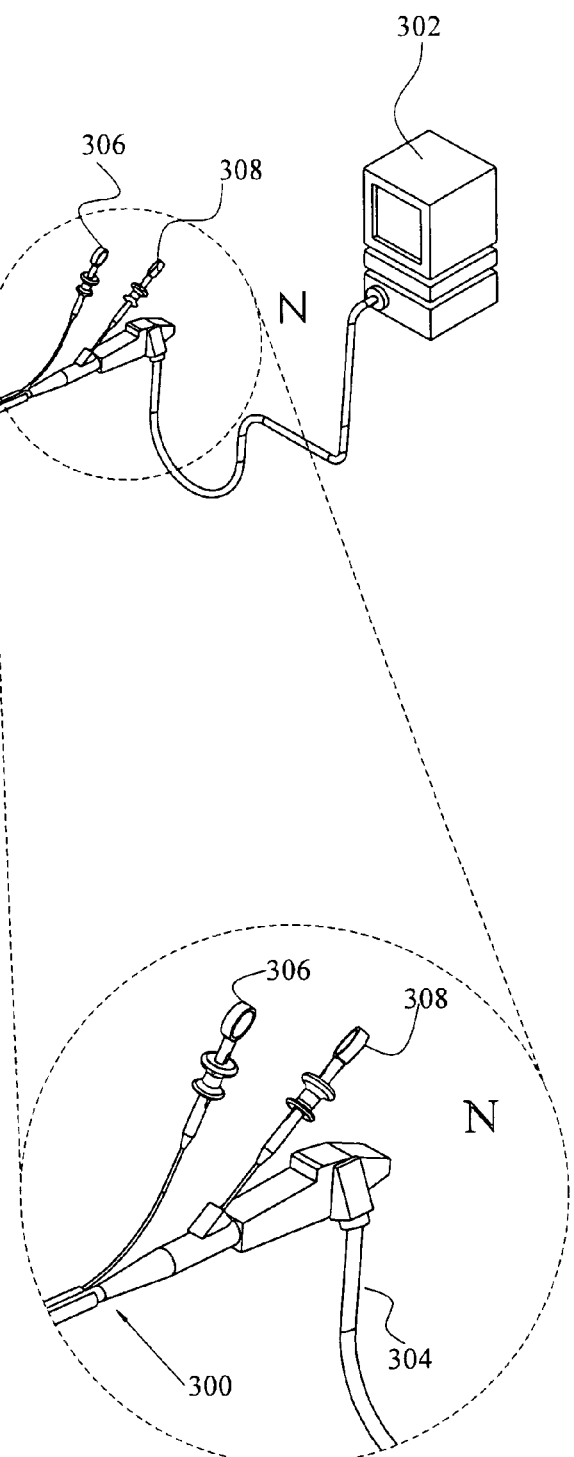
FIG. 1C is an enlarged view of the proximal end of the endoscopic system shown in FIG. 1A.

FIGS. 1A-1C, to which reference is now made, show an overall view of an endoscopic system constructed according to the present invention, an enlarged view of the system's distal end F and an enlarged view of the system's proximal end N, respectively.

FIG. 1A includes an endoscope insertion shaft 300 encased in a multi-lumen sleeve 150. At the distal end F of endoscope insertion shaft 300, working instruments constructed according to the present invention may exit. These instruments include a surgical clip 10 attached to an applier 30 and a grasper assembly 200 including a grasper transporting element 260. These instruments are inserted into a working channel 154 of endoscope insertion shaft 300 or one or more secondary lumens 158 of sleeve 150. Insertion of the instruments is effected at the proximal end N of endoscope insertion shaft 300. They are advanced in the direction of, and ultimately exit at, or adjacent to, the distal end F of endoscope insertion shaft 300. Actuators 306 and 308 may be any of many known to those skilled in the art. They can apply one or a combination of control actions or movements, such as pull and release, articulation, swivel and the like. Endoscope insertion shaft 300 is typically connected to a fiberoptic cable 304 which communicates images to a visual display 302.

Details of the instruments used, the multi-lumen sleeve and other specific aspects of the system of the present invention are further discussed below.

Figure 2:
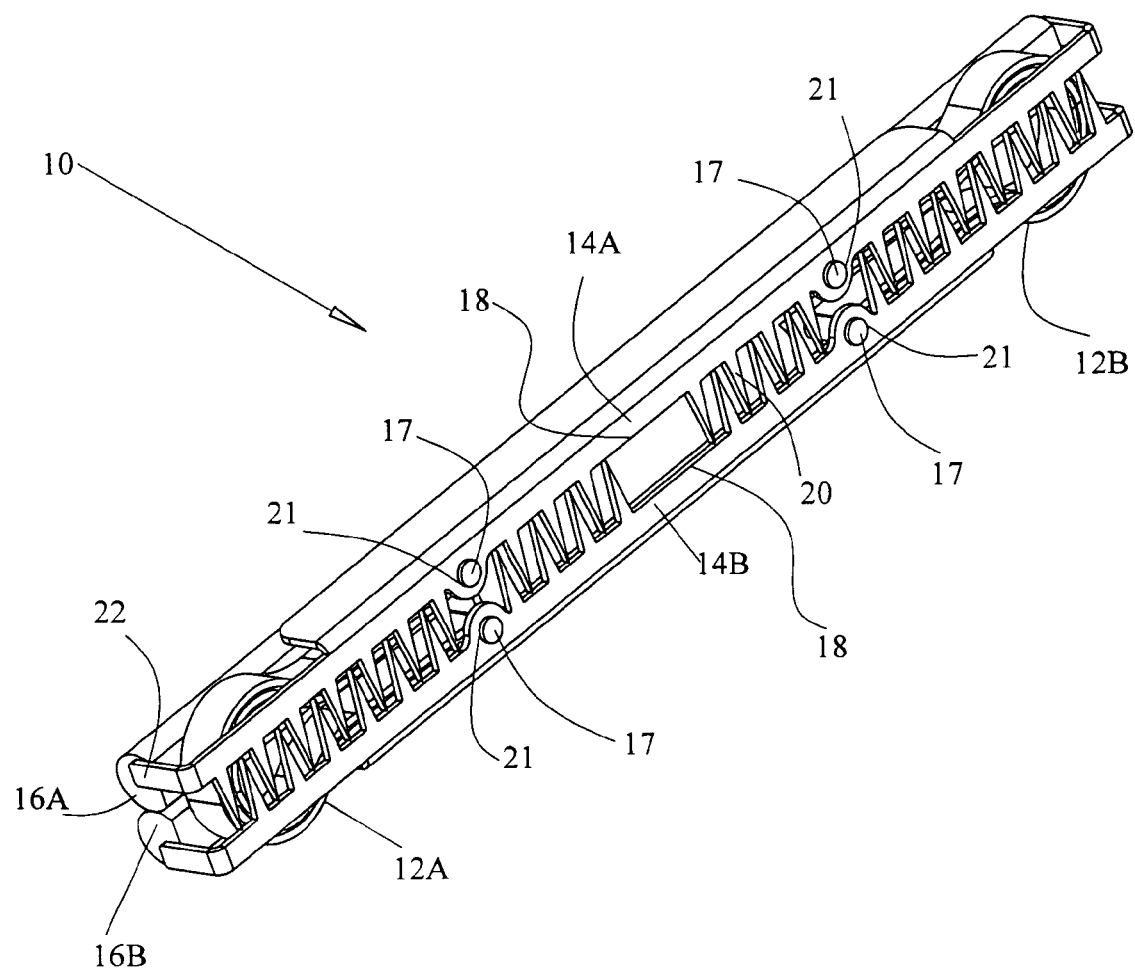
FIG. 2 shows an isometric view of the compression clip constructed according to a first embodiment in its closed position.
Figure 3A:
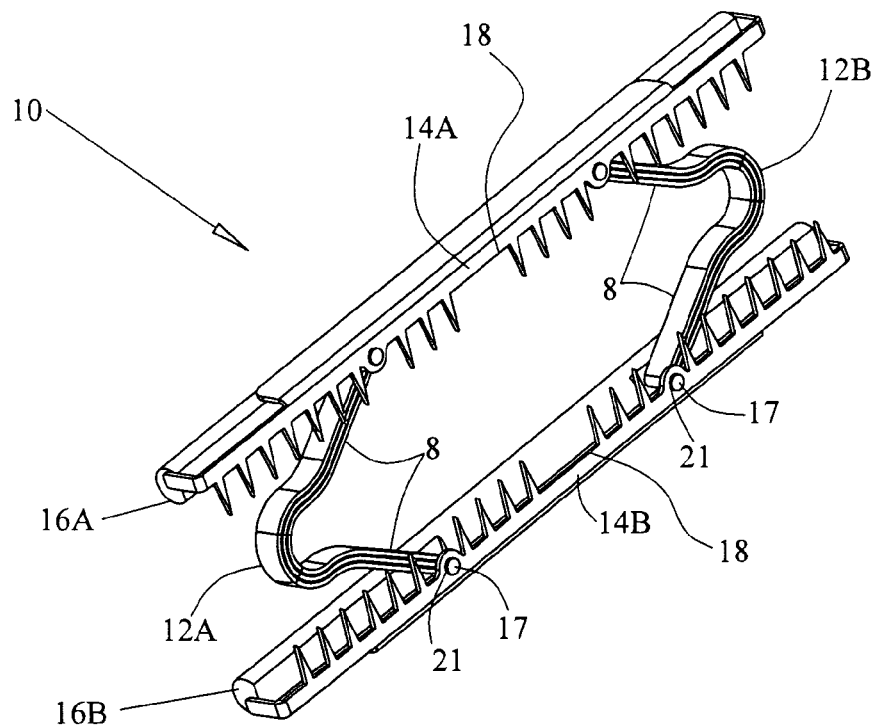
FIGS. 3A and 3B show isometric top and bottom views of the compression clip shown in FIG. 2 in its open position.
Figure 3B:
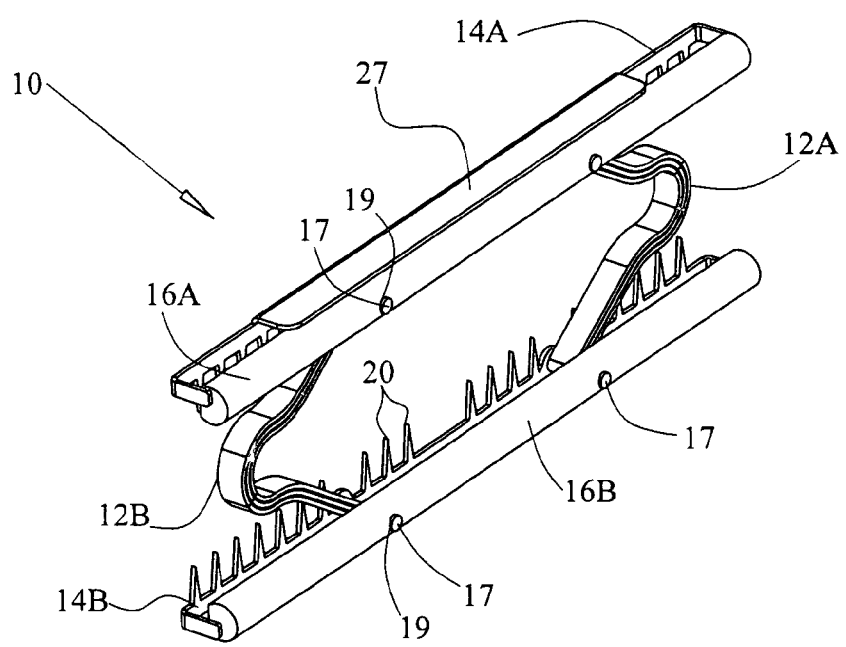

Reference is now made to FIGS. 2-3B where FIG. 2 presents a view of a non-unitary compression clip constructed according to a first embodiment of the present invention. In FIG. 2 the clip is shown in its closed position. FIGS. 3A and 3B present a view of the compression clip shown in FIG. 2 in its open position.

Clip 10 is constructed of two shape memory hinge springs 12A and 12B, also herein often denoted as force appliers. Typically, but without intending to be limiting, the shape memory material is a Ni—Ti alloy. The operation of the clip relies on shape memory effects exhibited by these materials. Springs 12A and 12B may be made of a single wire or flattened wire or strip or it may be constructed of two or more wires, flattened wires or strips connected together at their ends. Furthermore, in some embodiments, the springs may be constructed to have a coiled shape.

Clip 10 further includes two securing elements 14A and 14B, each of which has a series of teeth 20 for grasping tissue. Each of securing elements 14A and 14B may be formed from a single piece or welded together from several pieces, typically but without intending to be limiting, of metal. Teeth 20 may be formed integrally with elements 14A and 14B or they may be joined to the elements, for example, by welding. Generally, these securing elements are made of metal and typically are welded or otherwise joined to two metal compressing elements 16A and 16B. However, the securing elements and the compressing elements may be joined together by any method known to those skilled in the art. Securing elements 14A and 14B may also be formed integrally with compressing elements 16A and 16B, respectively.

Securing elements 14A and 14B are formed with spacings 18 configured and sized to receive the pushing elements of a clip applier (not shown). Compressing elements 16A and 16B, typically, but without intending to be limiting, are cylindrically-shaped. These include holes 19 (best seen in FIG. 3B) into which connectors 17 (also best seen in FIG. 3B) of hinge springs 12A and 12B are insertable. Insertion of hinge springs 12A and 12B occurs prior to welding or otherwise joining toothed securing elements 14A and 14B to compressing elements 16A and 16B, respectively. As a result of the weld or other joining method, securing elements 14A and 14B prevent connectors 17 of hinge springs 12A and 12B from dropping out of holes 19. Securing elements 14A and 14B, and compressing elements 16A and 16B are joined together by hinge springs using any method known to those skilled in the art, particularly in the art of articulation hinges (swing joints). The natural tension of hinge springs 12A and 12B operates to keep compressing elements 16A and 16B in their closed position as in FIG. 2.

The metal used for forming securing elements 14A and 14B, compressing elements 16A and 16B and teeth 20, if these latter are made from separate pieces and welded to elements 14A and 14B, should be a rigid metal such as, but without being limiting, stainless steel.

While in the above embodiment, securing elements 14A and 14B are welded to compressing elements 16A and 16B, respectively, in other embodiments this need not be the case. The securing and compressing elements may be joined to each other by mechanical means such as by U-shaped elements positioned on securing elements 14A and 14B clippably engageable to compressing elements 16A and 16B or by press connections wherein an edge on each of securing elements 14A and 14B would be pressed to enter a slit in their respective compressing elements 16A and 16B. Alternatively, securing elements 14A and 14B and compressing elements 16A and 16B can be crimped together.

In other embodiments, securing elements 14A and 14B and compressing elements 16A and 16B may be made of a single piece of plastic, for example by ejection molding. In such embodiments, only hinge springs 12A and 12B are made of metal, specifically a shape memory metal or alloy, typically but without intending to be limiting, a Ni—Ti alloy. In such plastic embodiments, hinge springs 12A and 12B (force appliers) would typically be snapped into place between securing elements 14A and 14B and compressing elements 16A and 16B. However, it is evident to one skilled in the art that other methods of introducing the metal hinge springs 12A and 12B could also be used.

Clip 10 in its closed position appears as shown in FIG. 2. Hinge springs 12A and 12B exert no force when the clip is fully closed, i.e. when compressing elements 16A and 16B lie proximate and tangent to each other. However, as compressing elements 16A and 16B are separated apart, hinge springs 12A and 12B exert a force which tries to bring compressing elements 16A and 16B and securing elements 14A and 14B together. When clip 10 is to be opened, pushing elements of a clip applier (not shown) may be positioned and wedged between teeth 20 of securing elements 14A and 14B or they may be positioned in a spacing or indentation 18. The applier is activated to apply a force via its pushing elements (not shown). This force opposes the force exerted by hinge springs 12A and 12B. This counter force spreads securing elements 14A and 14B and compressing elements 16A and 16B apart. It also spreads hinge springs 12A and 12B as in FIGS. 3A and 3B.

After tissue is brought to and positioned between the separated compressing elements 16A and 16B, the applier is operated to relax the applied force allowing securing elements 14A and 14B to move toward each other and to return to their original closed position (FIG. 2). Shape memory hinge springs 12A and 12B also relax and return to their original shape. The tissue positioned between the securing and compressing elements of clip 10 prevents compressing elements 16A and 16B and springs 12A and 12B from completely returning to their original closed positions. Once the compressing elements are stopped by the tissue, continued closure of the applier's pushing elements leads to separation of the pushing elements of the applier from securing elements 14A and 14B of clip 10. This, in turn, causes the applier to disengage from clip 10.

While the shape memory elements used to effect opening or closing of clip 10 are here described as hinge springs, these elements can more generally be classified as force appliers. Therefore, it should be understood that elements of any shape which can generate a force for either opening or closing a compression clip may be used and these elements can and will often be denoted herein as force appliers.

In other embodiments, pushing elements of a clip applier are inserted into special indentations in securing elements 14A and 14B. The spacing/indentation is best seen as element 718 in FIGS. 25A and 26A discussed below. In yet another embodiment, when pushing securing elements 14A and 14B, the pushing elements of an applier (not shown) are inserted and loosely held in holes (not shown) positioned on securing elements 14A and 14B.

Figure 4A:
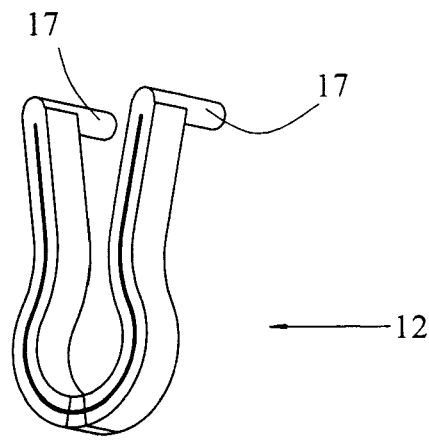
FIGS. 4A, 4B and 4C show isometric views of different configurations of spring elements constructed according to various embodiments of the present invention.
Figure 4B:
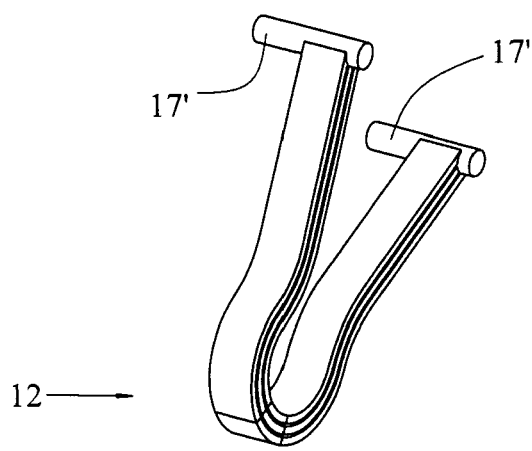
Figure 4C:
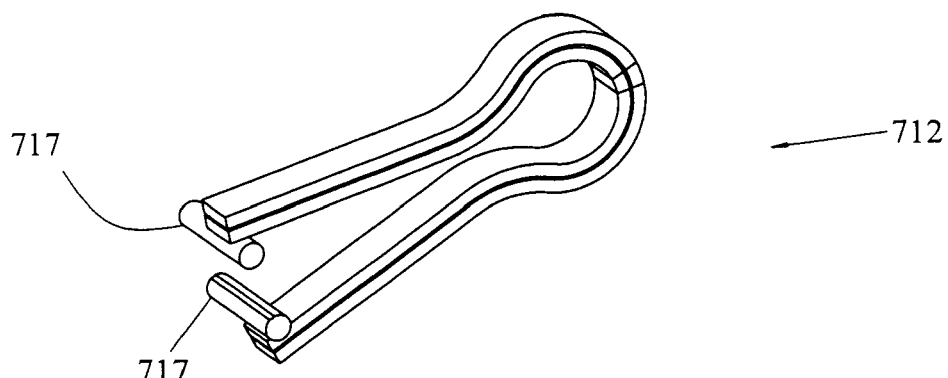

Shape memory hinge springs 12A and 12B can have distinctive connectors 17 at their ends as shown in FIGS. 4A-4C. A hinge spring having uni-directional connectors 17 is shown in FIG. 4A. However, the use of hinge springs with bi-directional connectors 17' as shown in FIG. 4B is advantageous over the unidirectional connectors 17 shown in FIG. 4A. The hinge spring's bi-directionality allows connectors 17' to be inserted simultaneously into holes 21 in securing elements 14A and 14B and into holes 19 in compressing elements 16A and 16B. This increases stability of the clip 10. It also reduces the chance that hinge springs 12A and 12B will be displaced during operation of the clip and interfere with closure of the clip. The positioning of hinge springs 12A and 12B with connectors 17' can readily be seen in FIGS. 2, 3A and 3B where clip 10, in its closed and open positions, is shown. Reference to the use of hinge springs with connectors of the type of connector 717 shown in FIG. 4C will be made later in the text.

Connectors 17, 17' and 717 shown in FIGS. 4A, 4B and 4C respectively-form articulating joints when they are inserted into corresponding apertures or holes in compression elements and/or securing elements as described in the first through fourth compression clip embodiments described below. These connectors rotate or swing in their respective apertures and holes allowing for articulation.

It should be noted that as in clip 10 of FIGS. 2-3B, in some embodiments teeth 20 do not necessarily extend the entire length of securing element 14A and 14B while in others they do. Additionally, it should be noted that in some embodiments of clip 10 in FIGS. 2-3B, teeth 20 need not be distributed uniformly along securing elements 14A and 14B. Additionally, at both ends of elements 14A and 14B there is a small bend 22 welded or otherwise joined to the sides. In some embodiments, bend 22 may be integrally formed as part of elements 14A and 14B. This provides extra security against clip 10 slipping off the compressed suspect tissue during resection.

In the compression clip embodiments shown in FIGS. 2-3B and as discussed elsewhere in this specification, the securing elements and their respective compressing elements have been described as separate elements. In their operational state within the clips, these are typically a single joined element reflecting a single part and may be thought of as such. In the joined part, the securing elements attach to and grip the tissue to be resected while the compressing elements act to press the parts of the resected site together even when they are formed as separate elements and are only later joined together to operate as a single part.

Reference is now made to FIGS. 5-9 where various views of a first embodiment of a clip applier are shown. The clip applier may be used with surgical compression clip 10 shown in and described in conjunction with FIGS. 2-3B.

Figure 5:
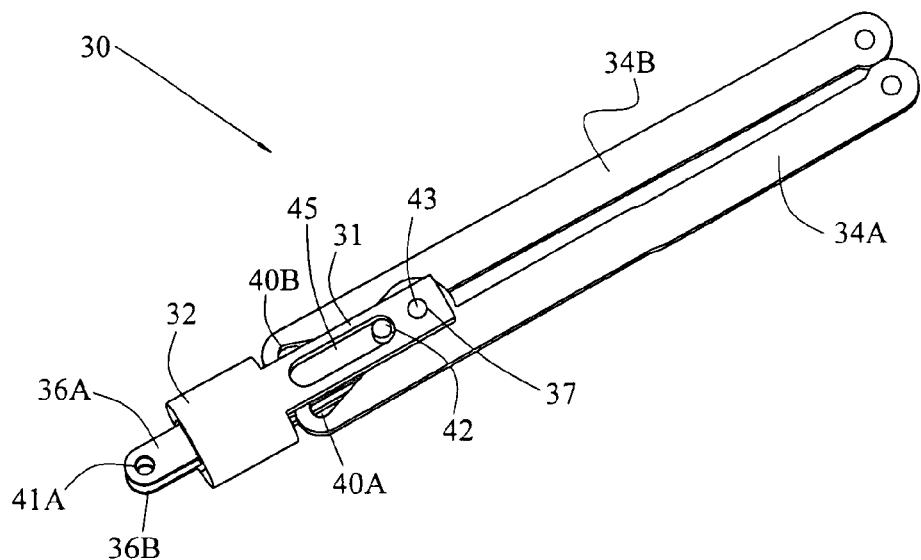
FIG. 5 is an isometric view of a clip applier constructed according to one embodiment of the present invention, the applier in its closed position.

FIG. 5 shows clip-applier 30 in its closed position. Clip applier 30 is comprised of applier arms 34A and 34B, applier base 32, and connector elements 36A and 36B. The elements of clip applier 30 are typically constructed of stainless steel but they may also be constructed of other metals, such as, but not limited to, titanium, titanium alloys or reinforced plastics.

Figure 6:
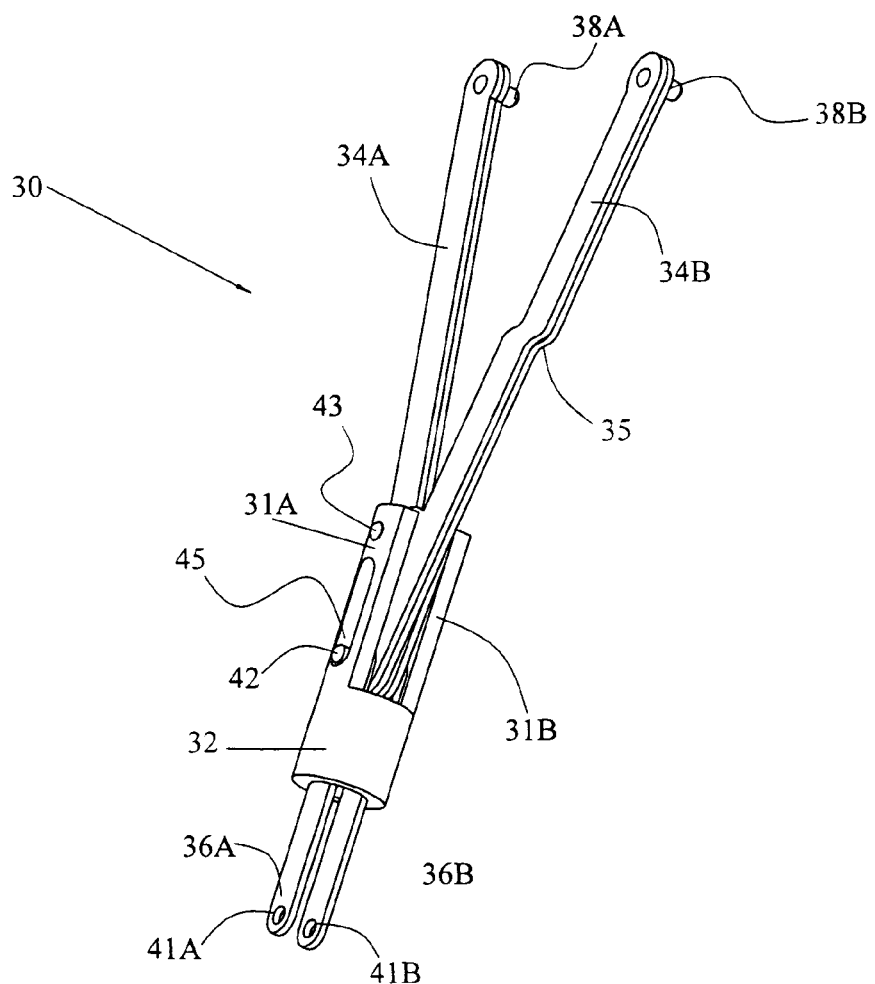
FIG. 6 is an isometric view of the clip applier in FIG. 5, the applier in its open position.

As best seen in FIG. 6 where clip applier 30 is shown in it open position, each of applier arms 34A and 34B has, at its distal end, an insertion projection 38A and 38B, respectively. Insertion projections 38A and 38B are formed substantially transverse to applier arms 34A and 34B and are operative for insertion between teeth 20 of securing elements 14A and 14B in FIG. 2, or into indentations 718 of clip 710 in FIG. 25A, or alternatively into holes positioned in securing elements 14A and 14B and compressing elements 16A and 16B.

Figure 7:
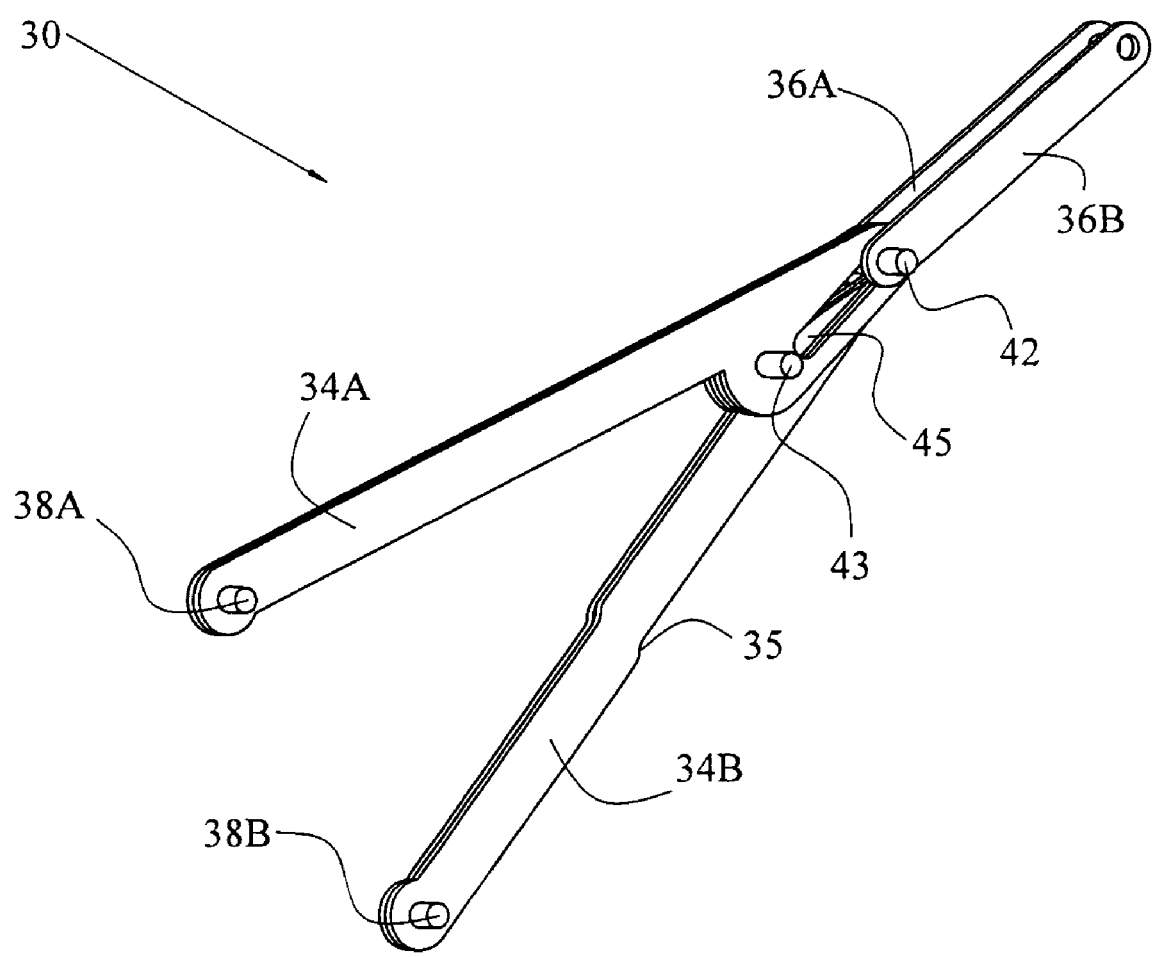
FIG. 7 is an isometric view of the clip applier in FIG. 5 without its base element, the applier in its open position.

FIG. 7 shows open clip applier 30 without its applier base 32.

As seen in FIGS. 5 and 6, applier base 32 has a generally barrel-like shape from which emerges a pair of applier base projections 31. Each of these projections 31 has an applier base slot 45 and an applier base projection hole 37. Each of applier arms 34A and 34B has at its proximal end applier arm slots 40A and 40B and applier arm holes (not shown). Applier arm 34B is constructed with a bend 35 in it so that the distal portions of arm 34B and arm 34A can lie in the same plane. It also allows insertion projections 38A and 38B to lie in the same plane.

Each of connector elements 36A and 36B has a pair of holes 41A-41D (41C and 41D not visible), one at each end of each element.

Applier arms 34A and 34B are joined to applier base 32 by connecting pin 43 which passes through applier base projection holes 37 and applier arm holes (not shown). Pin 42 is inserted into holes (not shown) in connector elements 36A and 36B and is movable in applier base slots 45 and applier arm slots 40A and 40B. As pin 42 moves it forces applier arm slots 40A and 40B to overlap with applier base slots 45 at the point of the pin, thus creating an opening and closing effect.

The proximal ends of connector elements 36B and 36A, respectively, are attached to an operating cable (not shown) that exits the proximate end of the endoscope. The cable is activated by an actuator 306 (FIG. 1A), for example, positioned outside the proximal end N (FIG. 1A) of the endoscope.

Figure 8:
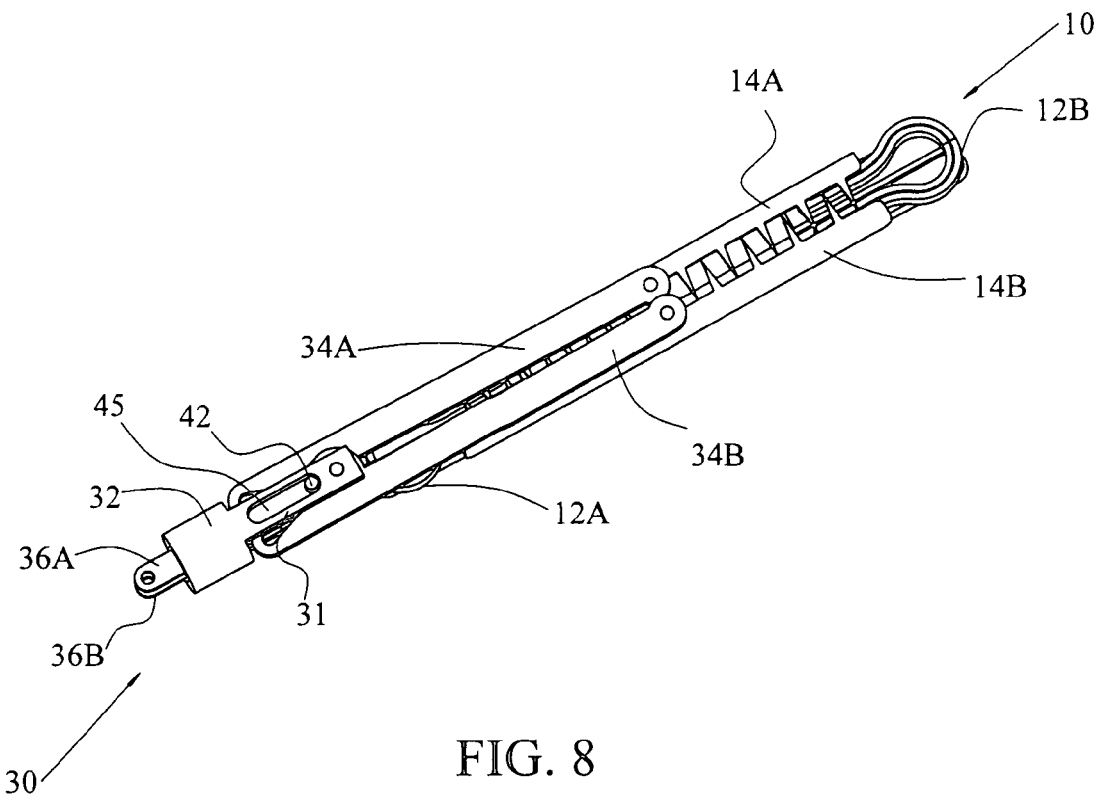
FIG. 8 is an isometric view of the clip applier of FIG. 5 used to position the clip in FIG. 2, the clip being attached to the applier and in its closed position.
Figure 9:
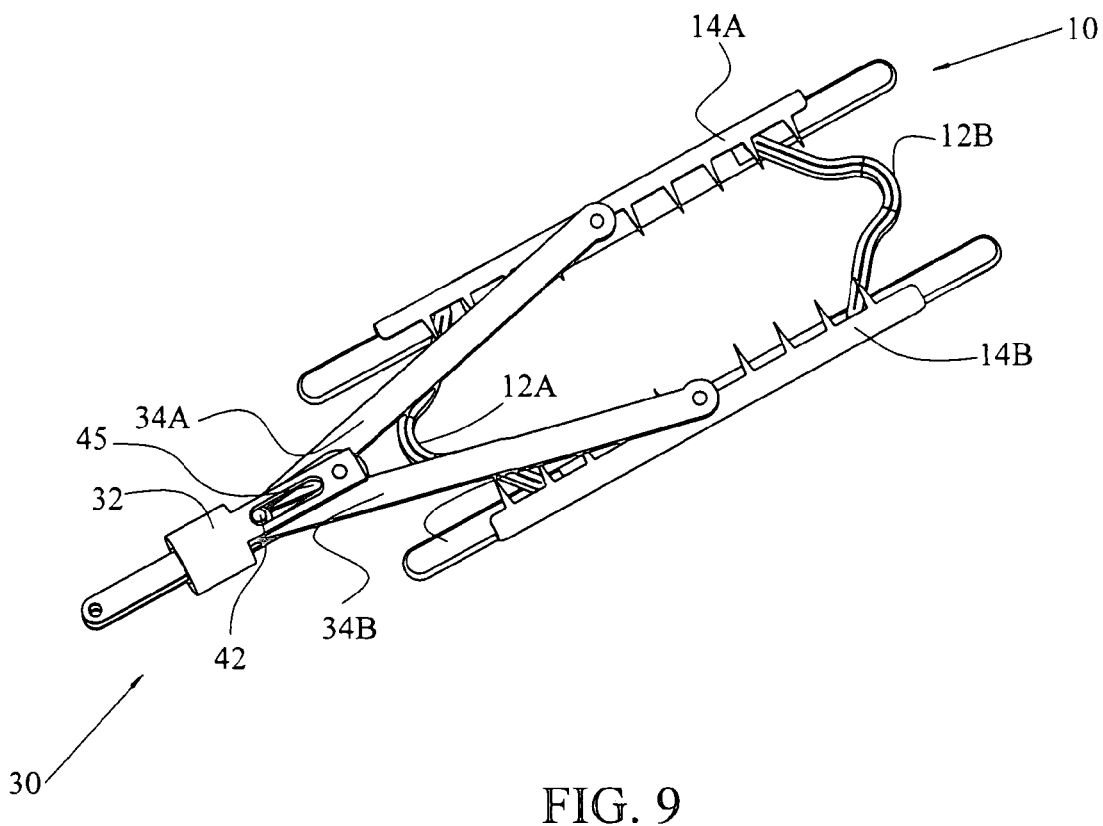
FIG. 9 is an isometric view of a clip applier used to position the clip in FIG. 2, the clip being attached to the applier and in its open position.

FIG. 8 and FIG. 9 show clip applier 30 of the present embodiment attached to surgical compression clip 10 described in FIGS. 2-3B in its closed and open position, respectively.

To open clip applier 30, an operating cable (not visible) pulls connector elements 36A and 36B in the proximal direction. Concurrently, pin 42 moves to the proximal end of applier base slots 45 and the proximal ends of applier arm slots 40A and 40B. In that position, applier arms 34A and 34B move apart as in FIG. 9.

To close clip applier 30, the tension in the operating cable (not visible) is released. In doing so, the force that hinge springs 12A and 12B exert is greater than that of the operating cable. A force is thus exerted on applier arms 34A and 34B through securing elements 14A and 14B. The clip's force brings applier arms 34A and 34B together, which pushes connector elements 36A and 36B in the distal direction. Concurrently, pin 42 moves to the distal end of applier base slots 45 and the distal ends of applier arm slots 40A and 40B. In that position, applier arms 34A and 34B move together as in FIG. 8.

Figure 26A:
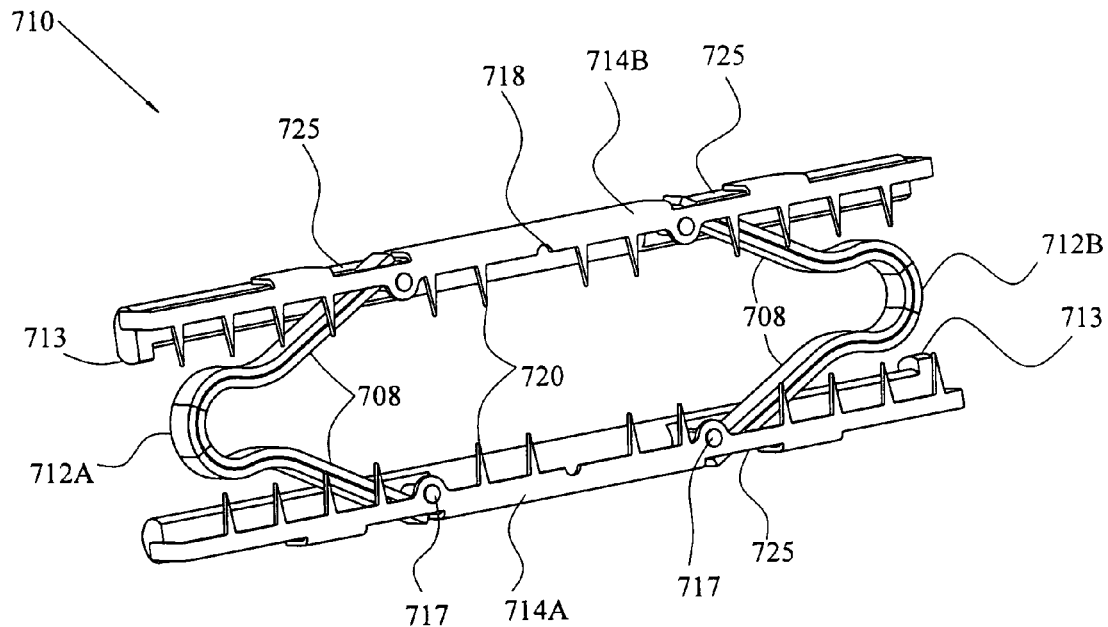
FIGS. 26A and 26B are an isometric top and bottom view of a clip constructed according to the embodiment of FIGS. 25A and 25B, the clip being in its open position.
Figure 26B:
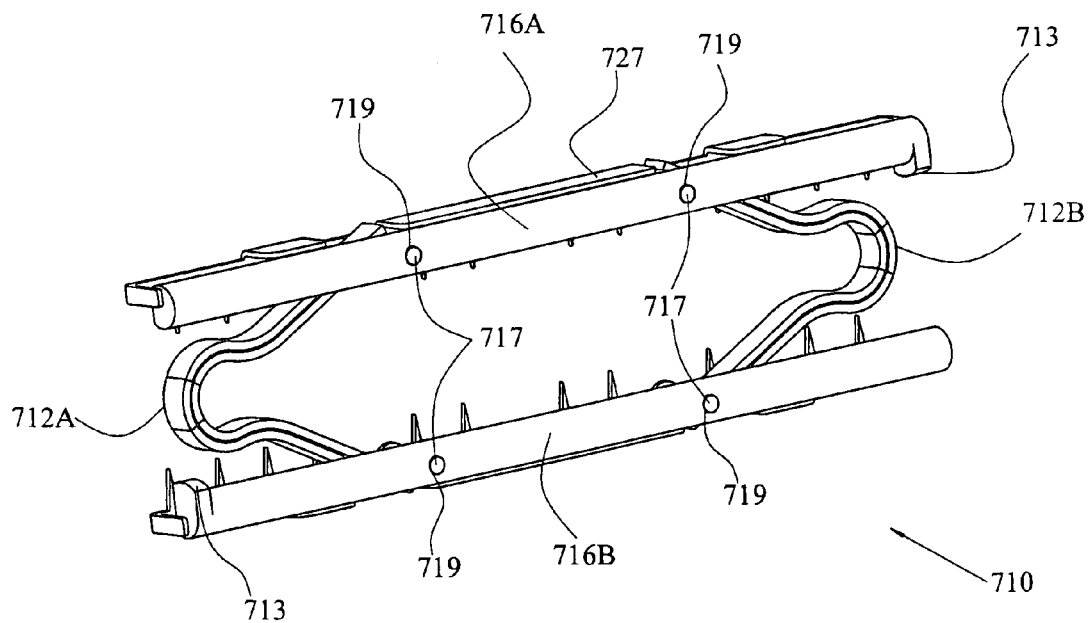

When applier arms 34A and 34B are pushed apart as in FIG. 9, insertion projections 38A and 38B of clip applier 30 push against the spacings between teeth 20 of securing elements 14A and 14B of clip 10 shown in FIG. 2 (or indentations 718 of clip 710 shown in and discussed below in conjunction with FIGS. 26A and 26B) so that securing elements 14A and 14B and compressing elements 16A and 16B of clip 10 move apart. When applier arms 34A and 34B are moved together as in FIG. 8, insertion projections 38A and 38B of clip applier 30 exert a reduced force on the spacings between the teeth 20 of securing elements 14A and 14B of clip 10 in FIG. 2 (or on indentions 718 of clip 710 shown in and discussed in conjunction with FIGS. 26A and 26B) so that securing elements 14A and 14B and compressing elements 16A and 16B of clip 10 move together. The counter force exerted by hinge springs 12A and 12B keeps clip applier 30 in place. Once tension generated by springs 12A and 12B is reduced sufficiently, that is as clip 10 closes on and compresses tissue, insertion projections 38A and 38B of applier 30 essentially fall away and disengage from clip 10.

Figure 10:
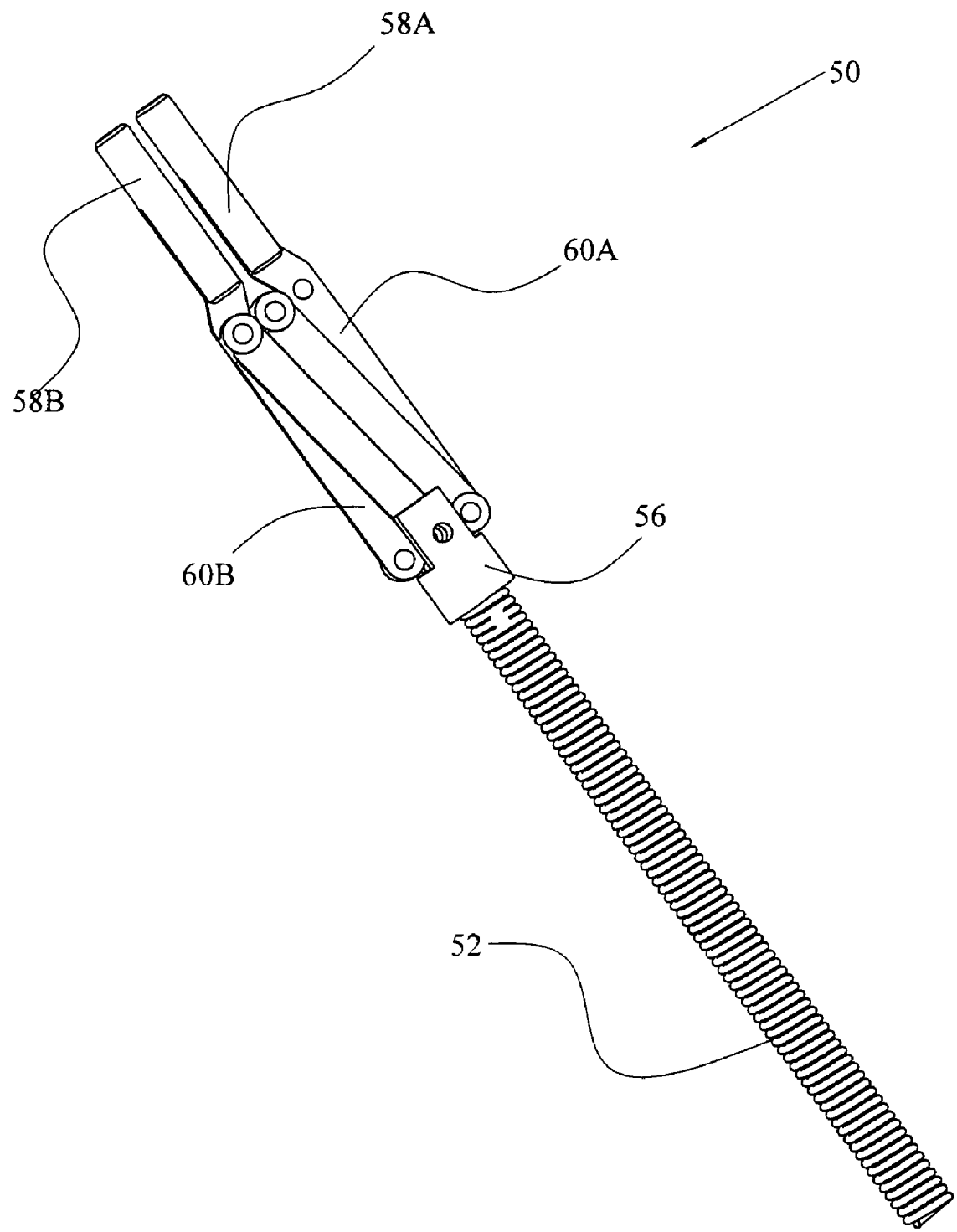
FIG. 10 is an isometric view of a clip applier constructed according to a second embodiment of the present invention, the applier in its closed position.
Figure 11:
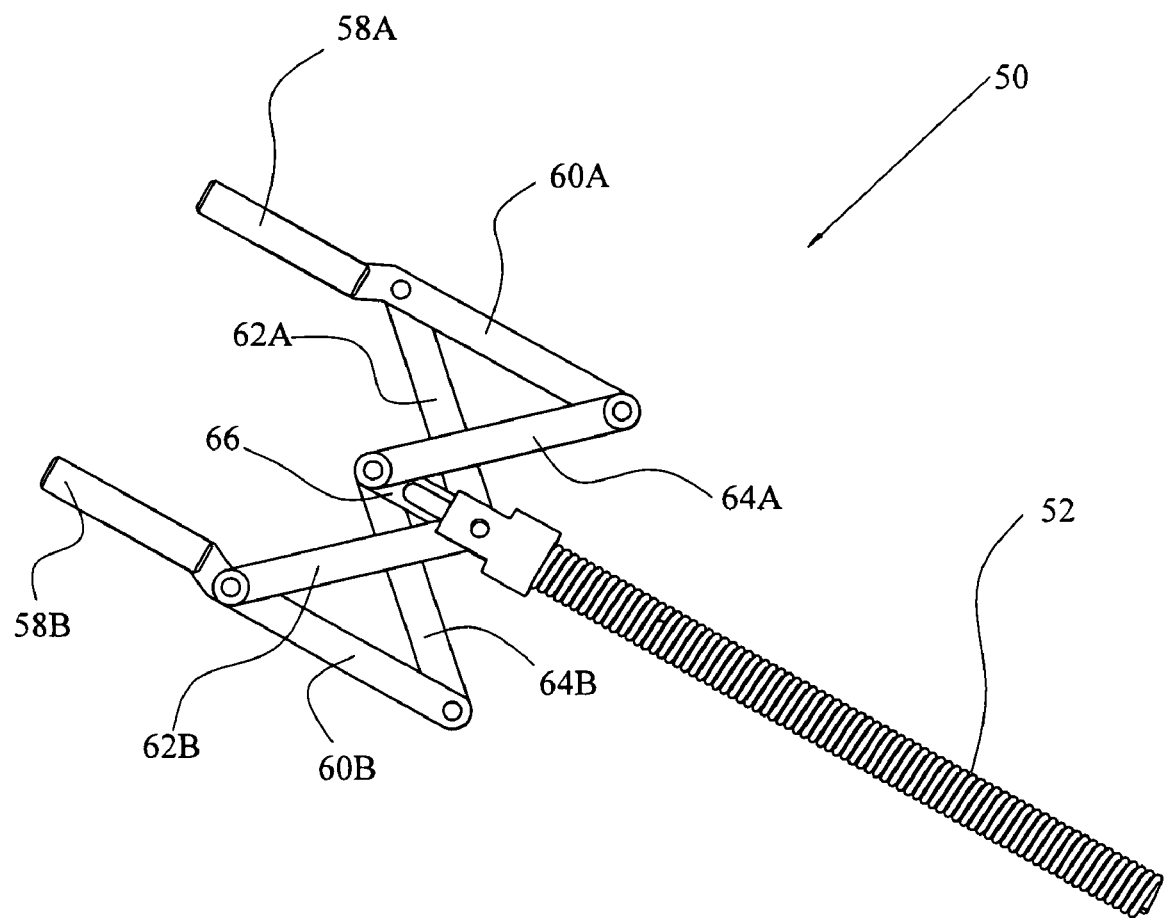
FIG. 11 is an isometric view of the clip applier in FIG. 10, the applier in its open position.

FIGS. 10-13, to which reference is now made, show various views of a second embodiment of a clip applier constructed according to the present invention. The applier is intended for use with the surgical compression clip (slightly modified as discussed below) shown in and discussed in conjunction with FIGS. 2-3B. FIG. 10 shows the clip applier in its closed position, while FIG. 11 shows the applier in its open position.

Turning to FIG. 11 first, clip applier 50 includes insertion links 60A and 60B which are swing jointed by links 62A, 62B, 64A, 64B and central bar 66. An operating cable (not shown) is connected to the proximal end of central bar 66 and inserted into spring 52. The latter connection can be achieved by welding or any other connecting method or means known to those skilled in the art.

Figure 12:
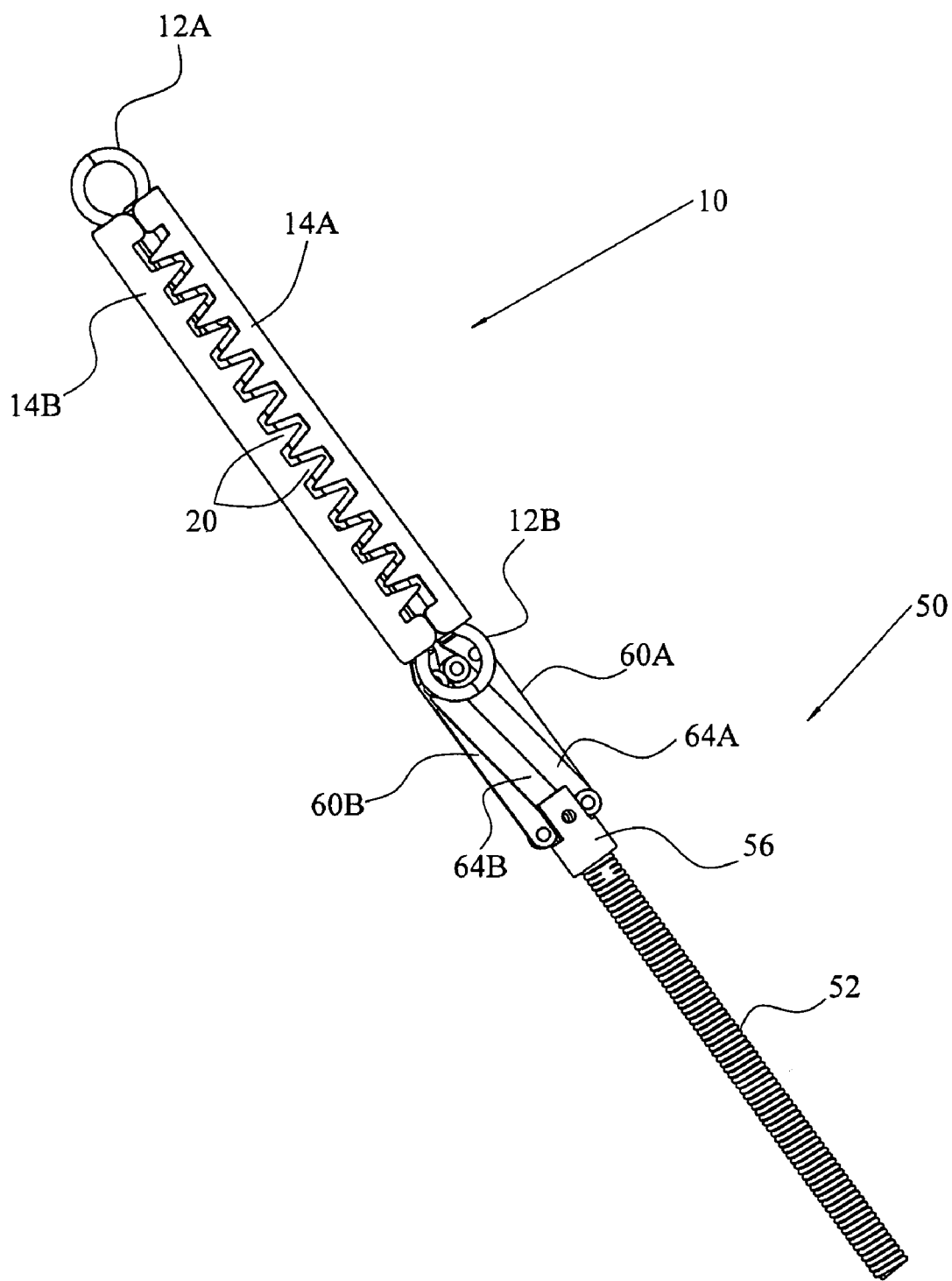
FIG. 12 is an isometric view of the clip applier of FIG. 10, attached to a clip constructed as in FIG. 2, the clip being attached to the applier and in its closed position.
Figure 13:
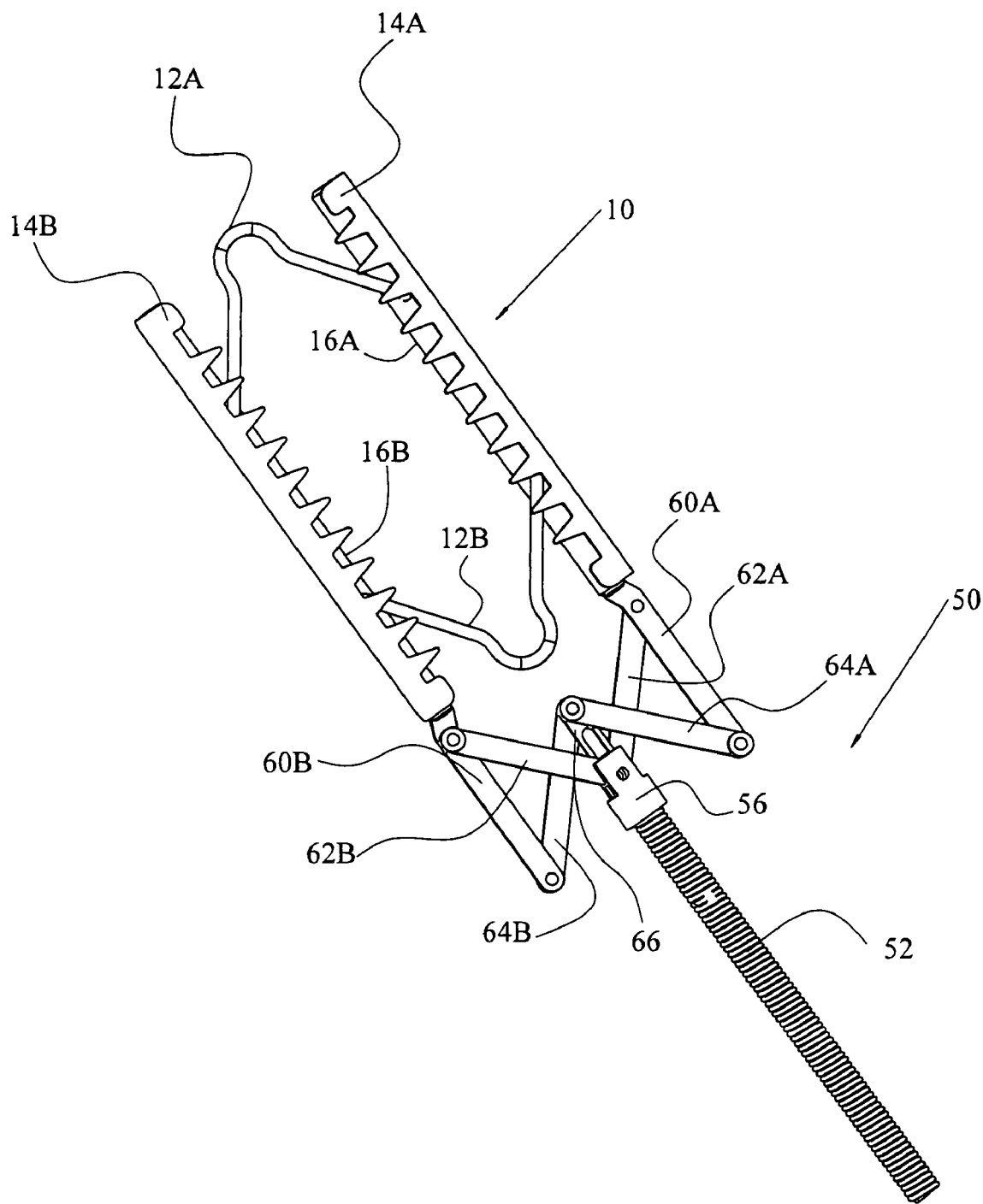
FIG. 13 is an isometric view of the clip applier of FIG. 10, attached to a clip constructed as in FIG. 2, the clip being attached to the applier and in its open position.

Insertion links 60A and 60B each have extensions (not shown) which are positioned on their distal end so that these extensions are insertable into cylindrical elements 58A and 58B. As shown in FIGS. 12 and 13, cylindrical elements 58A and 58B (best seen in FIGS. 10 and 11) are themselves insertable into the ends of compressing elements 16A and 16B of a surgical compression clip similar to clip 10 discussed above in conjunction with FIGS. 2-3B.

Compressing elements 16A and 16B, as shown in FIGS. 2-3B, require a slight modification to be compatible with cylindrical elements 58A and 58B of clip applier 50. To be compatible, at least one of the ends of elements 16A and 16B should be hollow and tubular so that cylindrical elements 58A and 58B of clip applier 50 can be inserted into them.

While in the embodiment shown in FIG. 10 and FIG. 11, cylindrical elements 58A and 58B are separate elements, in other embodiments they may be integrally formed at the ends of insertion links 60A and 60B.

FIGS. 10 and 11 show assembled clip applier 50 in its closed and open positions, respectively. FIGS. 12 and 13 show clip applier 50 inserted into compressing elements 16A and 16B of surgical compression clip 10 when the clip is in its closed and open positions, respectively.

Moving from the open to the closed position of clip applier 50 (or vice versa), and therefore to the open or closed position of clip 10 (or vice versa), can be effected using an operating cable (not shown) joined to, or in other ways in direct communication with, central bar 66 (FIG. 11). The cable passes through spring 52 and out of the proximal end N (FIG. 1A) of the endoscope where it is activated by a user employing an actuator (schematically shown as element 306 of FIG. 1A). The actuator may be any of several types known to those skilled in the art.

Spring 52, in addition to protecting the cable (not shown), serves as a stop sleeve for element 56 while pulling the cable thus enabling the separation of insertion links 60A and 60B. In addition, it allows for greater flexibility of the apparatus as it advances through a lumen of a multi-lumen sleeve (or an endoscopic working channel) from the proximal end of the endoscope toward the suspect lesion near the distal end of the endoscope. Alternatively, the cable can be covered and protected by a flexible tube. The tube may be formed of polytetrafluoroethylene (PTFE), but the choice of this material is exemplary only and it is not intended to be limiting.

To open clip applier 50, central bar 66 is pulled by the operating cable (not shown) in the proximal direction. When that occurs, interconnect links 62A and 62B and 64A and 64B and insertion links 60A and 60B move apart as in FIG. 11 due to the moment exerted on links 64A and 64B. When insertion links 60A and 60B are inserted into clip 10 as in FIG. 12, clip 10 also opens as shown in FIG. 13 because of the force exerted by insertion links 60A and 60B and their attached cylindrical elements 58A and 58B on compressing elements 16A and 16B.

During insertion of clip 10 into a body cavity, the clip is attached to clip applier 50 and both clip 10 and applier 50 are advanced, in their closed positions, through a secondary lumen of a multi-lumen sleeve (or through a working channel) of the endoscope shaft). A tension is maintained in the operating cable (not shown) in order to keep clip 10 attached to clip applier 50 during the entire advance from the proximal end of the secondary lumen (or working channel) to its distal end. The tension in the cable or wire, acts against the force of hinge springs 12A and 12B of clip 10. This creates a force between cylindrical elements 58A and 58B of applier 50 and compressing elements 16A and 16B of clip 10 preventing detachment of clip 10 from applier 50. This force is smaller than the force required to open clip applier 50 and clip 10 attached to it.

To close clip applier 50, the tension in the wire/cable (not shown) passing through spring 52 is released. The force of hinge springs 12A and 12B is passed through compressing elements 16A and 16B to insertion links 60A and 60B. This force applies a moment on links 64A and 64B, which is opposite in direction to the moment exerted when pulling the wire/cable passing through spring 52. When that occurs interconnect links 62A and 62B and 64A and 64B and insertion links 60A and 60B move together as in FIG. 10. When they move together with clip 10 attached as in FIG. 12, compressing elements 16A and 16B also move together as shown in FIG. 12.

While completely releasing the tension in the pull wire allows for the applier to fully return to its original closed position, the tissue pulled and held within clip 10 prevents the clip from following the applier and fully returning to its original closed position. When this occurs, cylindrical elements 58A and 58B easily disengage from clip 10 since the hinge springs' 12A and 12B force is acting essentially on the tissue instead of on the applier.

Figure 14:
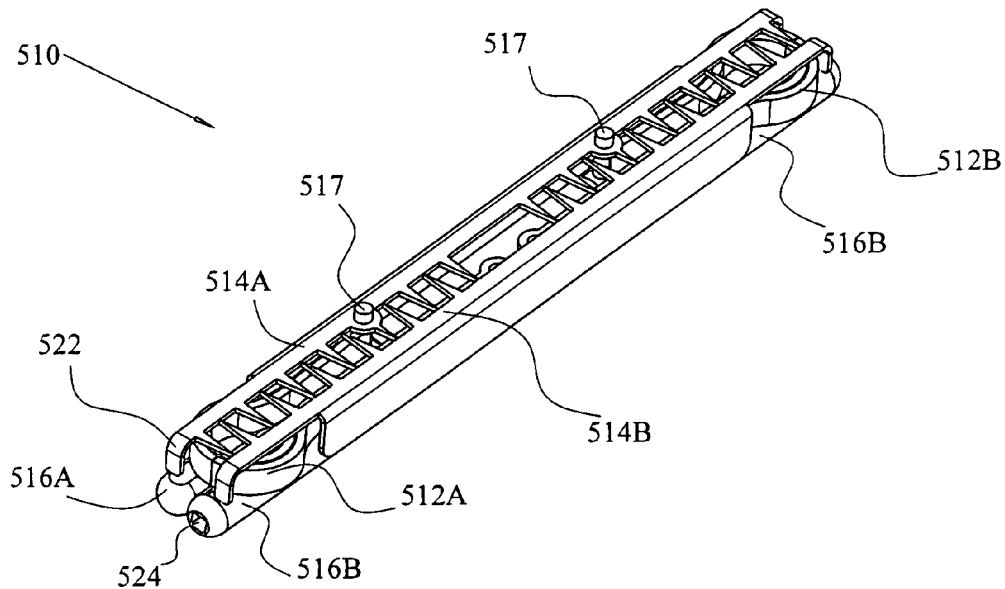
Figure 15:
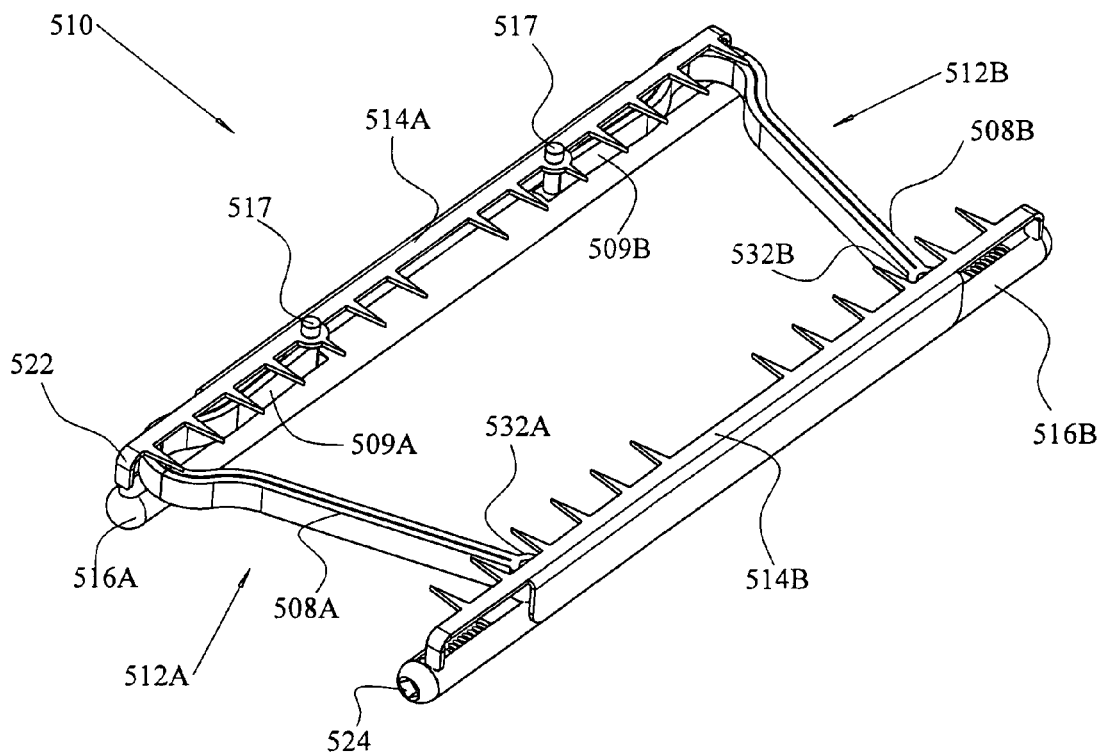
Figure 16:
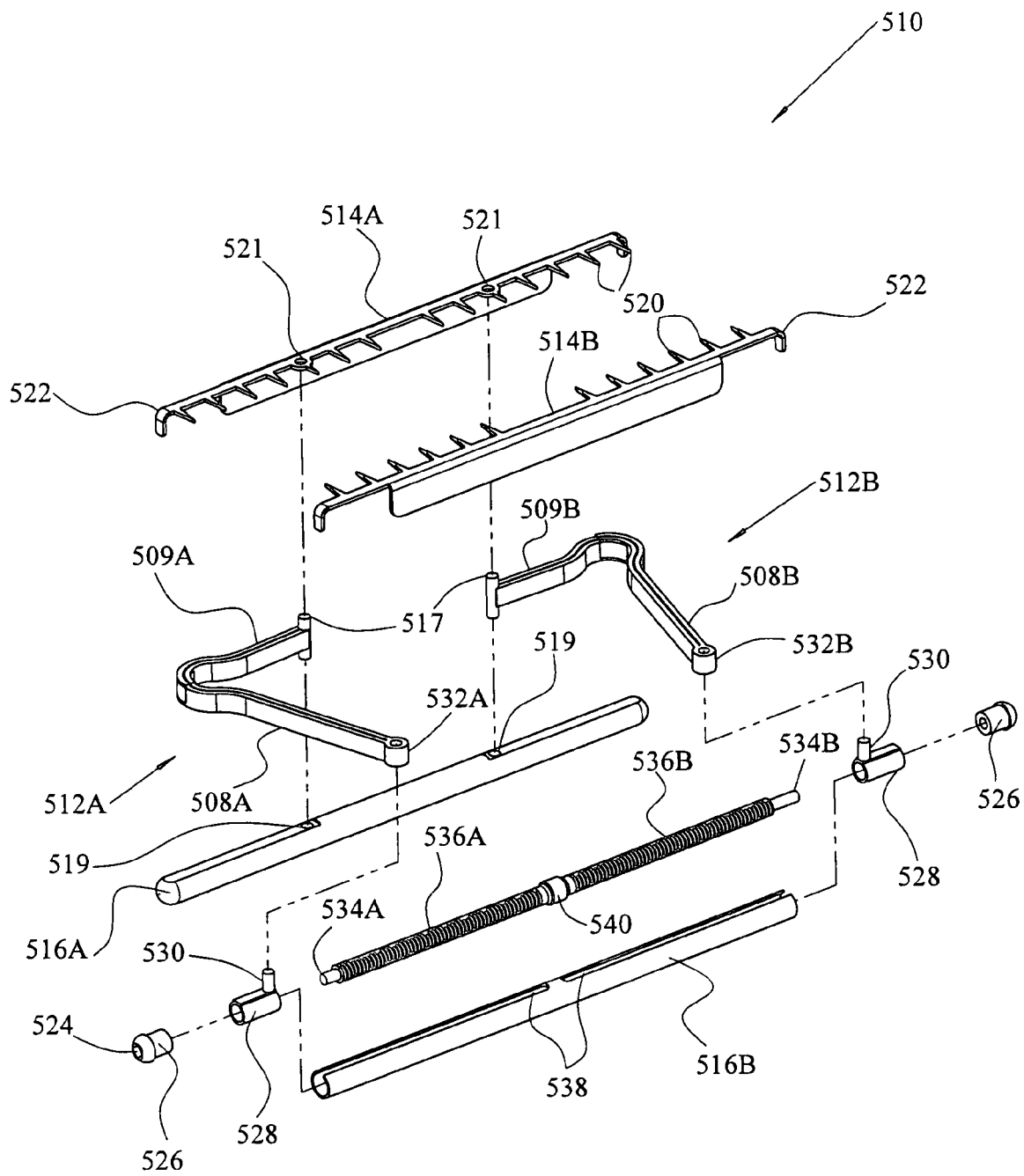
FIG. 16 shows an exploded view of the clip in FIGS. 14 and 15.
Figure 17:
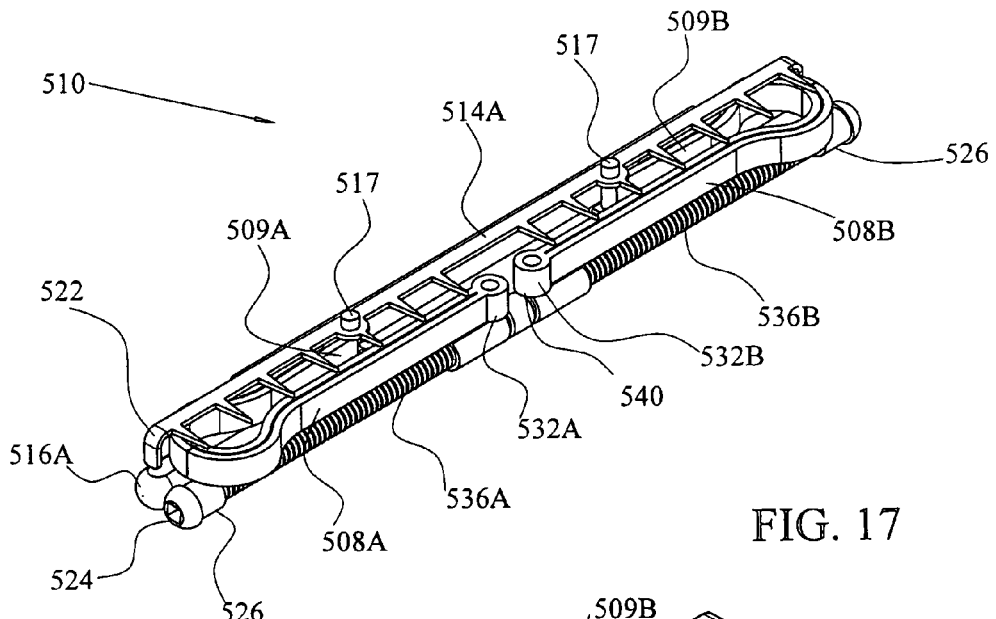
FIGS. 17 and 18 show isometric partially cut-away views of the compression clip shown in FIGS. 14 and 15, respectively.
Figure 18:
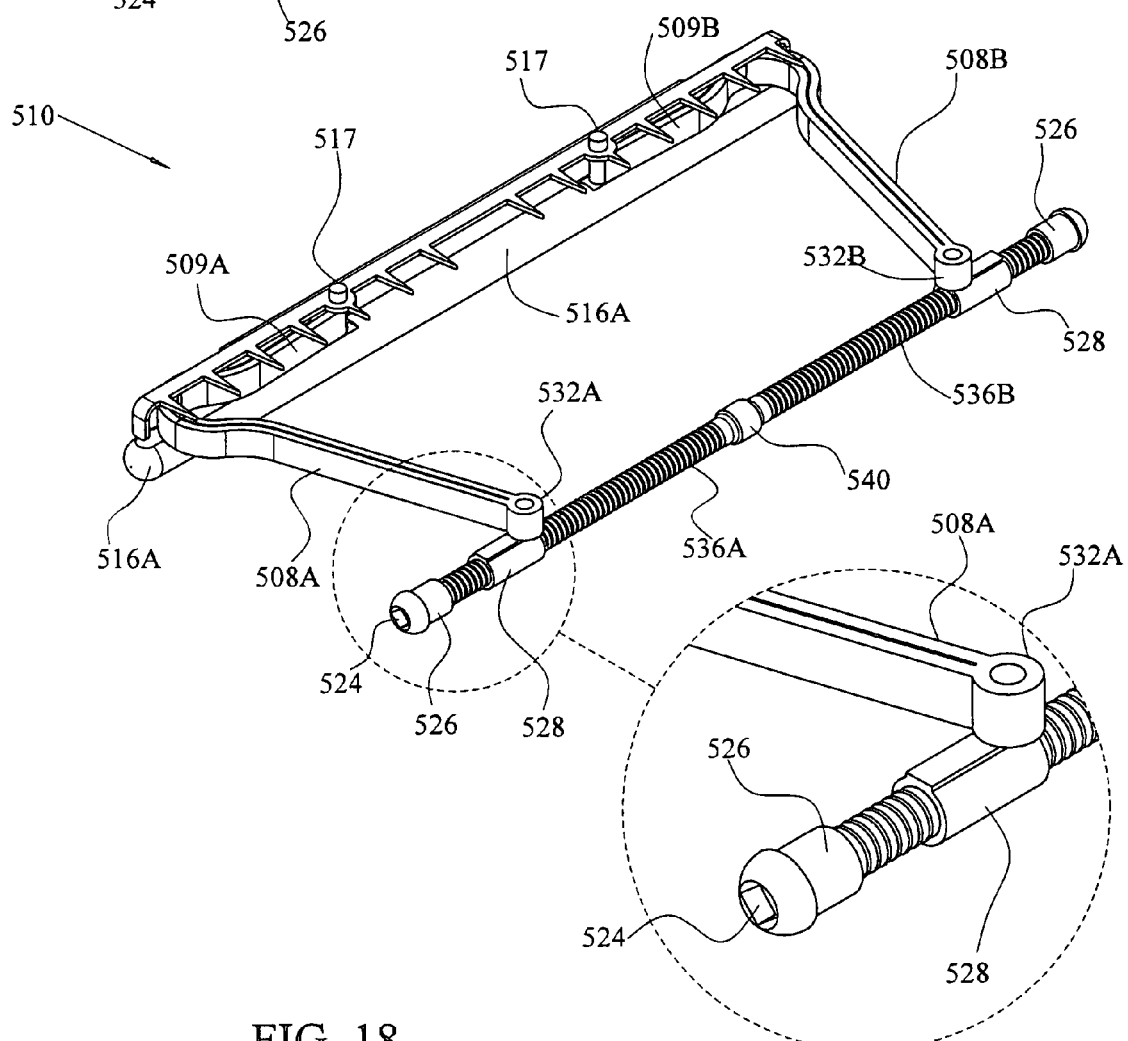

A second embodiment of a compression clip 510 constructed according to the present invention is shown in FIGS. 14-18, to which reference is now made. FIGS. 14 and 15 show clip 510 in its closed and open position, respectively. FIG. 16 is an exploded view of the clip and discussion of the clip will be made in conjunction with that Figure. Most of the elements in FIGS. 14-18 are the same as those discussed in conjunction with the clip embodiments shown in FIGS. 2-3B. Elements that are essentially equivalent in structure and operation will not be discussed again. Only new elements or structural features will be described. Essentially identical or equivalent elements in the embodiments have been numbered as in clips 10 with the addition of 500 as a prefix.

In clip 510, hinge springs 512A and 512B are not symmetrical, each having legs which are of different lengths. Legs 508A and 508B are longer than legs 509A and 509B. Bi-directional connectors 517 are formed at the end of legs 509A and 509B. These connectors formed substantially transversally to the body of clip 510 are sized and configured to be inserted into holes 521 on securing element 514A and holes 519 on compressing element 516A. At the end of legs 508A and 508B are hollow cylinders 532A and 532B insertable over projections 530, more fully described below.

While compressing element 516A is configured essentially as in FIGS. 2-3B, compressing element 516B is a hollow tubular rod with two slots 538 on its surface proximal to securing element 514B. Inside compressing element 516B, a rod, formed of two connected threaded bolts 536A and 536B, is positioned. The length of each threaded bolt is less than half the length of the rod, with the bolts separated by connector means 540. Threaded bolts 536A and 536B each have different "handedness", that is thread direction. Because the two threaded bolts have different "handedness" they separate when turned in one direction and come closer together when turned in the opposite direction.

Over the ends of threaded bolts 536A and 536B are fitted cylindrical elements 528, the latter having complementary threads on their inner surface. Threaded bolts 536A and 536B have an attachment means 534A and 534B on their ends for insertion and joining with cylindrical elements 528. Cylindrical elements 528 are each formed with a projection 530 protruding substantially transversally to the long axis of cylindrical elements 528. Projections 530 pass through slots 538 preventing fitted cylindrical elements 528 from turning as threaded bolts 536A and 536B are turned. This forces cylinders 528 to move linearly along the long axis of compression element 516B. The threaded rod with cylinders 528 are held to compressing element 516B by plugs 526. Plug 526 on one side of the rod, the proximal side, includes a recess 524, typically, but without being limiting, a square recess, which is configured to receive a screw rotation apparatus (not shown). Projections 530 on cylindrical elements 528 are configured and sized to be inserted into hollow cylinders 532A and 532B formed on the longer legs 508A and 508B of springs 512A and 512B. The placement of legs 508A and 508B of hinge springs 512A and 512B and the relationship between plugs 526, cylindrical elements 528 and threaded bolts 536A and 536B (which when joined form the threaded rod discussed above) are best seen in FIGS. 17 and 18.

Figure 19:
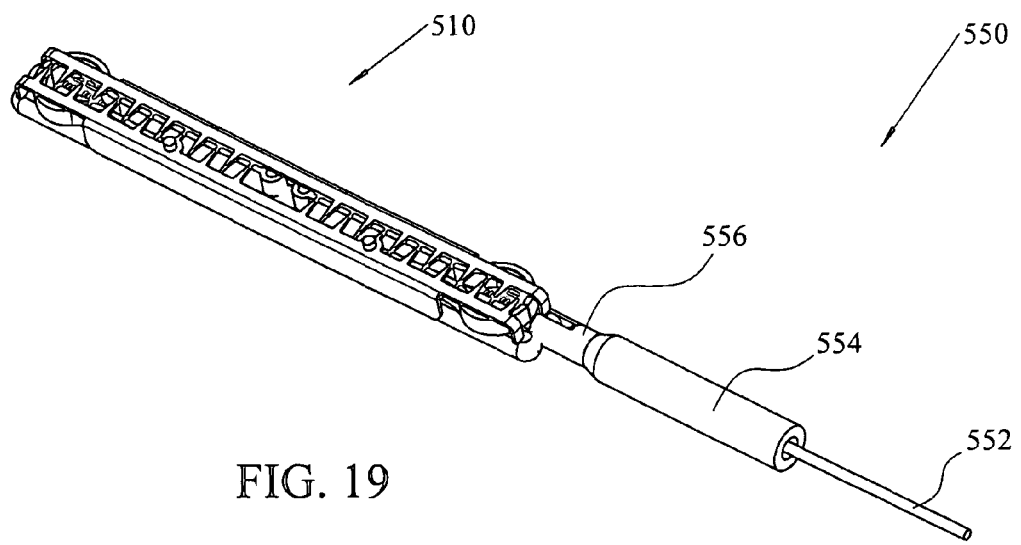
FIGS. 19 and 20 show isometric views of a clip applier used with the clip shown in FIGS. 14-18, FIG. 19 showing the applier engaged to the clip and FIG. 20 disengaged from the clip.
Figure 20:
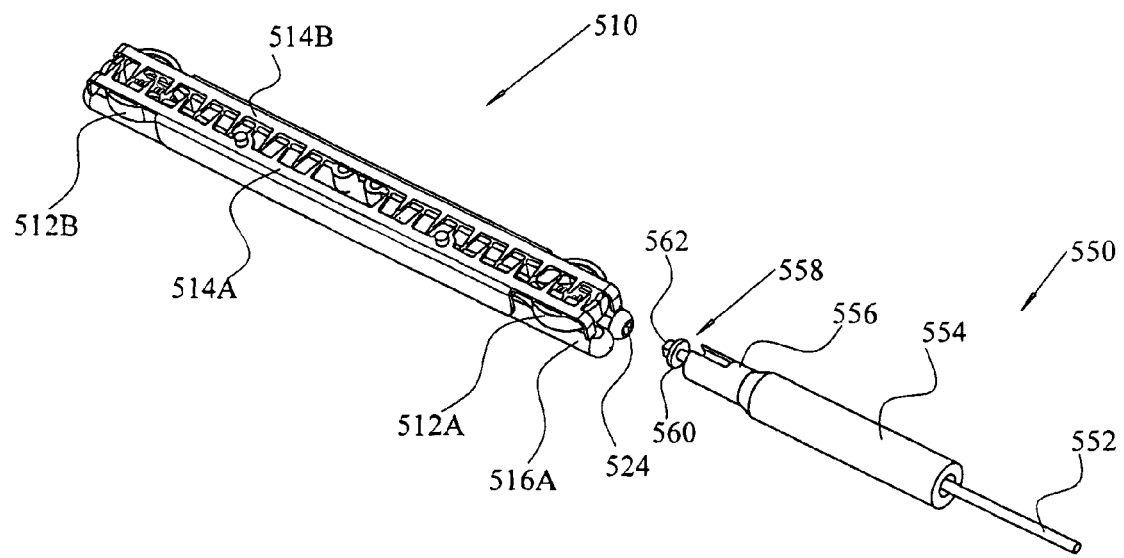

Reference is now made to FIGS. 19-23 which show a clip applier 550 that can be used to operate clip 510, the latter described in conjunction with FIGS. 14-18. FIGS. 19 and 20 show clip applier 550 in its engaged and disengaged position, respectively, with clip 510.

Figure 21:
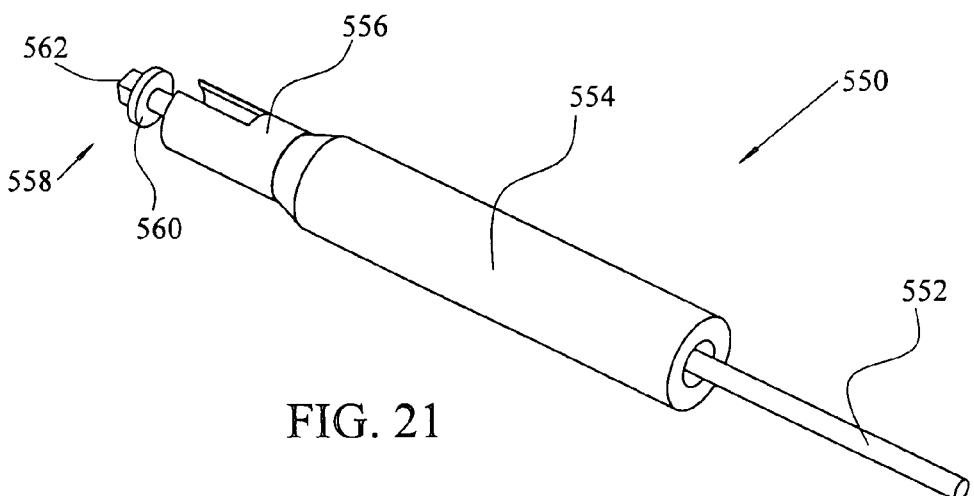
FIG. 21 shows an isometric view of the applier in FIGS. 19 and 20.
Figure 22:
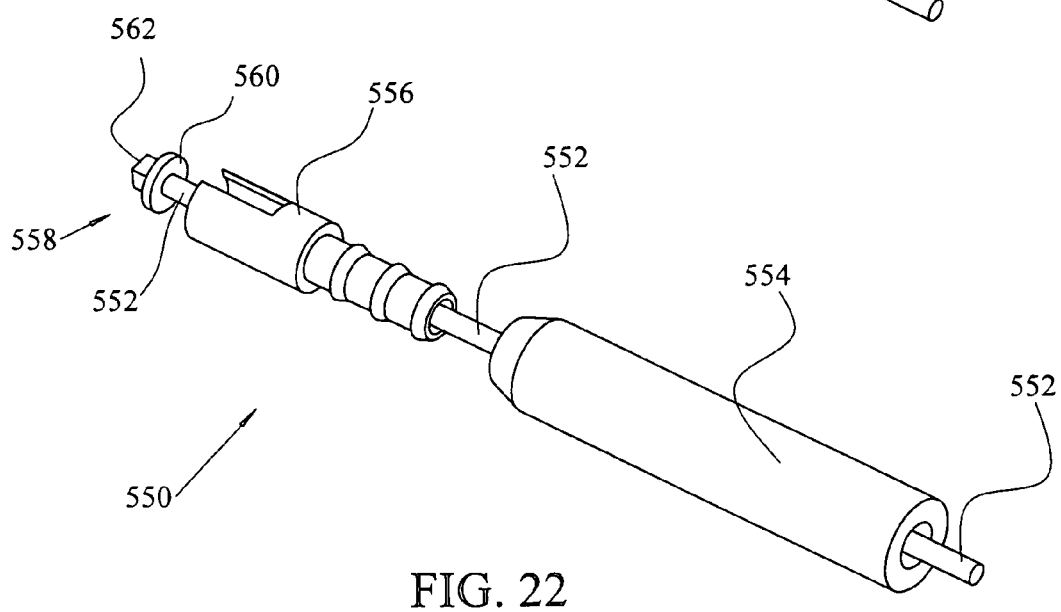
FIG. 22 shows a partially exploded view of the applier in FIGS. 19 and 20.
Figure 23:
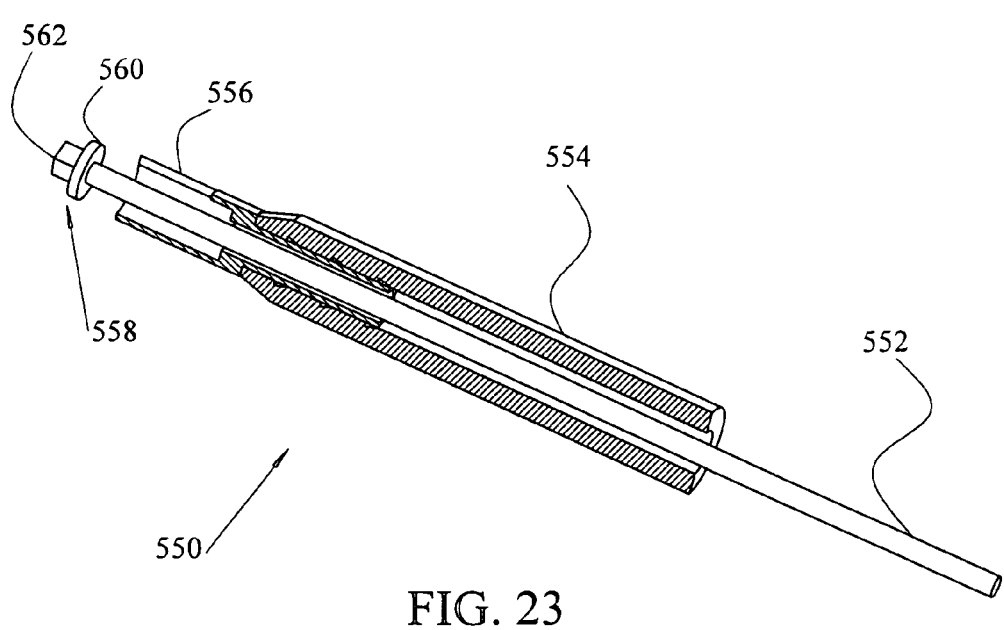
FIG. 23 shows a cross-sectional view of the applier shown in FIGS. 19 and 20.

The structure and operation of clip applier 550 can best be understood by viewing FIGS. 21-23. A cable 552 capable of being rotated is extended through a tube 554, typically a flexible plastic tube capable of advancing the clip to the distal end of an endoscope. Cable 552 ends at rotation head 558 which includes a washer element 560 and a male element 562, the latter sized and configured for insertion into recess 524 of clip 510 (FIGS. 14-18).

In some embodiments, tube 554 may be a spring having sufficient flexibility to advance a clip attached to applier 550 past the distal end of the endoscope.

Clip 510, for example, is inserted into a cup 556 of clip applier 550. Cup 556 typically is made of plastic or metal. Plug 526 with recess 524 (FIGS. 14-18) is positioned proximate to applier 550. Male element 562 is inserted into recess 524 of clip 510. Recess 524 and male element 562 are configured to be mateable. Moving clip 510 forward or backward is effected by pushing or pulling cable 552. Rotating cable 552 opens and closes the clip depending on the direction of rotation and the sequence of the bolts and the "handedness" of the threaded bolt proximate to male element 562.

Pushing forward releases clip 510 from applier 550. First, washer element 560 pushes clip 510 out of cup 556. Then, by pulling cable 552 towards the proximal end of the endoscope, male element 562 is released from recess 524 of clip 510, thereby fully releasing the clip from the applier.

Figure 24A:
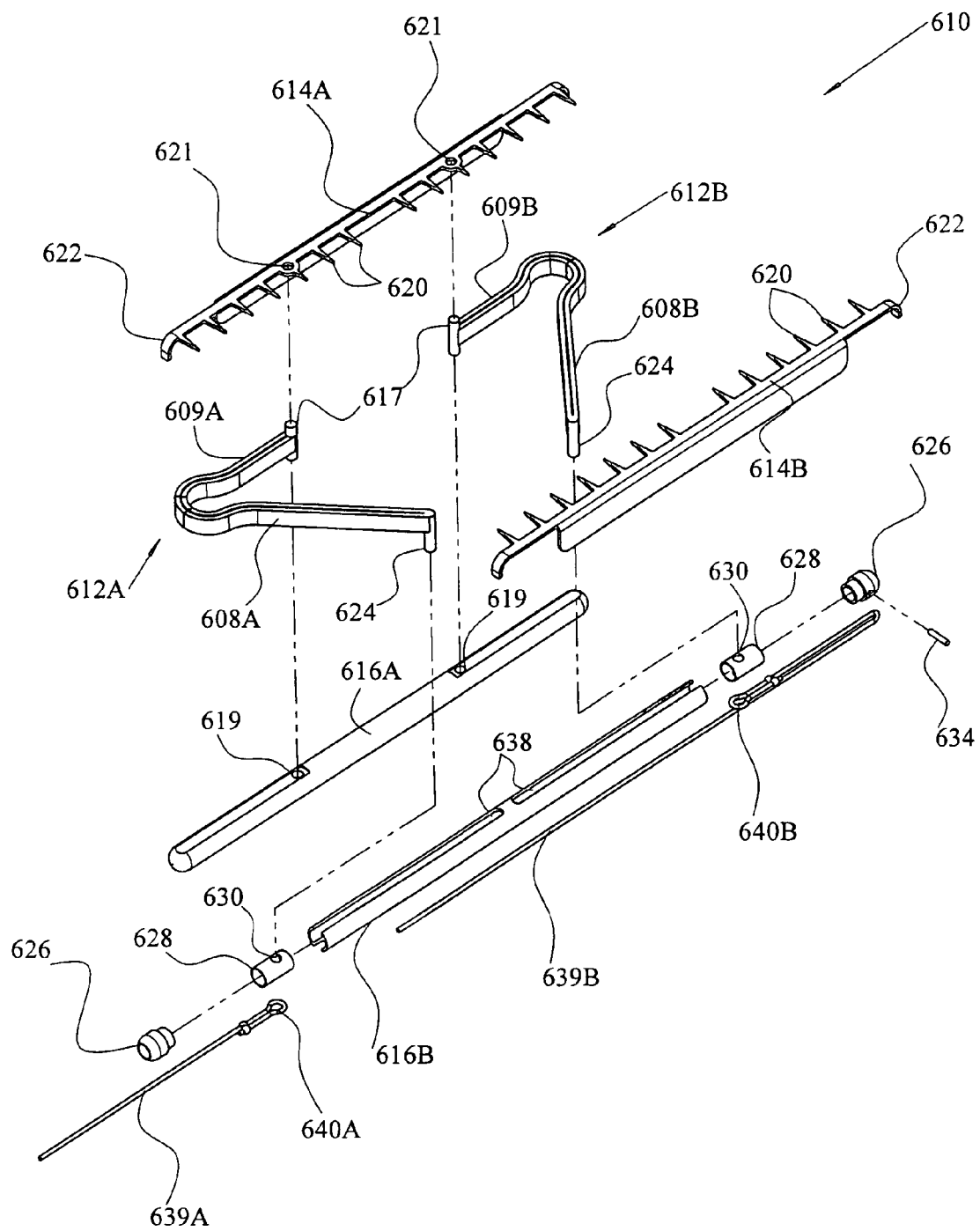
FIG. 24A shows an exploded view of a third embodiment of a compression clip constructed according to the present invention.
Figure 24B:
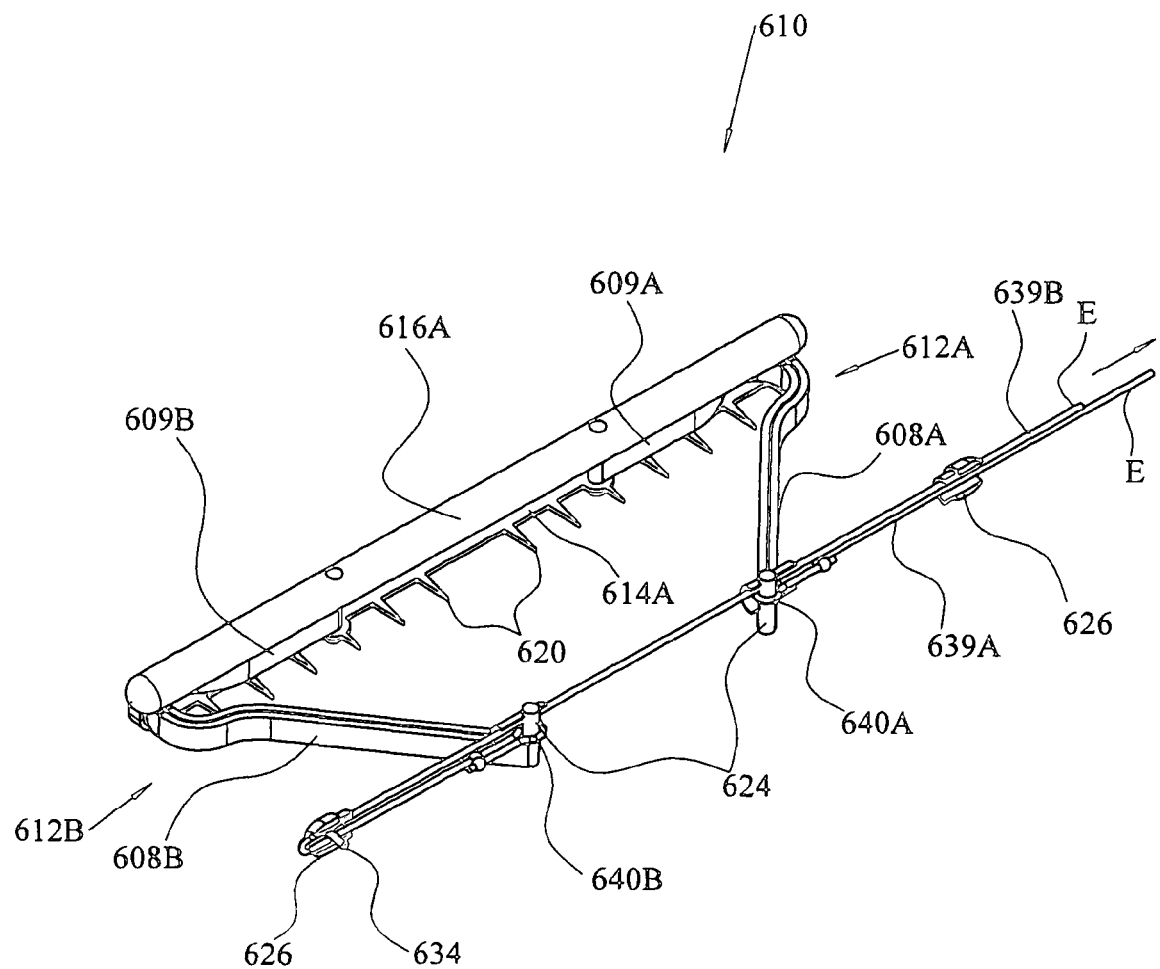
FIG. 24B shows an isometric partially cut-away view of the clip shown in FIG. 24A.

A third embodiment of a compression clip constructed according to the present invention is shown in FIGS. 24A and 24B, to which reference is now made.

From FIG. 24A, which shows an exploded view of clip 610, it is readily apparent that many of the elements presented there have been encountered and described previously in conjunction with previously discussed embodiments of compression clips constructed according to the present invention. Accordingly, elements that are structurally and operationally similar to previously described elements will not be described again here. Essentially identical or equivalent elements to those found in clips 10 and 510 have been numbered as in clips 10 and 510 with the prefix 600.

Securing and compressing elements 614A, 614B and 616A, 616B, respectively, are essentially the same as in clip 510. Hinge springs 612A and 612B are unsymmetrical as in clip 510. Again, there is a bi-directional connector 617 on the shorter legs 609A and 609B of hinge springs 612A and 612B which are inserted into holes 621 in securing element 614A and holes 619 on compressing element 616A. Compressing element 616B is again a hollow tubular member with two slots 638. The longer legs 608A and 608B of hinge springs 612A and 612B include unidirectional connectors 624 at their ends which extend in the direction of compressing element 616B allowing for insertion into preformed holes 630 of cylindrical elements 628, to be discussed below.

Cylindrical elements 628, formed with holes 630, are insertable into and retained in hollow tubular compressing element 616B. Holes 630 of cylindrical elements 628 act as receiving recesses for connectors 624 of springs 612A and 612B. When connectors 624 are inserted into holes 630 they are movable in slots 638 and do so with the opening and closing of springs 612A and 612B. Tubular compressing element 616B is capped by plugs 626. The plug 626 distal to the user has a hole into which pin 634 is inserted.

Passing through tubular compressing member 616B are wires 639A and 639B. These wires have loops 640A and 640B at their ends configured to fit over connectors 624.

Upon viewing FIG. 24B, the arrangement of the various elements of clip 610 and their operation becomes evident. In FIG. 24B, clip 610 has been flipped vis-a-vis the view shown in FIG. 24A and compressing element 616B and securing element 614B are not presented. By pulling the ends E of wires 639A and 639B in the direction of the arrow shown, legs 608A and 608B of springs 612A and 612B separate as do securing elements 614A and 614B (the latter not shown) and compressing elements 616A and 616B (the latter not shown). One of the wires in the Figure, wire 639B, passes around pin 634 when pulled. When wires 639A and 639B are released, or pushed in a direction opposite to that shown by the arrow, the clip's elements—its securing elements, compressing elements, and the legs of its springs—move to a position adjacent to each other with the tissue to be resected held between the securing and compressing elements.

After severance of the suspect tissue is effected, excess wire is cut and withdrawn from the endoscope and body.

A fourth embodiment of a surgical compression clip constructed according to the present invention is shown in FIGS. 25A-26B, to which reference is now made.

This embodiment is very similar to the embodiment shown in FIGS. 2-3B and elements are numbered similarly with the inclusion of a prefix digit 7. Similar elements are constructed and operative as in the embodiment presented in FIGS. 2-3B and, accordingly, will not be discussed again.

The present embodiment is different from the embodiment of FIGS. 2-3B in that the bi-directional hinge spring connectors 717 are now joined on the inside of hinge spring arms 708 of spring elements 712A and 712B (best seen in FIG. 4C) and not at the ends of hinge spring arms 8 of hinge spring elements 12A and 12B as in FIGS. 2-3B and FIGS. 4A and 4B. Additionally, and as a direct result of the new positioning of hinge spring connectors 717, spaces 725 must be formed in lateral walls 727 of securing elements 714A and 714B. These spaces are absent in walls 27 of securing elements 14A and 14B as seen and labeled in FIG. 3B. Its necessity with the present clip embodiment is readily seen in FIGS. 25A, 25B, 26A and 26B where hinge spring arms project, at least partially, through spaces 725. It should be noted that securing elements 714A and 714B may be a single integral structure or elements made from several parts joined together by any process known to those skilled in the art, such as by welding. This is true as well for the securing elements shown in previous embodiments and discussed elsewhere herein.

The positioning of connectors 717 on the inside of arms 708 of hinge spring elements 712A and 712B effectively creates a preload that allows the clip to open wider while still applying the forces needed for the necrotic process. An alternative, or additional, technique to achieve preloading is to heat hinge spring elements 712A and 712B and shape them during manufacture.

Figure 25A:
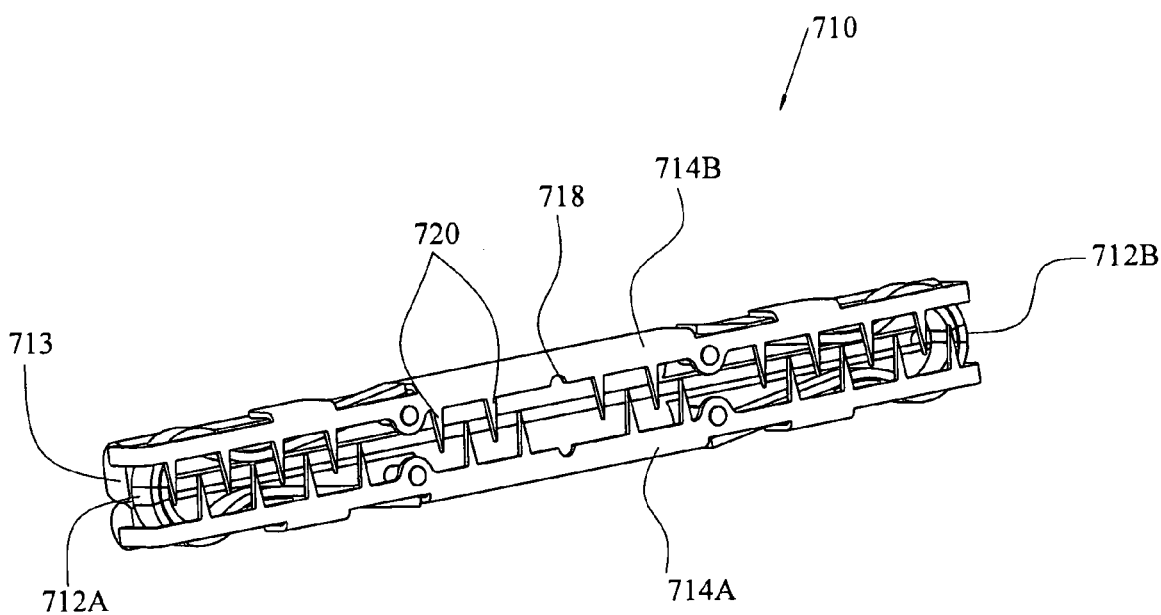
FIGS. 25A and 25B are an isometric top and bottom view of a clip constructed according to a fourth embodiment of the present invention, the clip being in its closed position.
Figure 25B:
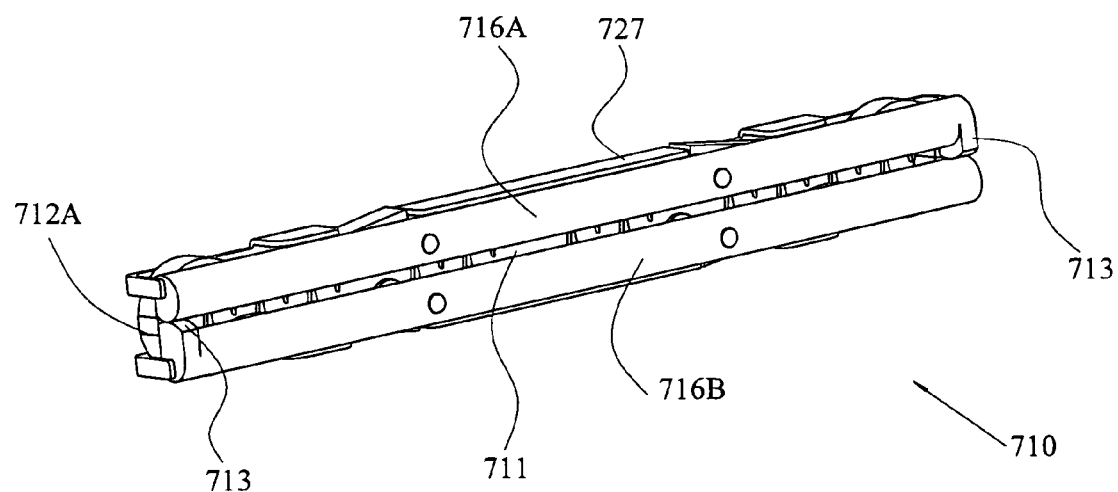

As best seen in FIGS. 25A and 25B, top and bottom views respectively of clip 710, hinge spring elements 712A and 712B exert a force on compressing elements 716A and 716B even when clip 710 is in its closed position.

Clip 710 is effectively preloaded and a gap 711 (best seen in FIG. 25B) exists between securing elements 714A and 714B even when clip 710 is in its closed position. This gap typically, but without intending to be limiting, is in the range of 0.7 to 0.9 mm, which ensures that the force exerted by clip 710 falls to zero before it has a chance to cut through the healing tissue. It should be remembered that when the necrotic process is in an advanced stage, tissue thickness is reduced significantly.

Gap 711, can be formed in one of many ways. Without intending to be limiting, one of these ways is by forming gap forming projections 713 (best seen in FIGS. 25B, 26A and 26B) at the end of one or both ends of compressing elements 716A and 716B.

Figure 27A:
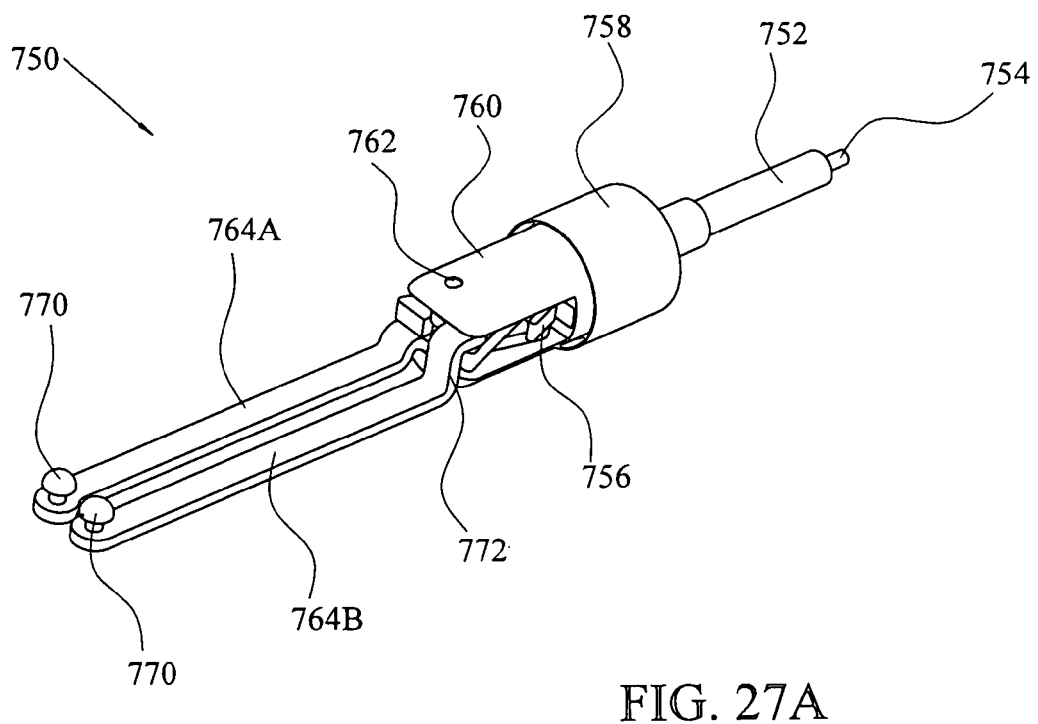
FIGS. 27A and 27B are isometric views of a clip applier constructed according to another embodiment of the present invention, the applier shown in its closed and open position, respectively.
Figure 27B:
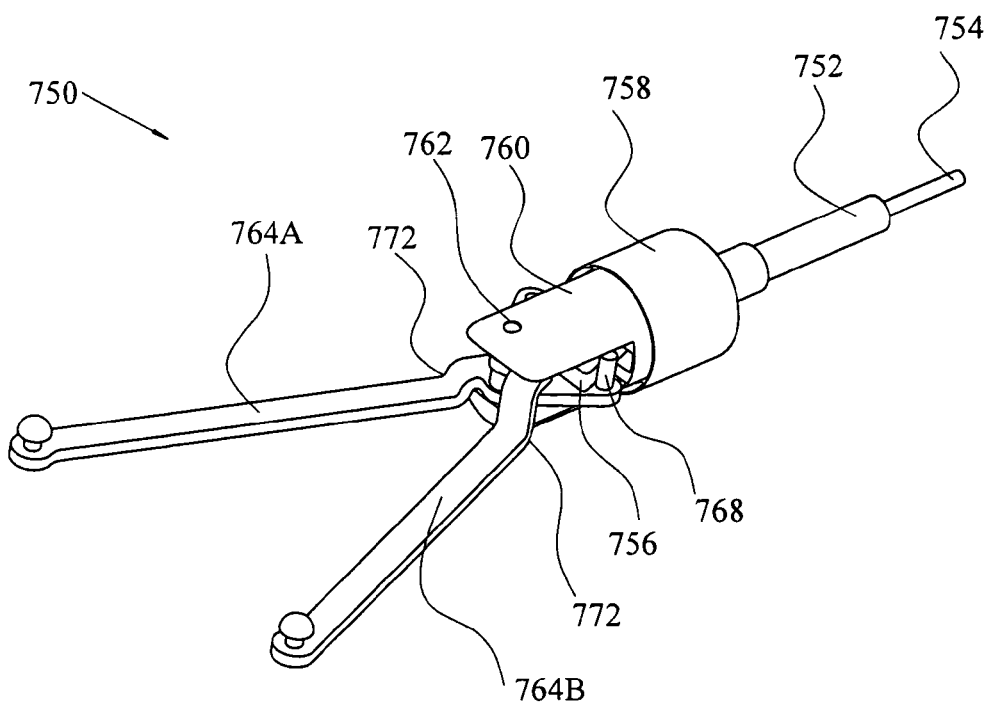
Figure 27C:
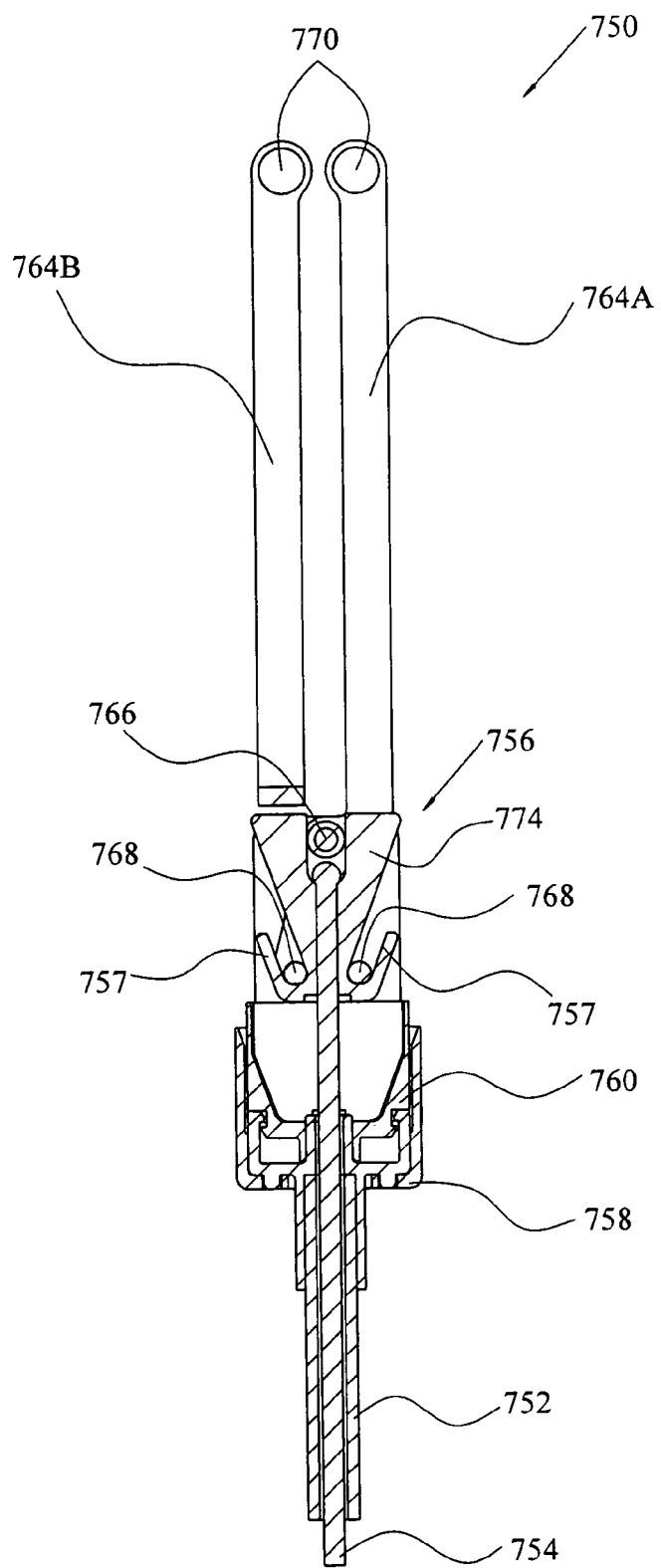
FIGS. 27C and 27D are cross-sectional views of the clip applier shown in FIGS. 27A and 27B, the applier shown in its closed and open position, respectively.
Figure 27D:
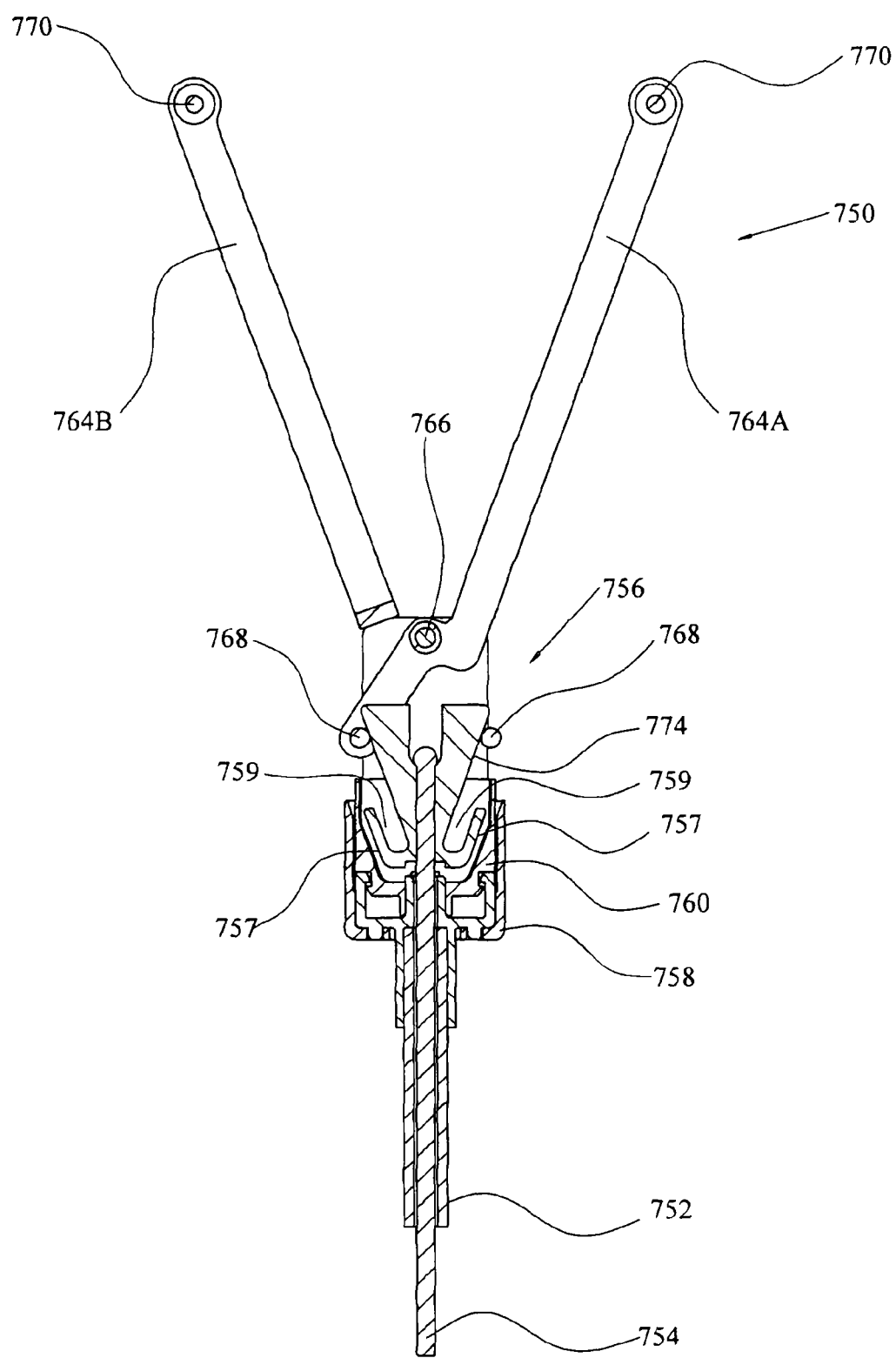
Figure 28A:
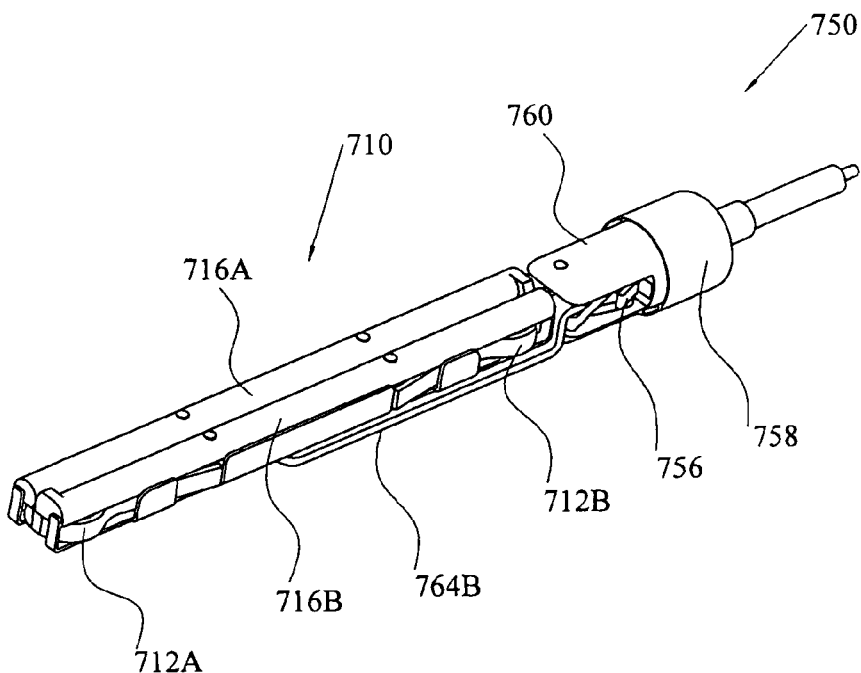
FIGS. 28A and 28B are isometric views of the clip applier shown in FIGS. 27A and 27B constructed in its closed and open position, respectively, when attached to and operating the clip shown in FIGS. 25A-26B.
Figure 28B:
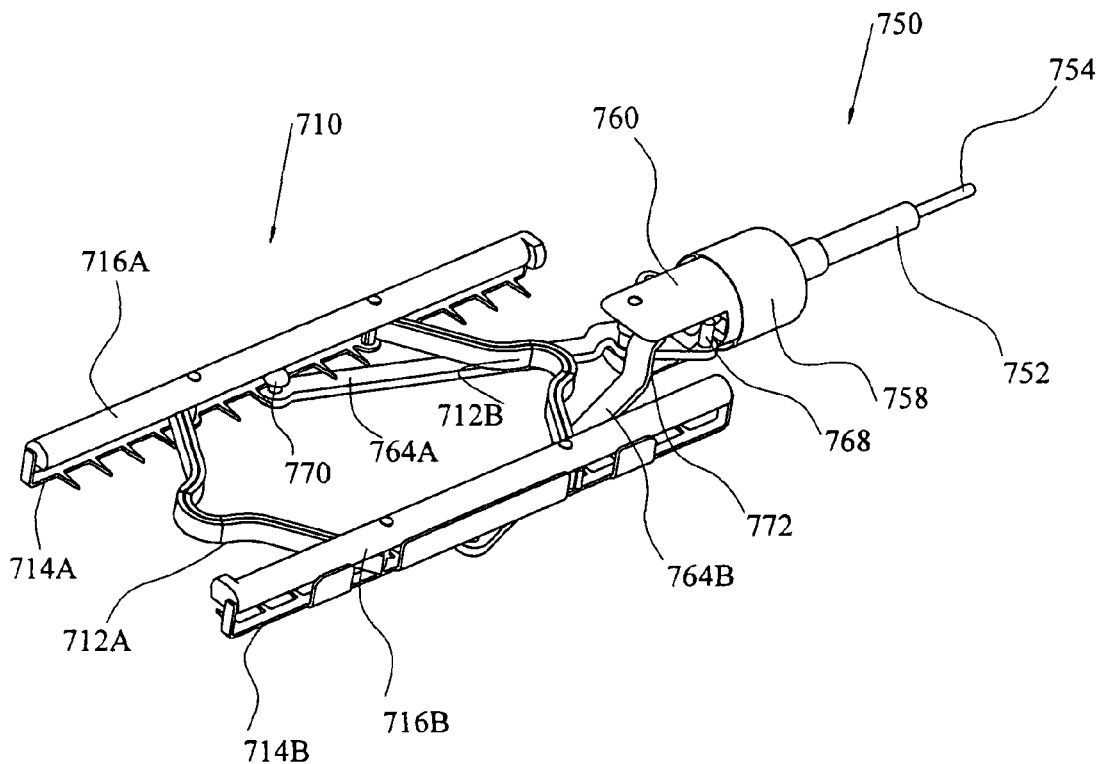

An embodiment of a clip applier 750 that can be used with clip 710 of FIGS. 25A-26B is shown in FIGS. 27A-28B. While discussed in terms of its use with the clip shown in FIGS. 25A-26B, it should readily be understood that applier 750, with little or no modification, may be used with other clip embodiments discussed above. FIGS. 27A and 27B are isometric views of clip applier 750, the applier shown in its closed and open position, respectively. FIGS. 27C and 27D are cross-sectional views of the applier in FIGS. 27A and 27B, respectively. FIGS. 28A and 28B are isometric views of the clip applier shown in FIGS. 27A-27B in its closed and open position, respectively, when attached to and operating the clip shown in FIGS. 25A-26B.

FIGS. 27A-27D, to which reference is now made, shows a wire or cable 754 encased in a sheath 752 which extends toward, and exits from, the body cavity so that it can be operated by a user. Wire (or cable) 754 is attached to a cam 756 which is positioned inside applier body 760, the later covered by applier body cover 758. Applier body 760 at its distal end includes a hole 762 on each of two opposing walls. Applier 750 includes two arms 764A and 764B each having a projection 768 at their proximal end and attachment projections 770 at their distal end. Attachment projections 770 attach to clip 710 (FIG. 25A) at its indentations 718 (FIG. 25A). Arms 764A and 764B each have an aperture (not shown) to receive a pin 766 (FIGS. 27C and 27D) which also passes through holes 762 of applier body 760. Pin 766 serves as an axis around which arms 764A and 764B rotate. Arms 764A and 764B each have a bend 772 in them which allows the positioning of projections 768 on arms 774 of cam 756.

Referring now to FIG. 27C, applier 750 is shown in its closed position. Wire or cable 754 has been pushed in the distal direction, i.e. away from the user, causing attached cam 756 to also move in the distal direction within applier body 760. Due to the force applied by open clip 710 on applier arms 764A and 764B, projections 768 of arms 764A and 764B rotate towards each other around pin 766, towards the center and into the space 759, best seen in FIG. 27D. Space 759 is formed between cam arms 774 and cam flanges 757. This results in applier arms 764A and 764B moving to a position where they are adjacent to each other. When applier arms 764A and 764B are brought together, clip 710 is brought to its closed position as best seen in FIG. 28A.

Referring now to FIG. 27D, applier 750 is shown in its open position. Wire 754 has been pulled in the proximal direction, i.e. toward the user, causing attached cam 756 to also move in the proximal direction in applier body 760. This forces projections 768 of applier arms 764A and 764B to rotate in the outward direction. This causes applier arms 764A and 764B to move to a position where they are spaced apart from each other and where projections 768 of applier arms 764A and 764B are pushed and held apart by the wider distal portion of cam arms 774. When arms 764A and 764B separate from each other as just described, clip 710 is brought to its open position as best seen in FIG. 28B.

Figure 29:
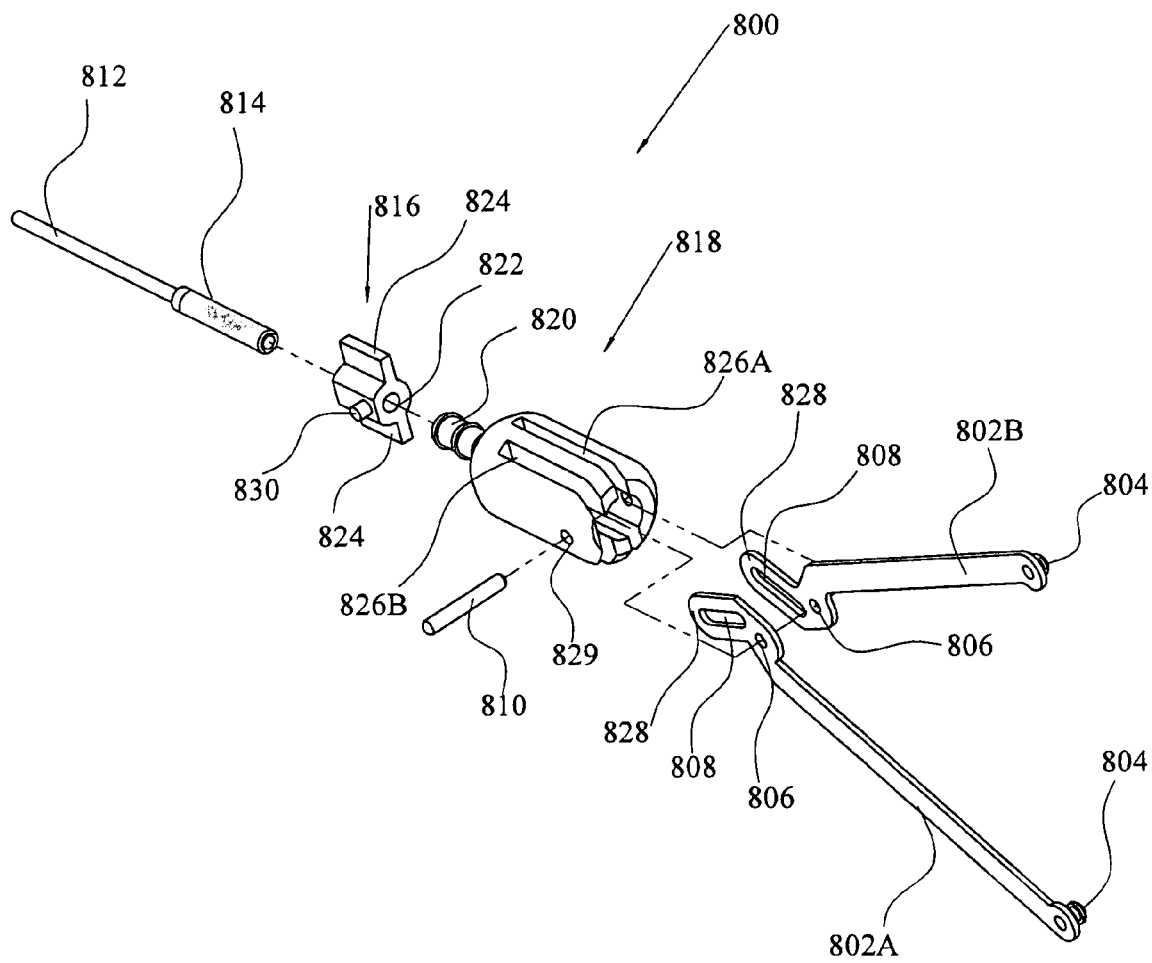
FIG. 29 is an exploded view of another embodiment of a clip applier for use with the clips in the specification herein.
Figure 30A:
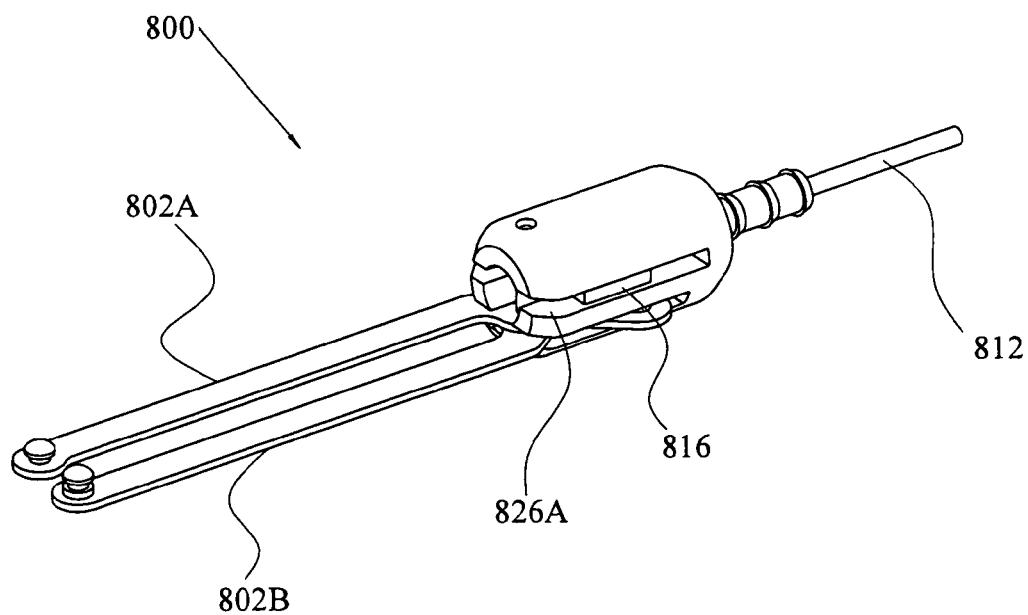
FIGS. 30A and 30B are isometric views of the clip applier shown in FIG. 29 in its closed and open position, respectively.
Figure 30B:
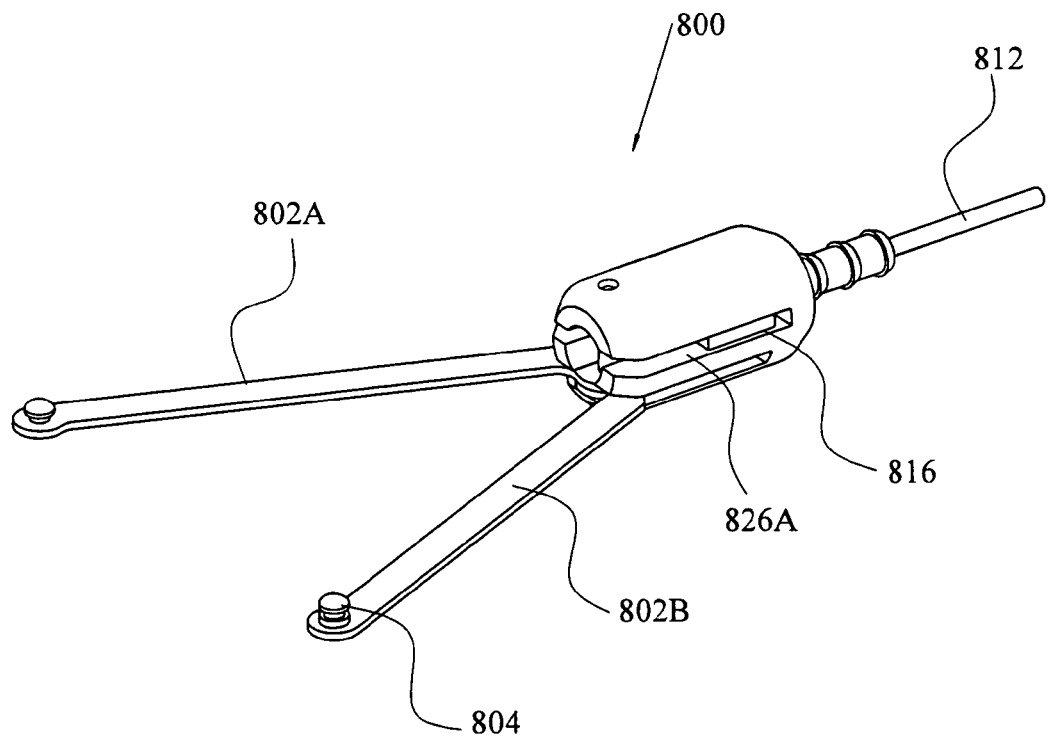
Figure 30C:
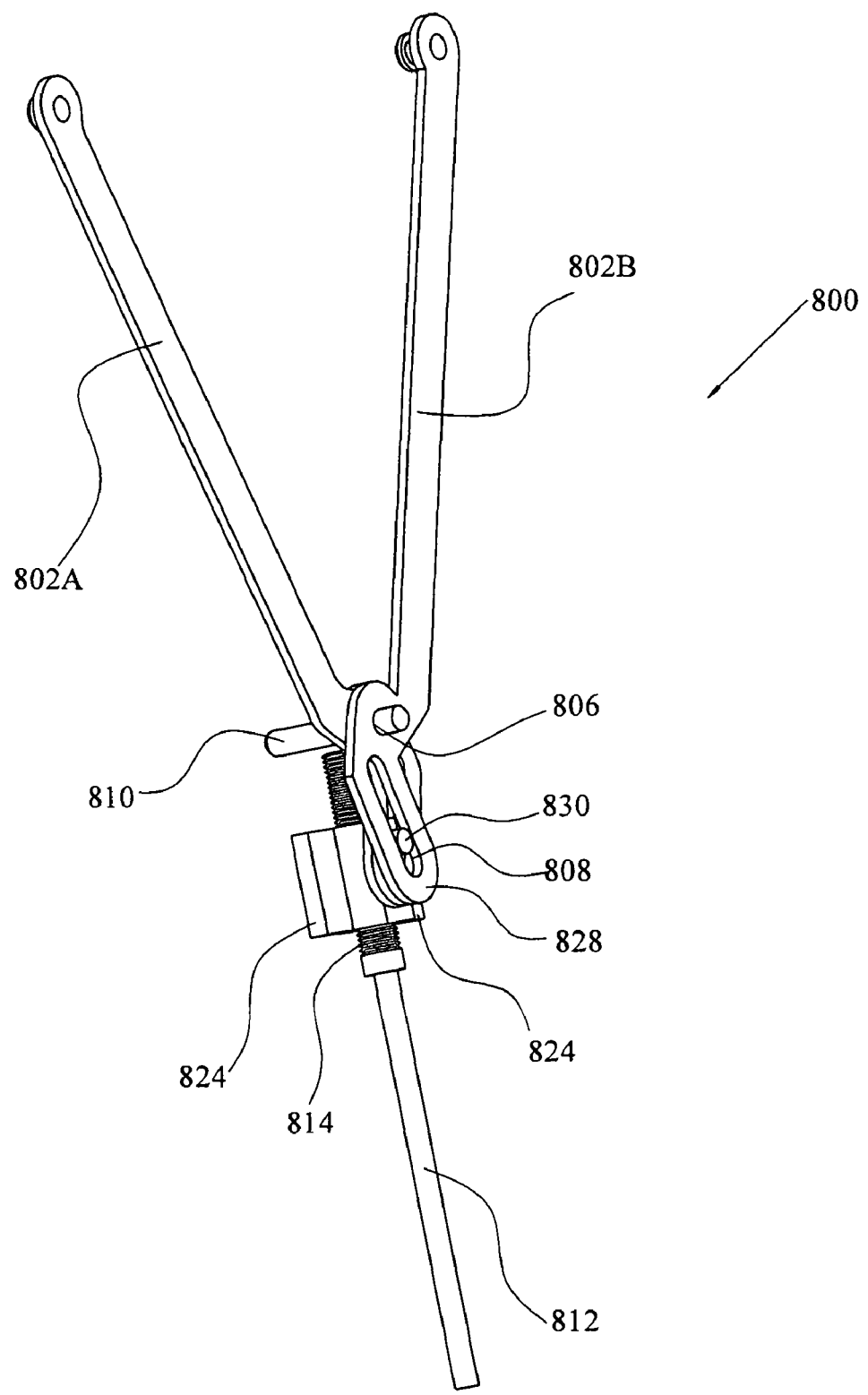
FIG. 30C is a revealed inner view of FIG. 30B.

FIG. 29 through FIG. 30C, to which reference is now made, show various views of another embodiment of a clip applier 800 which may be used with many of the surgical clips discussed herein. FIG. 29 is an exploded view of clip applier 800. FIGS. 30A and 30B are isometric views of clip applier 800 shown in FIG. 29 in its closed and open position, respectively. FIG. 30C is an inner, totally cut-away view of FIG. 30B.

In FIG. 29, there is a wire or cable 812 with a threaded end 814. Wire or cable 812 extends to and exits from the body cavity so that it can be operated by a user. Threaded end 814 of wire or cable 812 is inserted into jagged entry 820 of applier body 818. A casing (not shown) of wire or cable 812 is caught on the jagged surface of entry 820. The threaded end 814 of wire or cable 812 is threaded into a threaded bolt 822 of configuration controller 816 when controller 816 is positioned in guide slot 826A (discussed below) of applier body 818. Configuration controller 816 is formed to also include two wing elements 824 and a projection 830.

Applier body 818 includes a first and a second guide slot 826A and 826B, respectively, and configuration controller 816 is positioned so that it rides in first guide slot 826A. Wing elements 824 of configuration controller 816 move freely in first guide slot 826A. Proximal ends 828 of applier arms 802A and 802B are positioned in and move in second guide slot 826B.

Applier arms 802A and 802B each include an attachment projection 804, a hole 806 and an arm guide slot 808. Projection 804 connects to the surgical clips in a manner similar to that shown elsewhere herein. When the proximal ends 828 of applier arms 802A and 802B are inserted in second guide slot 826B, a pin 810 is inserted through hole 829 of applier body 818 and through holes 806 in applier arms 802A and 802B. This pin acts as an axis of rotation when arms 802A and 802B are brought proximate to or spaced apart from each other. When arms 802A and 802B are inserted into guide slot 826B, projection 830 of configuration controller 816 passes through arm guide slots 808 of applier arms 802A and 802B.

Now referring additionally to FIGS. 30A and 30B, when wire or cable 812 is rotated in one direction configuration controller 816 advances in the distal direction of guide slot 826A with projection 830 (FIG. 29) moving towards the distal end of arm slots 808 (FIG. 29). This causes applier arms 802A and 802B to rotate towards each other and attain their closed position. When wire or cable 812 is rotated in the other direction, configuration controller 816 moves in the proximal direction in guide slot 826A and projection 830 moves towards the proximal end of arm slots 808 causing applier arms 802A and 802B to rotate away from each other and attain their open position (FIGS. 30B and 30C). Wing elements 824 of configuration controller 816 prevent turning of controller 816 when rotated by the threaded end 814 (FIG. 29) of wire/cable 812, thereby allowing for the conversion of rotational motion into translational motion.

A fifth embodiment of a surgical compression clip constructed according to the present invention is shown in FIGS. 31A-44, to which reference is now made.

Figure 31A:
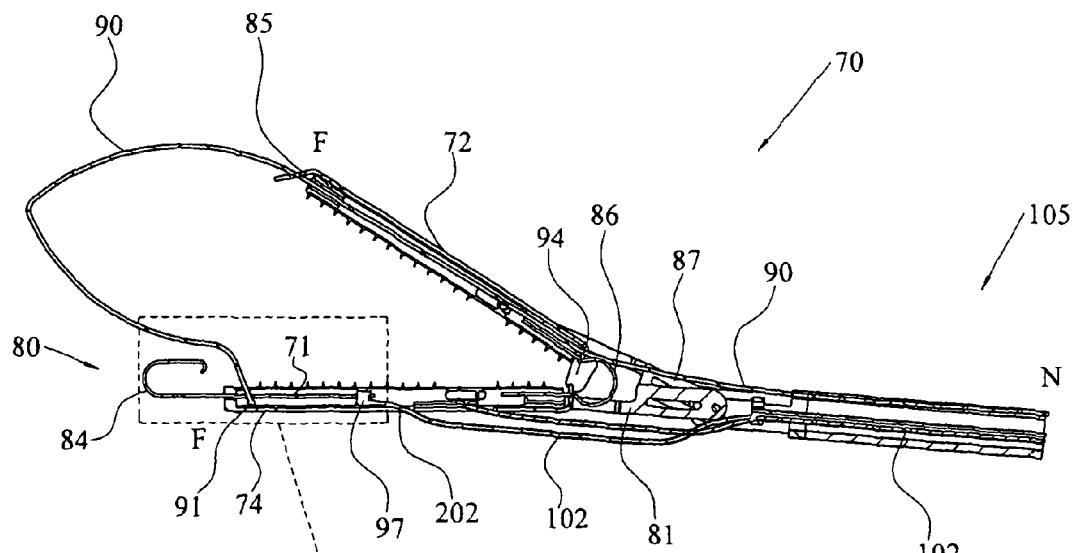
FIG. 31A is a cross-sectional view of a surgical compression clip constructed according to a fifth clip embodiment of the present invention, the clip being in its open position and attached to its associated applier.
Figure 31B:
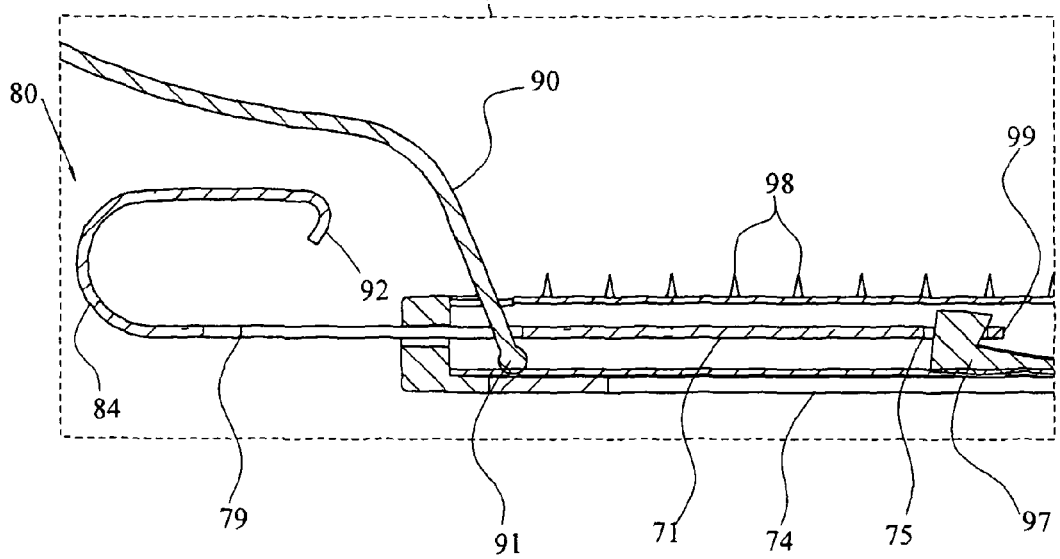
FIG. 31B is an enlarged view of a portion of the distal end of the clip shown in FIG. 31A.

FIG. 31A presents a side cross-sectional view of a surgical compression clip 70, constructed according to a fifth embodiment of the present invention, together with its associated applier 105. FIG. 31B is an enlarged view of the distal end F of a first arm 74 of clip 70, including the clip's latch 80 mechanism.

Clip 70 is formed of a first arm 74 and a second arm 72 which are held apart from each other by a force exerted by a hinge spring 86 (force applier). Hinge spring 86 is made of a shape memory material, typically, but without intending to be limiting, a Ni—Ti alloy. Arms 72 and 74 are formed having teeth 98 on their faces which lie opposite each other. The teeth are positioned so that they mesh when the arms are brought proximate to each other. The teeth can be formed as an integral part of arms 72 and 74. Alternatively, they can be formed as separate elements and connected to arms 72 and 74 by, for example, welding or by any one of many other techniques known to those skilled in the art.

Figure 40:
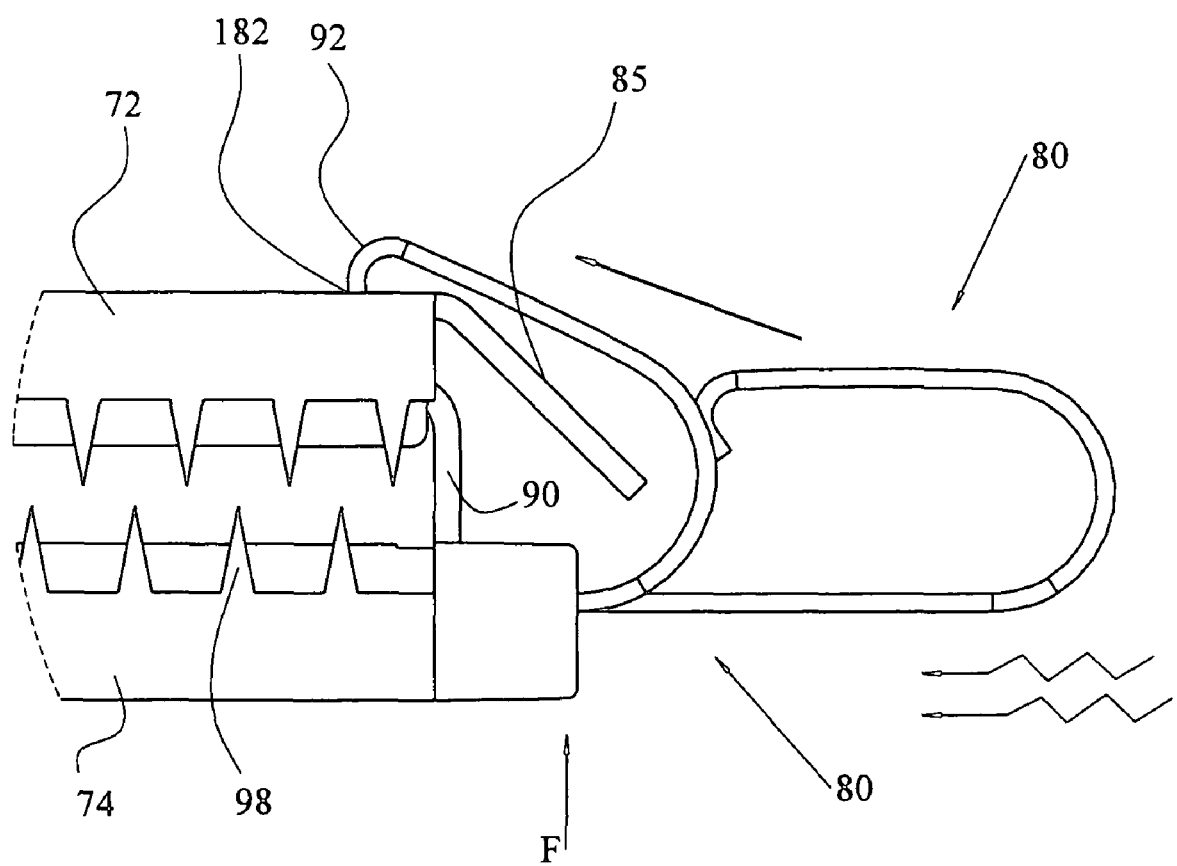
FIG. 40 shows an enlarged view of the clip shown in FIG. 31A including the clip's distal end and its locking process.

Second arm 72 has a slant-shaped guide 85 attached to its distal end F. Guide 85 helps lift latch 80 so that it can snap into place as shown in FIG. 40 to be discussed below. Arms 72 and 74 are typically constructed of metal, e.g. stainless steel or other medical grade metals. However, without being limiting, it may also be constructed of plastic by ejection molding. Arms 72 and 74 are formed so that one end of each arm receives the ends of hinge spring 86.

Restrictor element 94 (best seen in FIGS. 37 and 38) extends from the proximal end of arm 72, and is positioned on the proximal side of the most proximal tooth 98. The function of restrictor element 94 is to prevent tissue from entering into the region occupied by hinge spring 86. This is essential to ensure that all of the tissue grasped will be compressed; tissue that is not compressed will not undergo the required necrotic process.

A latch 80 is inserted in first arm 74 of surgical clip 70. Latch 80 has a crook-shaped end 84 and includes a straight portion 71. Crook-shaped end 84 is also described herein as an engageable end. This is intended to indicate that any construction, not necessarily a crook-shaped construction, capable of engaging with a catch as described below would also be acceptable. Latch 80 is connected to an anchor element 97 which lies inside a rectangular hole 75 (best seen in FIG. 35) positioned at the latch's non-crook shaped end 99. This is best seen in FIG. 31B. Latch 80 is typically formed of a Ni—Ti alloy, but other shape memory materials may also be used. Additionally, other materials having some elasticity may also be satisfactory for use.

Shown in FIG. 31A is a wire 90 which runs from the distal end F of arm 72 to the distal end F of arm 74. One end 91 of wire 90 is ball-shaped and is attached to latch 80 through first arm 74. The second end of wire 90 extends all the way through second arm 72 reaching past proximal end N of clip applier 105, to the proximal, i.e. user, end of an endoscope (not shown). Wire 90 may also be described herein as a cable without any intent at differentiating between the two descriptions.

Attached to anchor element 97 at the non-crooked shaped end 99 of latch 80 is a cable 102 which extends through clip applier 105 past its proximal end N to the proximal end of the endoscope N (FIG. 1A) where an applier actuator (e.g. 306 or 308 in FIG. 1A) is located.

Arms 72 and 74 may be considered to consist of both compressing elements and securing elements and in this way be subsumed into the overall rubric of the other clips discussed herein. In the Figures, each arm appears as a single piece but essentially it consists of a bar, typically but without intending to be limiting, with a rounded cross section having teeth joined to it. The toothed portion (securing element) may by welded to the round bars (compressing elements) or otherwise joined or produced as an integral part of the round bars. The round elements are typically hollow and they can be considered cylindrical. The hollow arms allow insertion therein of hinge spring 86, latch 80, and wires 90 and 102 used to operate clip 70.

Figure 32:
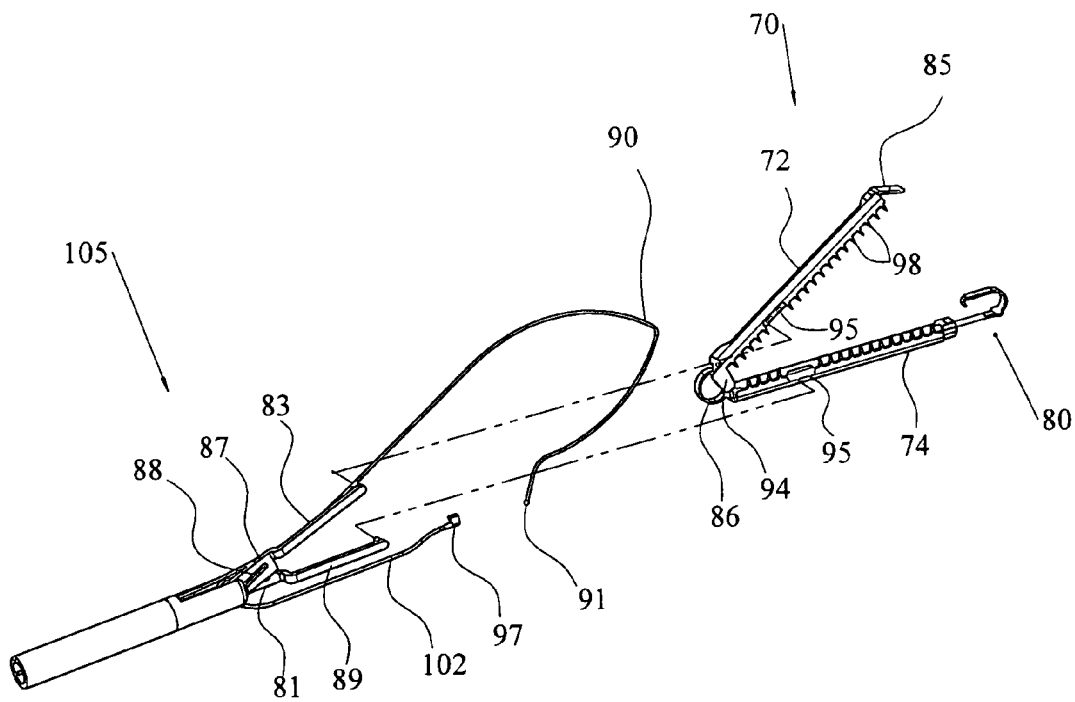
FIGS. 32 and 33 are different partially exploded views of the surgical compression clip and applier in FIG. 31A.
Figure 33:
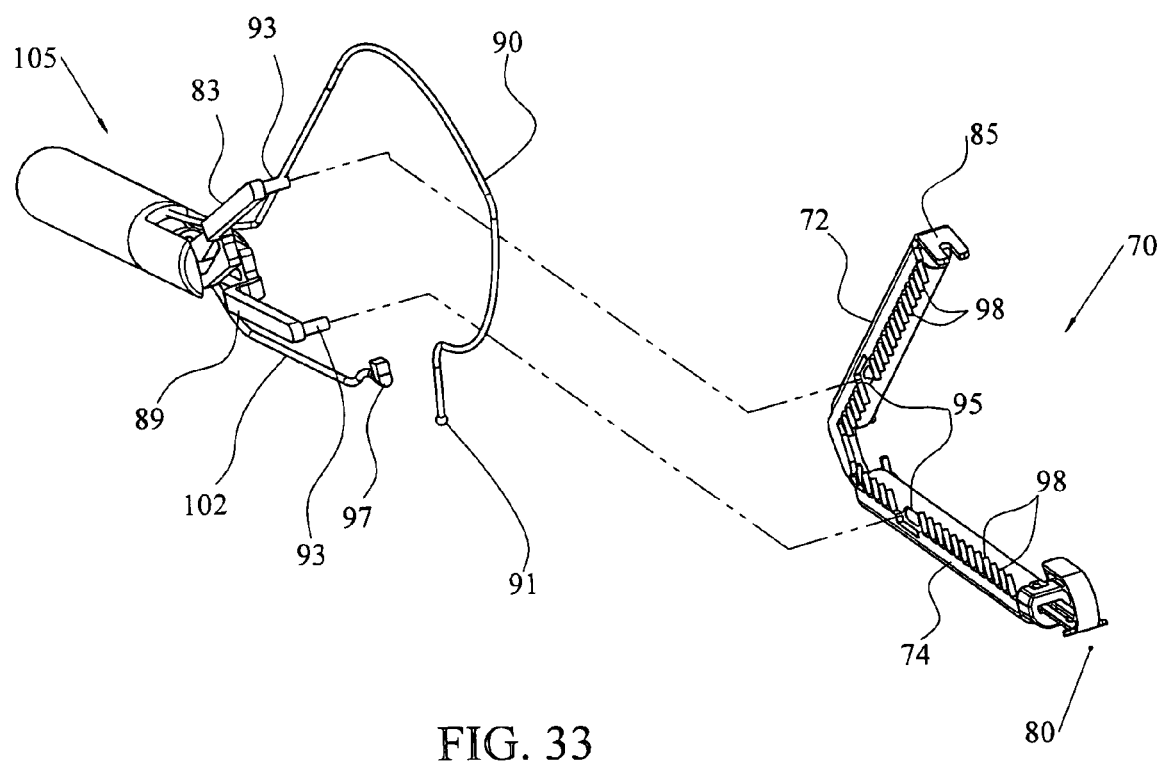

FIGS. 32 and 33 are partially exploded views of the elements of surgical clip 70 and clip applier 105 shown in and discussed in conjunction with FIGS. 31A and 31B. FIGS. 32 and 33 also show applier arms 83 and 89 of applier 105 to which first and second arms 72 and 74, respectively, of clip 70 are joined. Attachment is effected by applier arm projections 93; projections 93 extend substantially transversally from the ends of applier arms 83 and 89. Applier arm projections 93 are positioned in projection receptor spacings 95 on arms 72 and 74 when applier 105 is engaged to clip 70.

Figure 34:
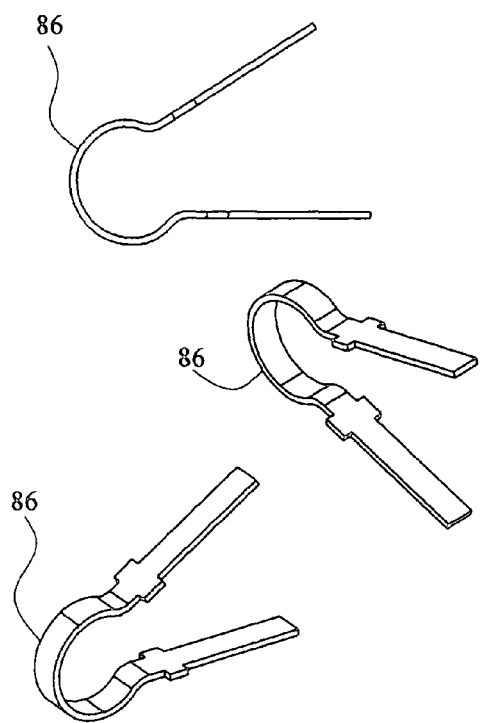
FIG. 34 shows different views of the shape memory spring element of the clip in FIG. 31A.

FIG. 34 shows several isometric and side views of a typical, but non-limiting, hinge spring 86 design.

Figure 35:
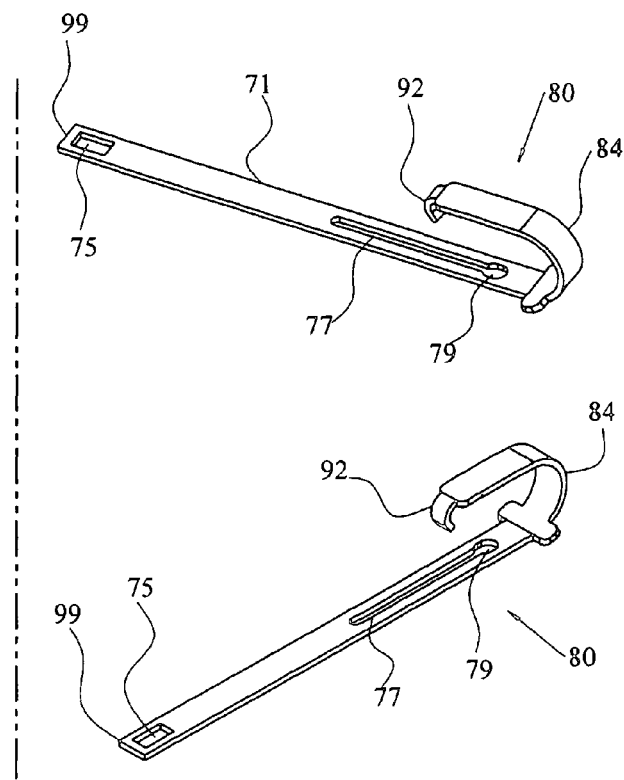
FIG. 35 shows different views of the latch arm of the clip presented in FIG. 31A.
Figure 43:
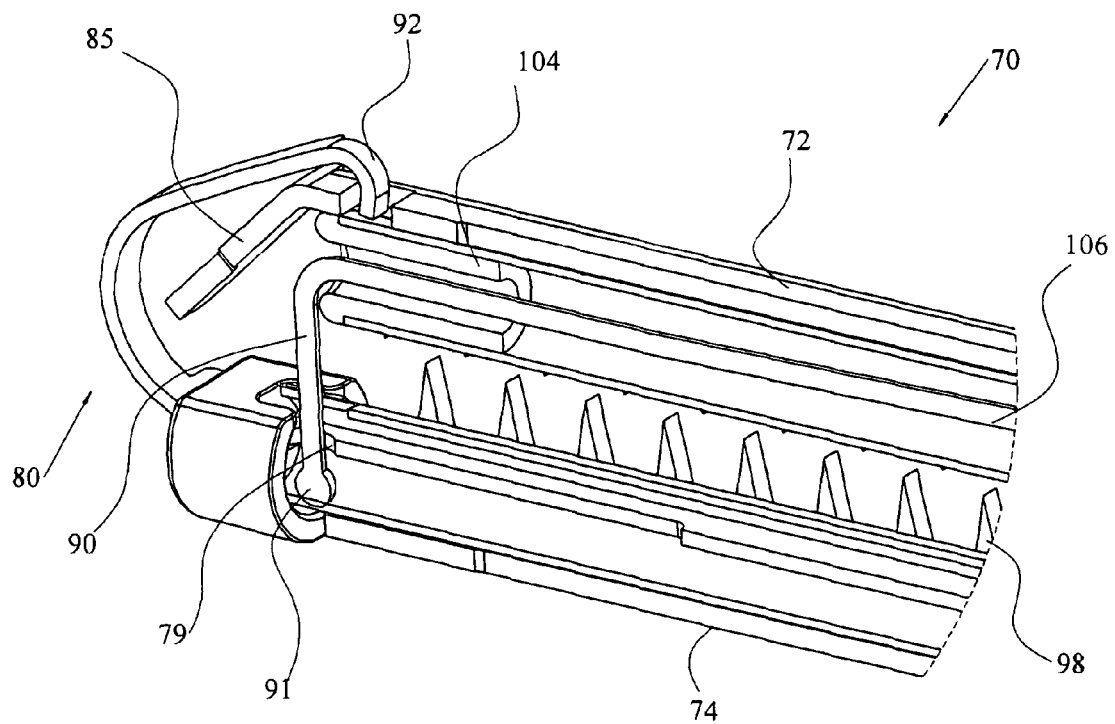

FIG. 35 shows the details of latch 80. The straight section 71 of latch 80 includes a straight slot 77 with a round hole 79 at its distal end. The end 91 of wire 90 (FIG. 31B) is inserted and held in slot 77, the diameter of end 91 being greater than the width of slot 77. When clip 70 is completely positioned around the tissue to be resected, latch 80 is snapped into place, as discussed in greater detail below. As latch 80 snaps into place, wire 90 is then detached naturally from latch 80 and from clip 70 through hole 79 (FIGS. 35 and 43). After wire 90 is freed from latch 80, wire 90 is pulled entirely through second arm 72 toward the proximal end of the endoscope where it exits the endoscope and the body. A rectangular hole 75 at the end 99 of straight section 71 of latch 80 is used to anchor latch 80 to anchor element 97 (FIG. 31B) which is used by the user to pull latch 80.

FIG. 35 also shows that at the end of crook-shaped end 84 of latch 80 is a curved latch snout 92. Curved snout 92 is intended to catch in latch hole 182 discussed below in conjunction with FIGS. 38 and 40. This ensures that latch 80 snaps into place when clip 70 is in its closed position, thereby ensuring compression of the tissue between arms 72 and 74.

Figure 36:
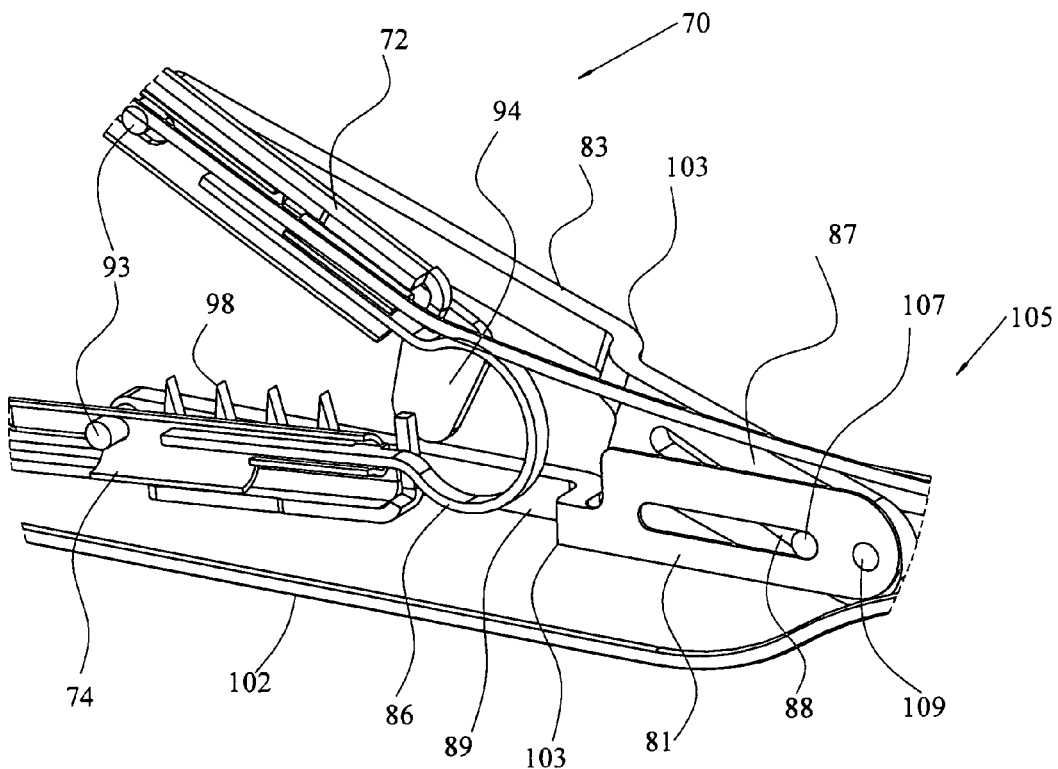
FIG. 36 shows an isometric view of the clip's spring element at the hinge region of the clip shown in FIG. 31A.
Figure 37:
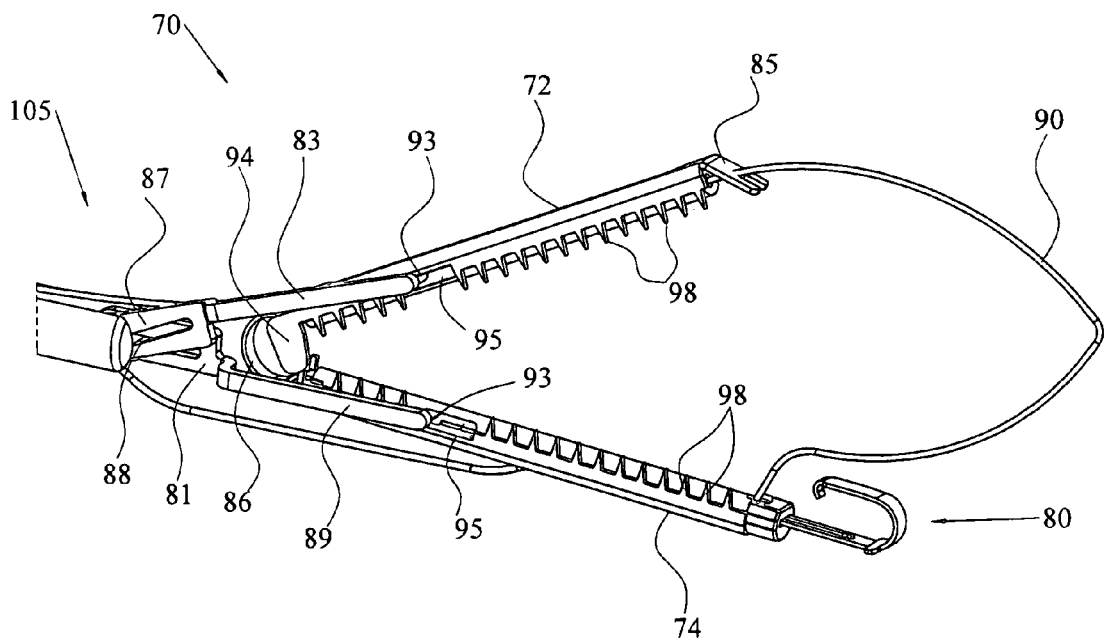
FIG. 37 shows an isometric front side view of the clip in FIG. 31A, the clip in its open position.

FIG. 36 shows an expanded isometric side view of the hinge spring 86 section of clip 70 and the section of clip applier 105 proximate to this section of clip 70. FIG. 37 shows an isometric front side view of clip 70, wire 90 and the distal end of applier 105. Both FIGS. 36 and 37 show clip 70 in its open position.

FIG. 36 shows hinge spring 86 as being inserted into arms 72 and 74 of clip 70. FIG. 37 shows the attachment of applier arms 83 and 89 which close clip arms 72 and 74 by exerting a force counter to the force exerted by hinge spring 86. The latter tends to force clip 70 open. Applier arms 83 and 89 are attached to arms 72 and 74, respectively, by applier arm projections 93, the latter being inserted into the clip's projection receptor spacings 95. Projections 93 and spacings 95 are also shown in FIG. 33. FIG. 36 also shows that applier arms 83 and 89 are integrally formed with pushing attachments 87 and 81, respectively. These are typically, but not necessarily, single piece elements, that is elements 89 and 81 form a single integral piece and elements 83 and 87 form another single integral piece. Alternatively, elements 83 and 87 (and 89 and 81) can be welded together from two or more separate structures.

Figure 38:
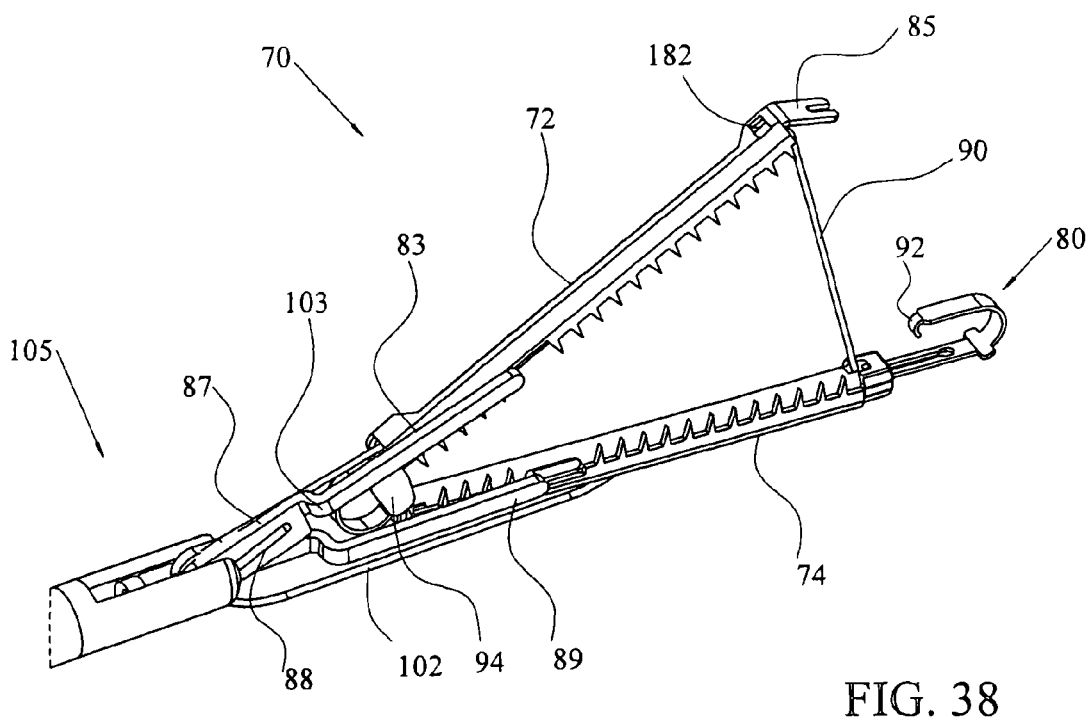
FIGS. 38 and 39 show different views of the clip in FIG. 31A where the wire of the clip has been drawn taut.

These pieces include a bend 103 readily recognizable in FIGS. 36 and 38; bend 103 is required to ensure planarity of the pushing device.

Pushing attachments 87 and 81 each has an applier arm slot 88 in which a pushing attachment pin 107 moves when rotating pushing attachments 81 and 87 around pin 109 (FIGS. 31A and 36).

Figure 39:
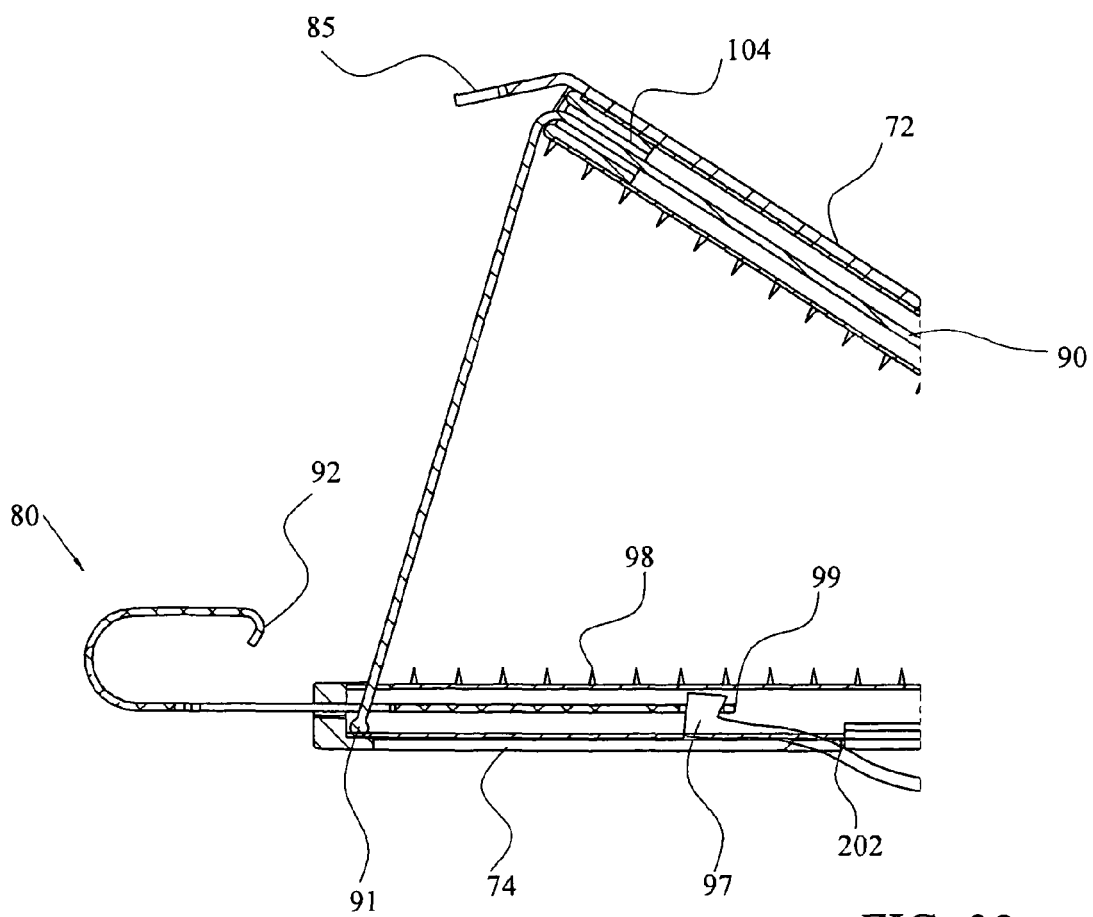

FIGS. 38-39 show different views of clip 70 and the distal end of clip applier 105 when wire 90 is pulled taut as a first step in closing applier 105. The taut wire keeps tissue (not shown) from slipping out when positioned between arms 72 and 74 as these arms move toward each other in a scissor-like or clamp-like fashion.

The wire is pulled taut after the tissue has been brought completely into clip 70 in its open position; the tissue is grasped and held between arms 72 and 74 and wire 90. Continuing to pull wire 90 brings distal end F (FIG. 31A) of arm 72 close to distal end F (FIG. 31A) of arm 74 until arm 72 is pressed against the tissue situated between arm 72 and arm 74. At this stage, latch 80 is brought to its locking position as will be described below. Wire 90 enters arm 72 through wire aperture 104. Wire section 106, best seen in FIG. 41, extends to the proximal end of the endoscope (not shown) and is pulled at that end when it is desired to bring wire 90 to its taut position between arms 72 and 74 of the clip.

Figure 42:
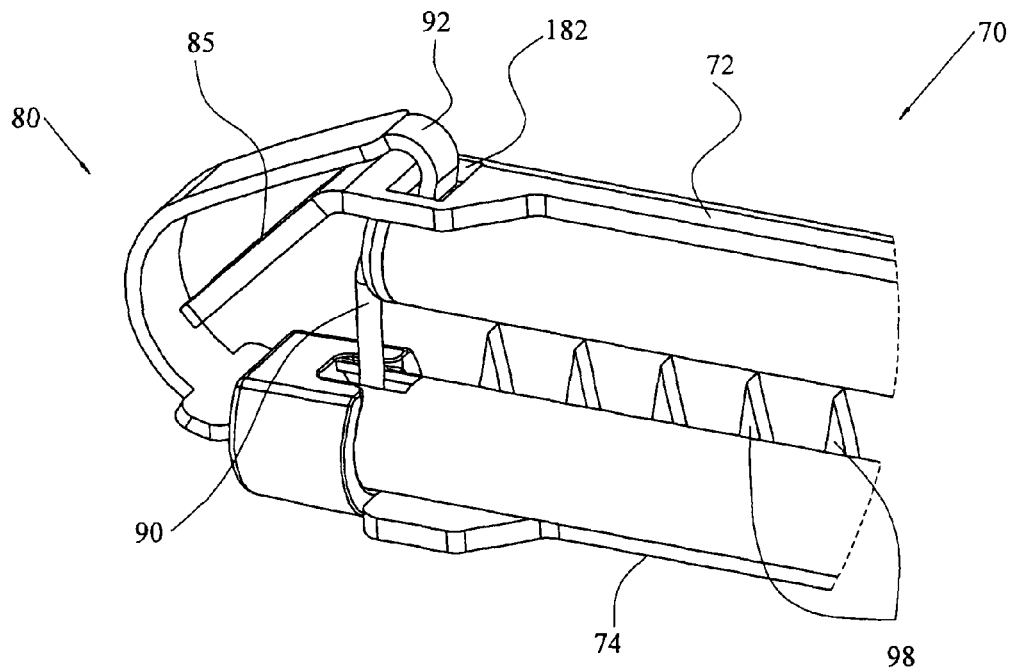
FIGS. 42 and 43 show additional enlarged views of the distal end of the clip shown in FIG. 31A, the clip being in its closed position.

FIG. 40 shows the distal end F of clip 70 and the locking action of latch 80. Between arms 72 and 74, tissue (not shown) is positioned and wire 90 is pulled taut. At that point, the distance between clip arms 72 and 74 is small. When arms 72 and 74 are in apposition, latch 80 is pulled by cable 102 (see FIGS. 31A and 37 for example) in a proximal direction indicated by the wavy double arrows. As latch 80 moves in the direction of those arrows, the rounded latch head slips (indicated by the single solid arrow) over slanted guide 85 until it contacts arm 72. It then latches when latch snout 92 (FIGS. 35 and 38) enters latch hole 182 (FIGS. 38 and 42). When in that position, latch 80, in concert with hinge spring 86 (force applier), exert a compressive force which acts in a line between arms 72 and 74. In the latched stage, arms 72 and 74 are separated somewhat, the gap between them arising from the thickness of the gripped tissue.

It should readily be understood that any other suitable catch structure can be used in place of latch hole 182. The choice of a hole here, functioning as a latch catch, should be considered as exemplary only. A protrusion with which latch 80 can engage would work equally as well. In fact, any engagement means that can engage and hold latch snout 92 of latch 80 is contemplated by the present invention.

The tissue situated between arms 72 and 74 of clip 70 prevents the clip from fully tracking clip applier 105 and returning to its completely closed position. As a result of this lack of complete tracking, applier arm projections 93 disengage from projection receptor spacings 95 by themselves and applier 105 falls away from clip 70.

As noted above, the shape memory elements used to effect opening or closing of the compression clips described herein are typically described as hinge springs. However, these elements can more generally be classified as and called force appliers. Latch 80, because it is typically formed of shape memory materials, acts as a force applier that holds compression clip 70 closed.

Figure 41:
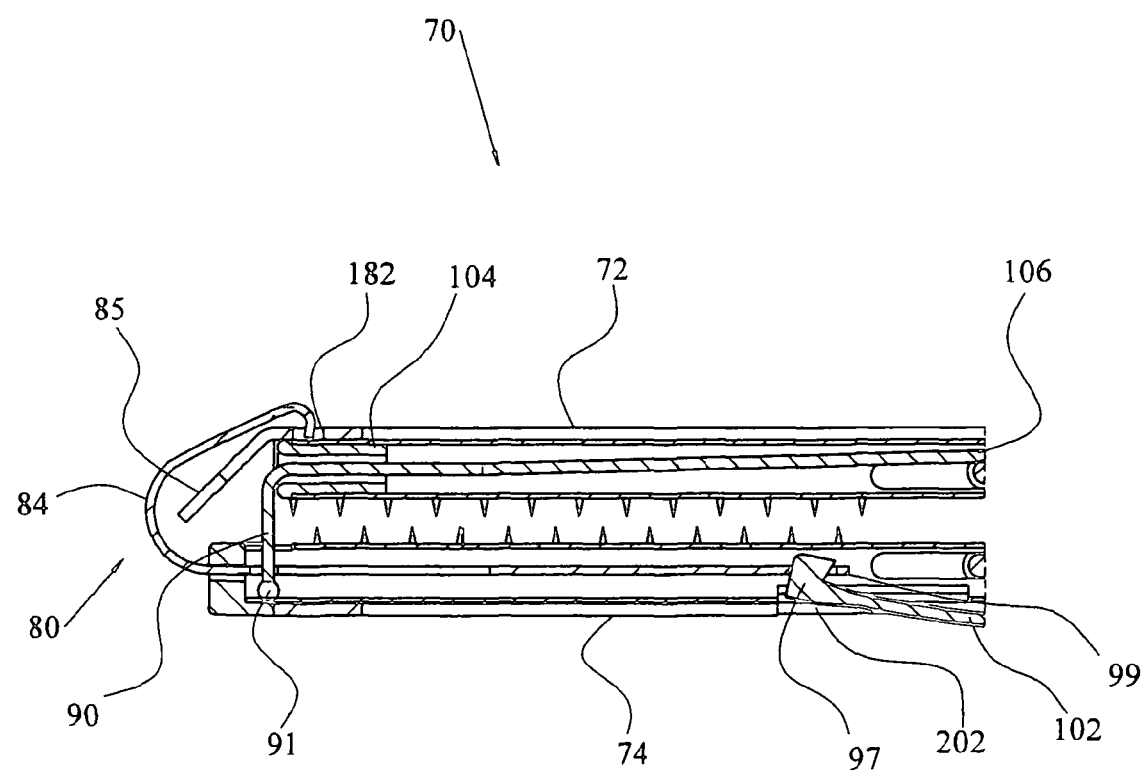
FIG. 41 shows an enlarged cross-sectional view of the distal end of the clip shown in FIG. 31A, the clip in its latched position.

FIGS. 41-43 show three different views of surgical compression clip 70 after latching as described above in conjunction with FIG. 40. FIG. 41 best shows exit hole 202 through which cable 102 is attached. Compression clip 70, by anchoring latch 80 to latch hole 182, brings anchor element 97 to exit hole 202, allowing anchor element 97 to naturally exit through hole 202. Both cable 102 and anchor element 97 are then pulled toward and through applier 105. From there they are pulled toward the proximal end of the endoscope and withdrawn from the body.

Figure 44:
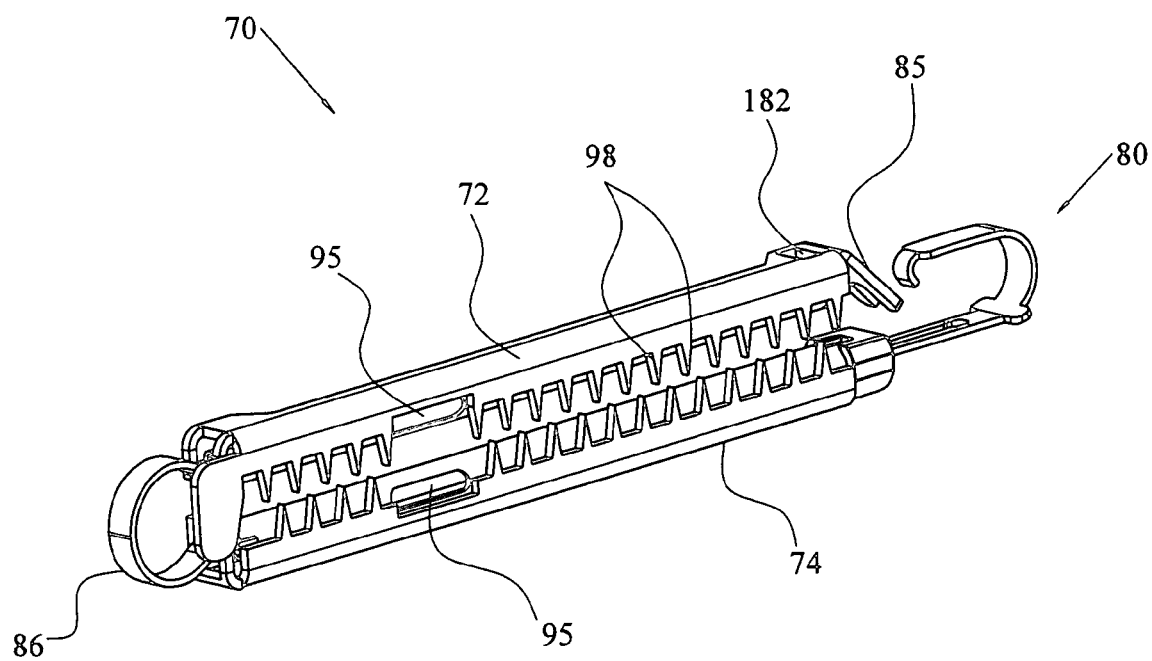
FIG. 44 shows an isometric view of the clip shown in FIG. 31A, the clip in its closed position and ready for insertion into a clip applier.

FIG. 44 shows an isometric view of a closed, but unlatched, surgical compression clip 70 constructed according to the embodiment shown in FIGS. 31A-43. FIG. 44 reflects the position of clip 70 as it is delivered to the site of a lesion by applier 105 via a working channel of an endoscope or via a secondary lumen of a multi-lumen sleeve encasing an endoscope. The use of multi-lumen sleeves is discussed below in conjunction with FIGS. 45-53.

Applier 105 is attached to clip 70 via applier arm projections 93 of applier arms 83 and 89 (see for example FIG. 33) at receptor spacings 95 on arms 72 and 74. In the closed but unlocked position of FIG. 44, the force exerted by applier arms 83 and 89 is counter to the force exerted by hinge spring 86. The force provided by applier 105 exerts a force which holds arms 72 and 74 adjacent to each other while clip 70 is being advanced within the endoscope (or sleeve lumen) to the lesion. At the site of the lesion, the force exerted by applier 105 is released and the clip opens.

Tissue is brought between the clip arms, the clip is closed, the lesion is severed and the site of the severed lesion is compressed between arms 72 and 74 of the clip 70 until necrosis and healing occurs. The entire process is discussed in greater detail below.

It should be noted that wire 90 is pushed forward once clip 70 approaches the suspect lesion. This relaxes wire 90 and enables the user to place it over, and/or around, the lesion. The relaxed, extended wire has a loop with an increased area through which the lesion can be pulled. With clip 70, the open arms 72 and 74 of the clip may be slid from the side of the pulled tissue after the polyp is positioned in the area between arms 72 and 74 and wire 90; this is unlike with clips 10 and 710 (FIGS. 2-3B and FIGS. 25A-26B), for example, where the polyp must be pulled through the arms of these latter clips using a grasper (discussed further below). Because of the use of wire 90, larger polyps may be treated.

A method for effecting full transmural resection using the compression clips of the present invention is illustrated in FIGS. 45-62 to which reference is now made.

Operation of the clip in other situations where tissue closure is required is similar to its operation as shown in FIGS. 45-62 and discussion presented therewith. It should readily be understood by one skilled in the art, that clip appliers can be designed as the surgical procedure and nature of the tissue to be closed warrants. The design would generally require little or no modification to the applier shown in these Figures, and those shown in concurrently filed pending application "Endoscopic Full Thickness Resection Using Surgical Compression Clips" owned by the same Applicant, incorporated by reference herein in its entirety.

It should also be readily understood by one skilled in the art that certain features of the method and of the working instruments used as shown in FIGS. 45-62 would not be required in other tissue closure procedures. For example, a severing instrument may not always be required; similarly, a grasper assembly as used in the Figures may not always be needed. In some closure procedures commercially available instruments may be used.

Figure 45:
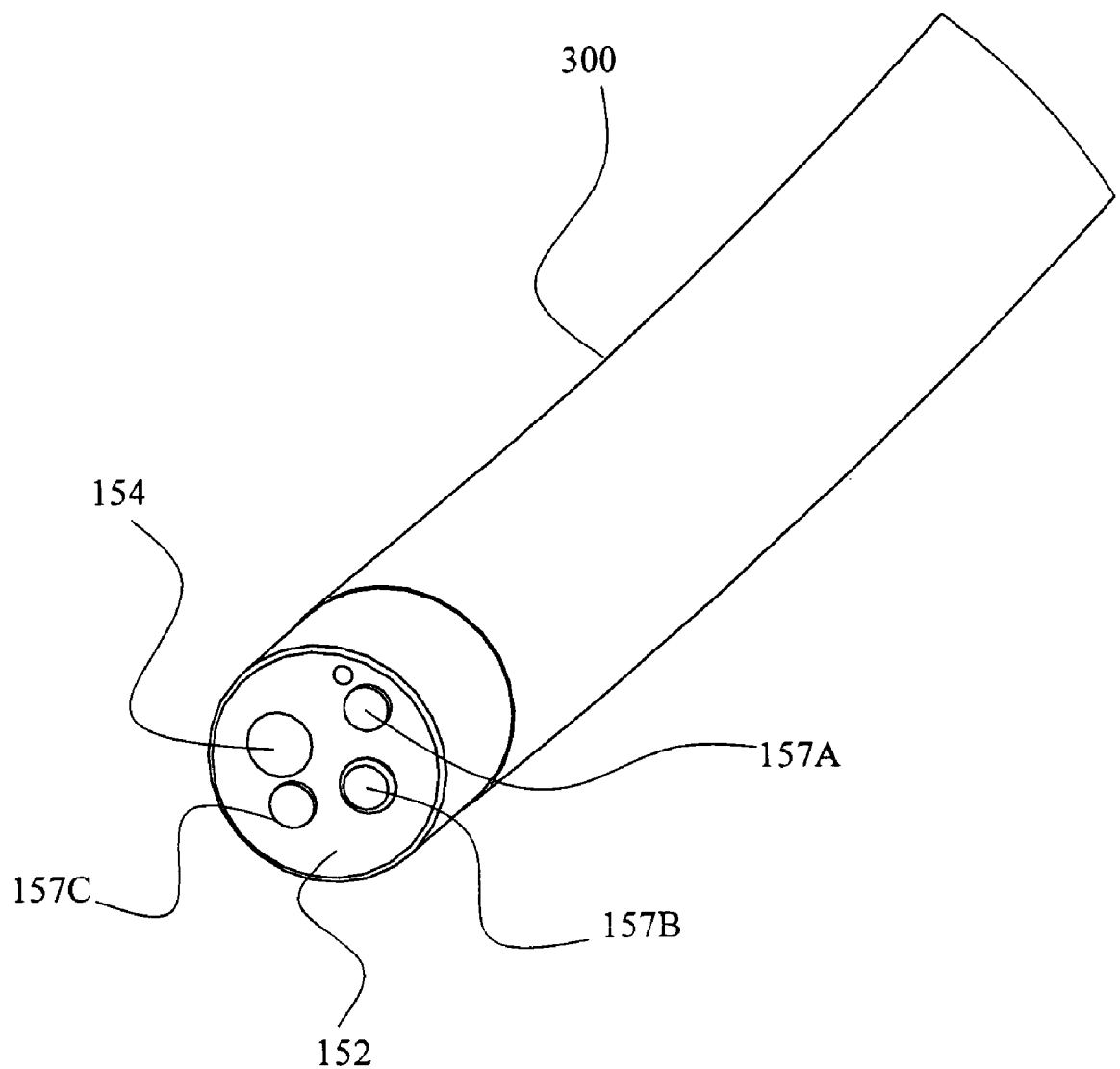
FIG. 45 shows an endoscope prior to insertion into a multi-lumen sleeve.
Figure 46:
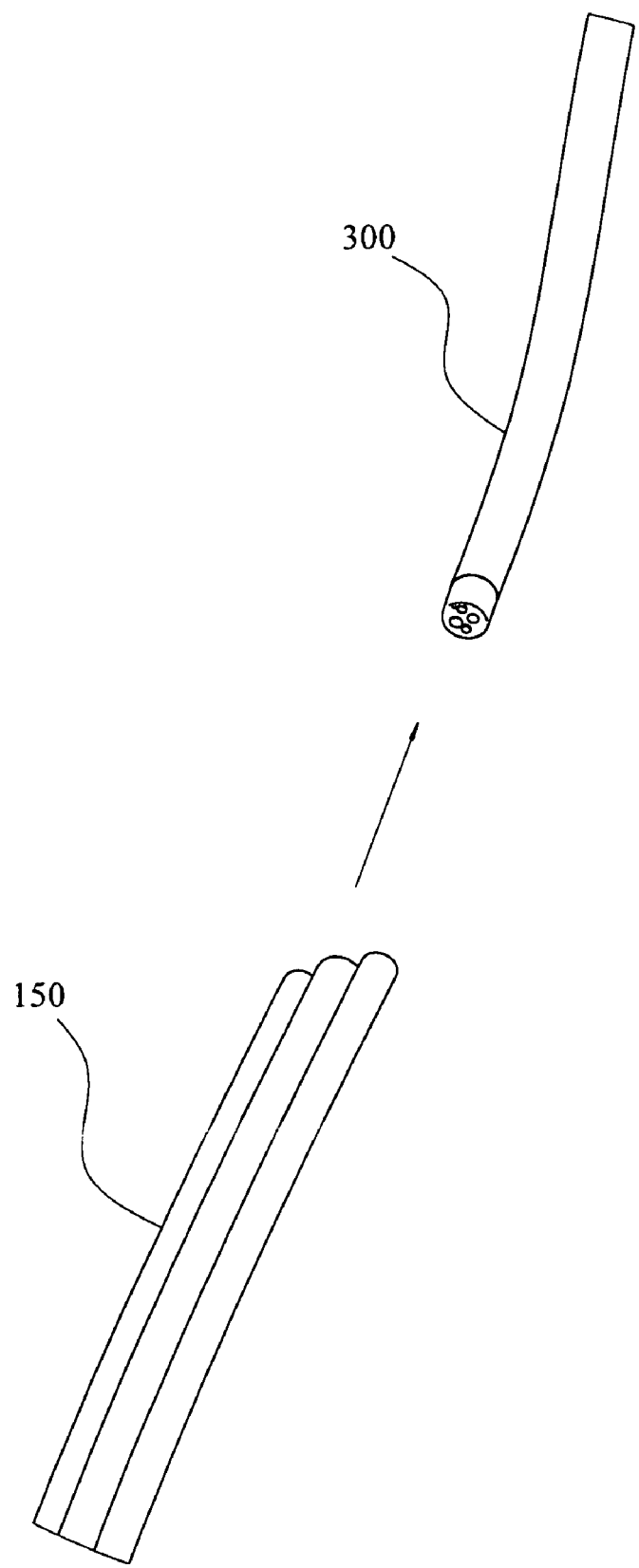
FIG. 46 shows the endoscope of FIG. 45 being inserted into a multi-lumen sleeve.
Figure 47A:
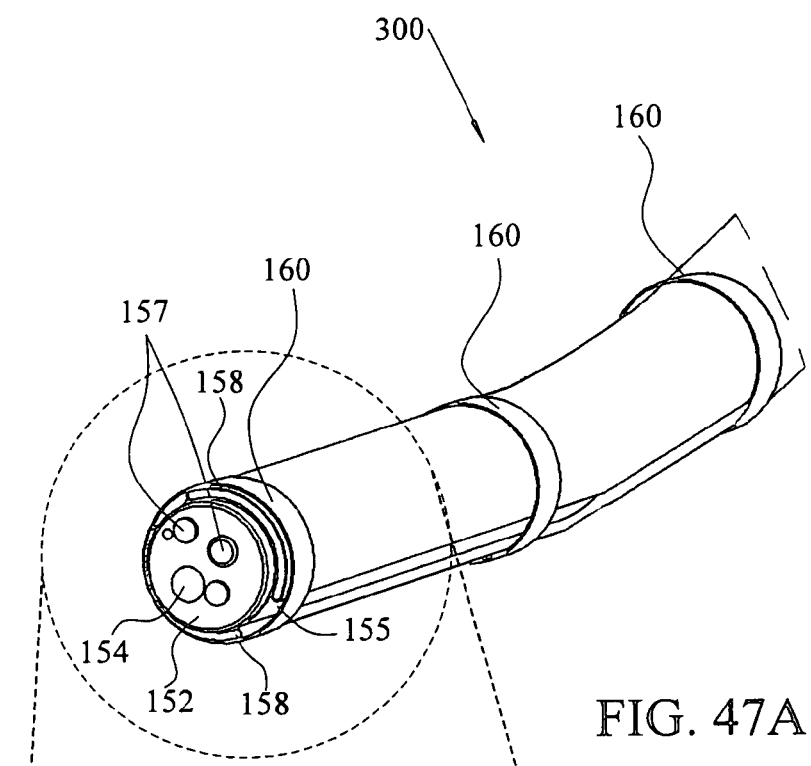
FIG. 47A shows the endoscope after insertion into the multi-lumen sleeve.
Figure 47B:
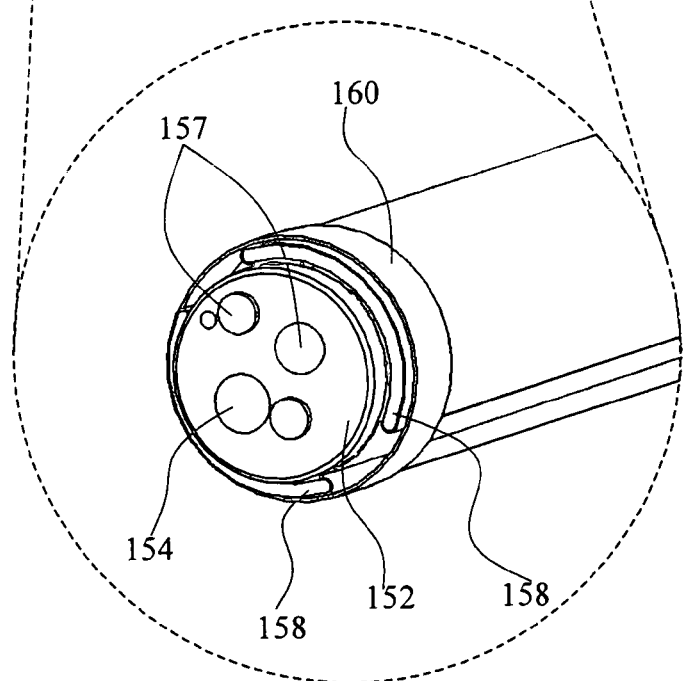
FIG. 47B shows an enlarged view of the distal end of the endoscope in FIG. 47A.

FIG. 45, to which we now return, shows an endoscope insertion shaft 300 with a working channel 154. It also contains several auxiliary elements, here three, denoted as 157A-157C. The number of working and auxiliary channels may be more or less in other embodiments of shaft 300. A multi-lumen plastic sleeve 150 is brought to and over endoscope insertion shaft 300 (FIG. 46). The endoscope insertion shaft 300 is encased in the primary lumen 155 of the multi-lumen sleeve 150 and the one or more secondary lumens 158 of sleeve 150 are typically collapsed and, if needed, held by bands 160 (FIG. 47A). The bands 160 are expandable when working instruments are inserted into the collapsed secondary lumens 158. Insertion of these instruments occurs after the distal end 152 of the endoscope shaft 300 is positioned proximate to the suspect lesion. Bands may not be required in some embodiments, if the secondary lumens 158 remain collapsed by themselves while the encased endoscope insertion shaft 300 (FIG. 47A) is inserted into a body organ or if not required by the physician. It is to be understood that means or methods other than bands may be used to ensure that the secondary lumens remain collapsed while the encased endoscope shaft is inserted into the body and positioned near the suspect lesion.

Figure 48:
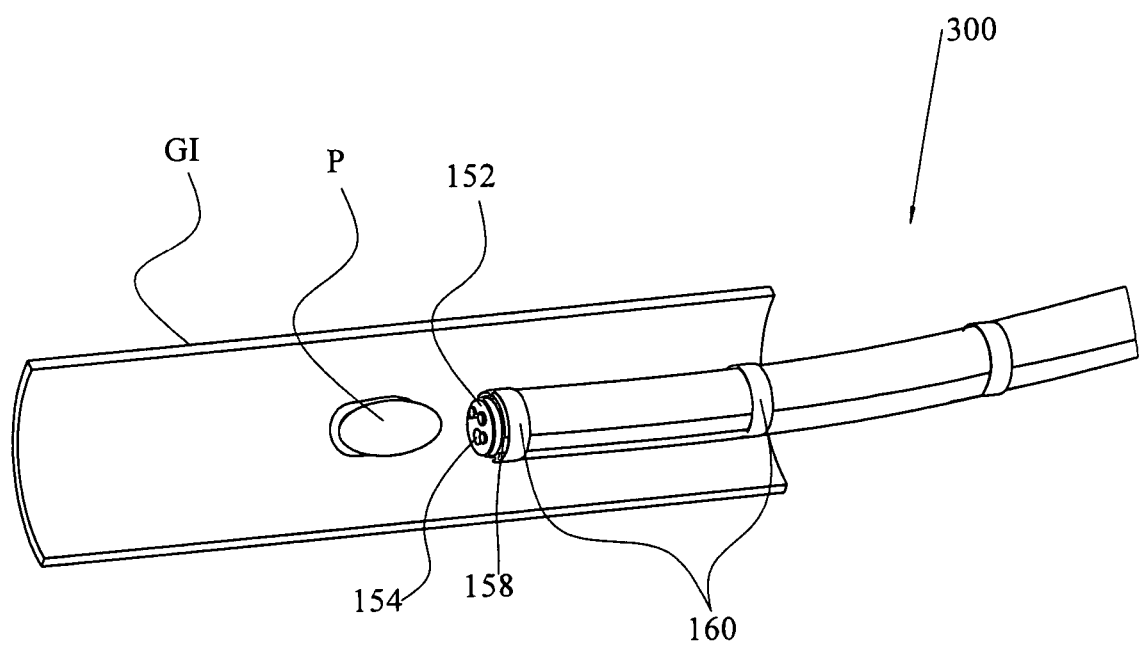
FIG. 48 shows the sleeve-encased endoscope as it approaches a polyp in the gastrointestinal tract.

The encased endoscope insertion shaft 300 is advanced within the body lumen until it is near the lesion, herein taken to be a polyp P in the gastrointestinal (GI) tract. (FIG. 48).

Figure 49:
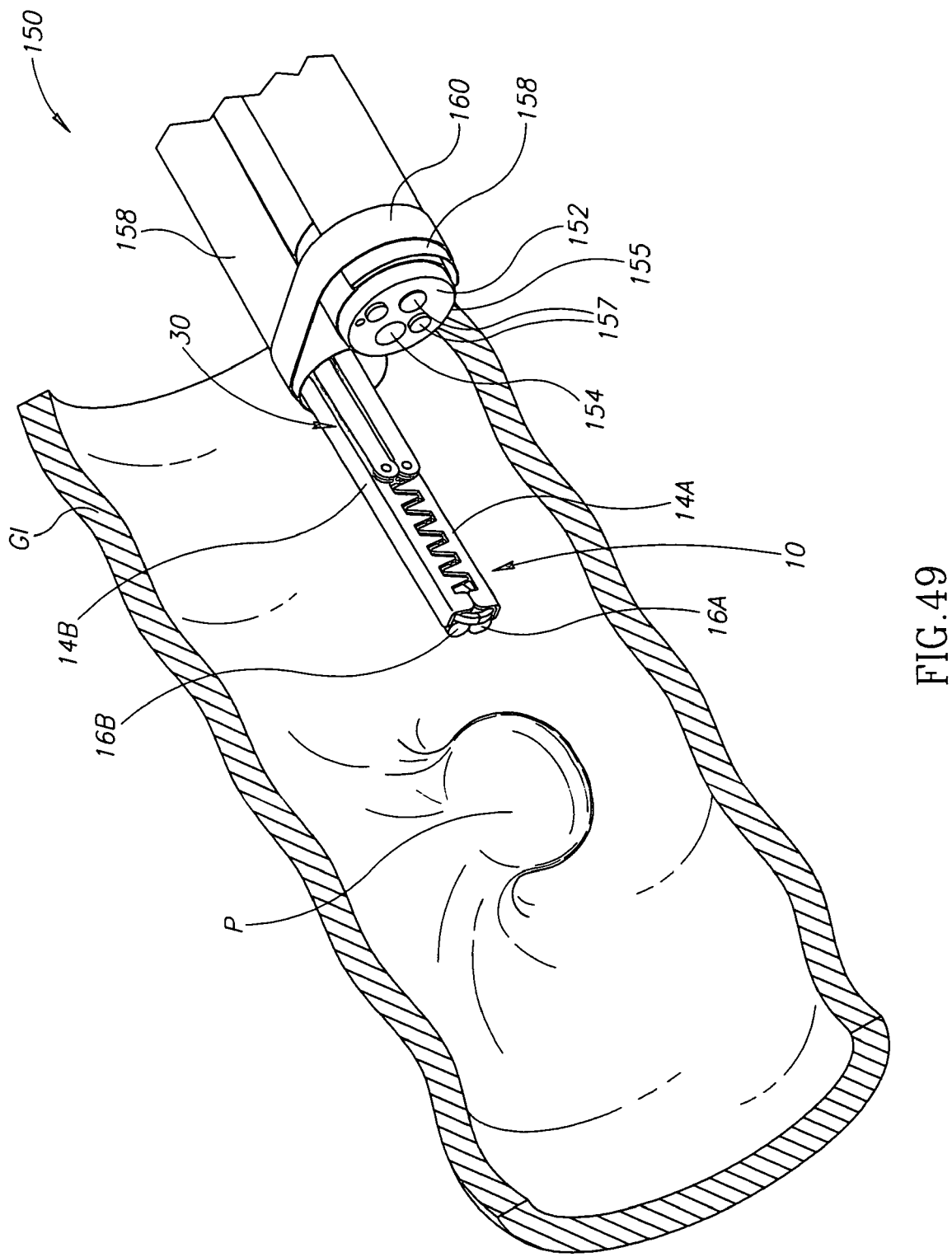
FIG. 49 shows a view of a surgical clip attached to an applier being advanced to the site of the polyp through a secondary lumen of the sleeve.

At that point a surgical compression clip 10, and its attached applier 30, both in their closed positions, are advanced through a secondary lumen 158 of the sleeve 150 to polyp P. Clip 10 exits the secondary lumen 158 still in its closed position (FIG. 49).

Figure 50:
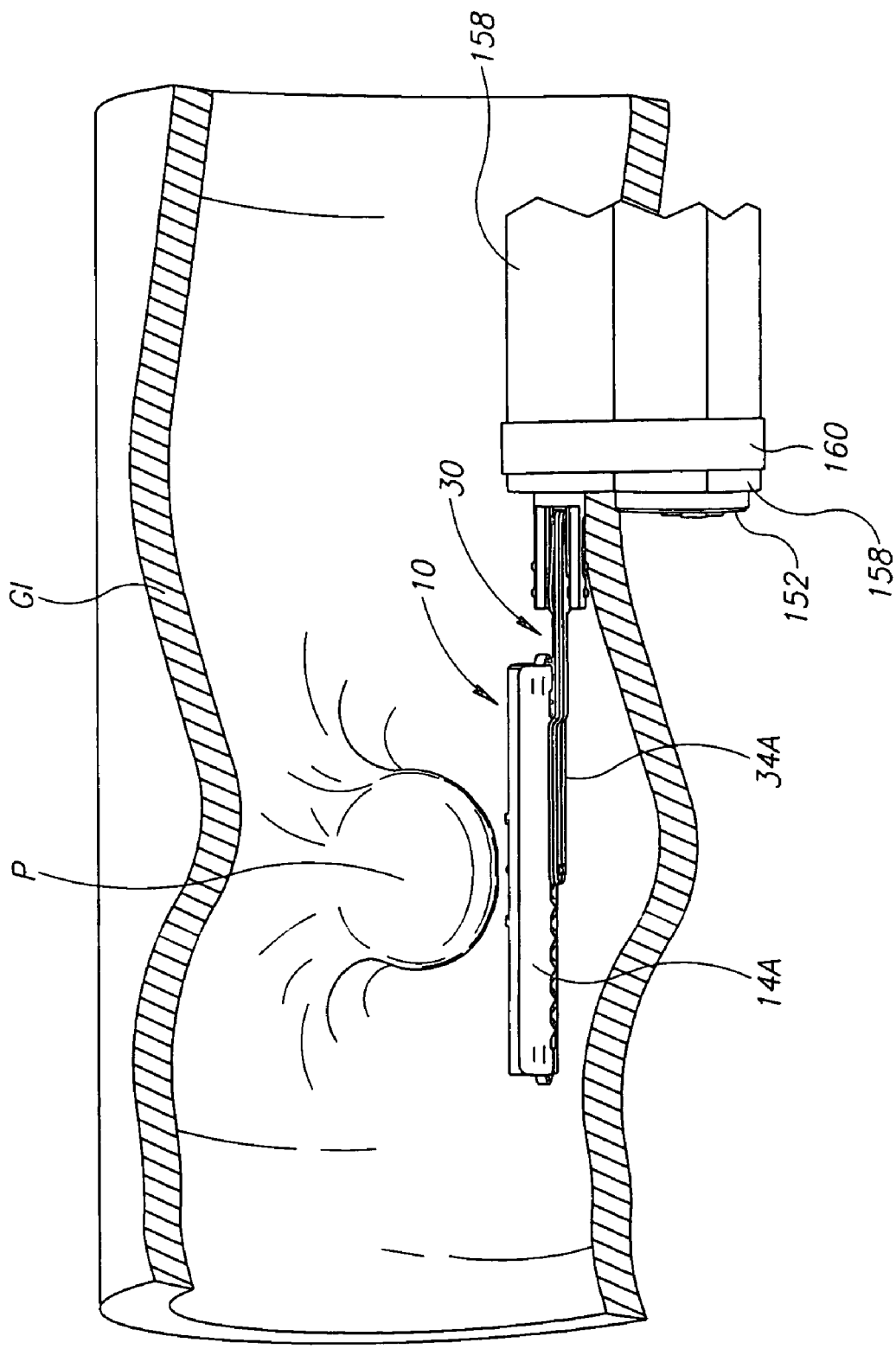
FIG. 50 shows a top side view of the surgical clip attached to an applier being positioned proximate to the polyp.

Clip 10, still in its closed position, is brought to its final position adjacent to polyp P (FIG. 50).

Figure 51:
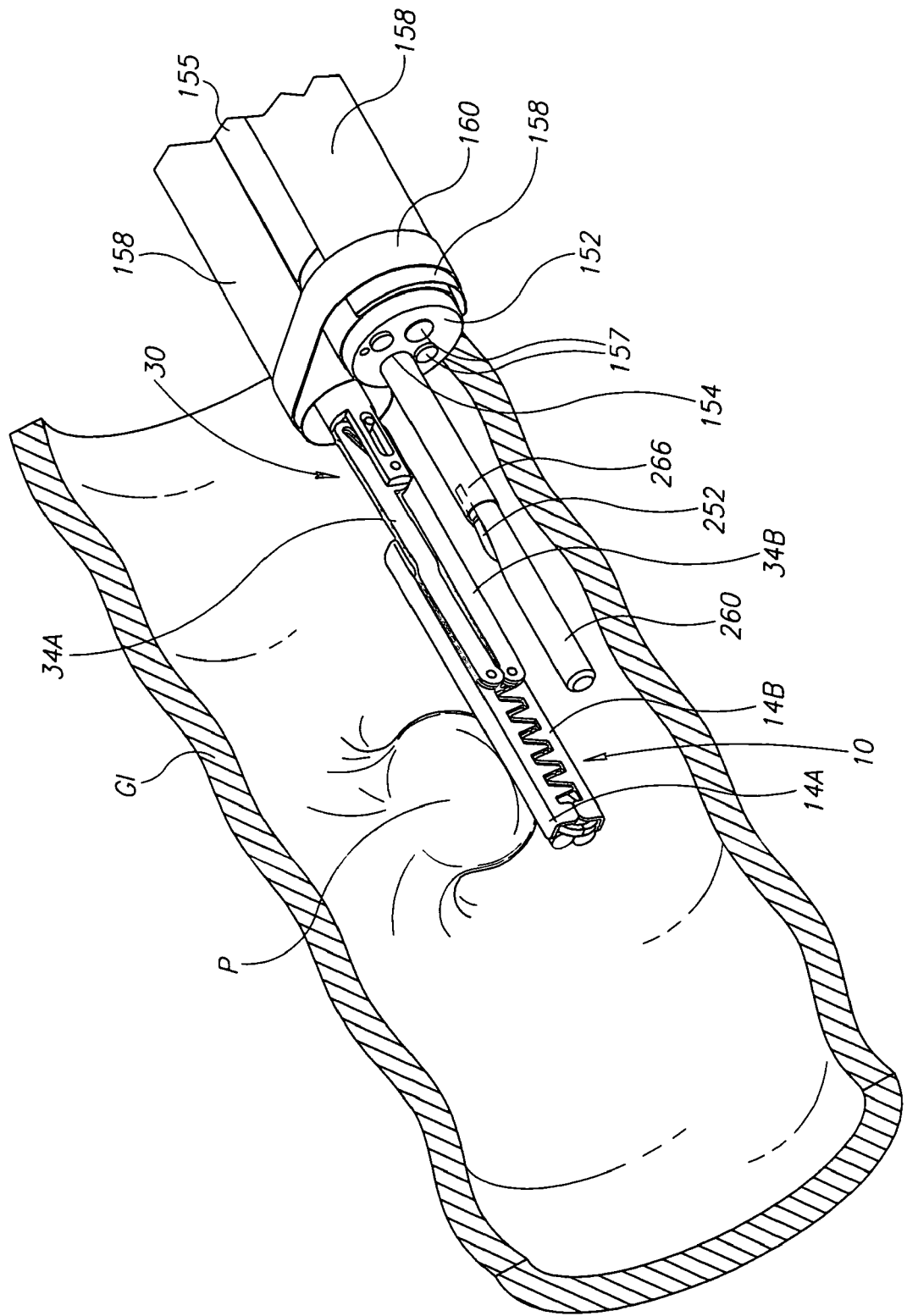
FIG. 51 shows a top side view of a surgical clip and applier positioned proximate to a polyp and a grasper assembly being positioned proximate to the polyp after advancing through a working channel of the endoscope.

A grasper assembly is then inserted into a working channel 154 of the endoscope insertion shaft 300, advanced through the shaft, and then advanced out of the distal end 152 of endoscope insertion shaft 300 to the region adjacent to polyp P (FIG. 51).

In other embodiments, the grasper assembly, i.e. grasper (not shown) and grasper transporting element 260, is introduced via a secondary lumen 158 of the multi-lumen sleeve 150 and not through a working channel 154 of the endoscope shaft. From an operational point of view, this has no significant effect on the method described.

In yet another embodiment, the grasper assembly, clip 10 and clip applier 30 may be advanced through the same secondary lumen 158 from the proximal end of the endoscope shaft to the suspect lesion.

In yet another embodiment, the grasper assembly may be inserted into and advanced through a second working channel of the endoscopic insertion shaft.

Figure 52:
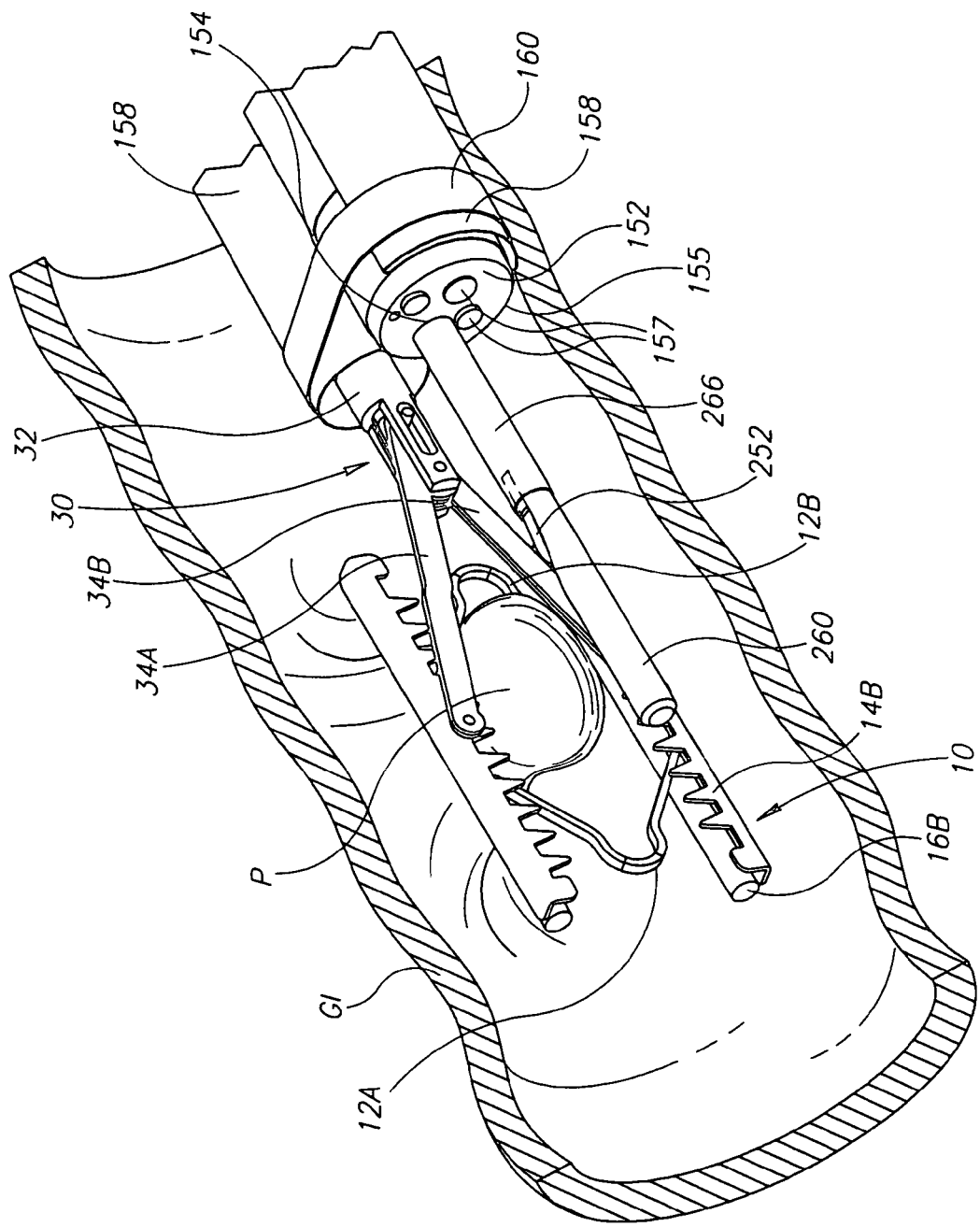
FIG. 52 shows a top side view of the opened clip proximate to the polyp.

Clip 10 is then opened by applier 30. The opened clip is positioned so as to bound polyp P so that the lesion can be pulled through the clip. FIG. 52 shows an isometric view of this step.

Figure 53:
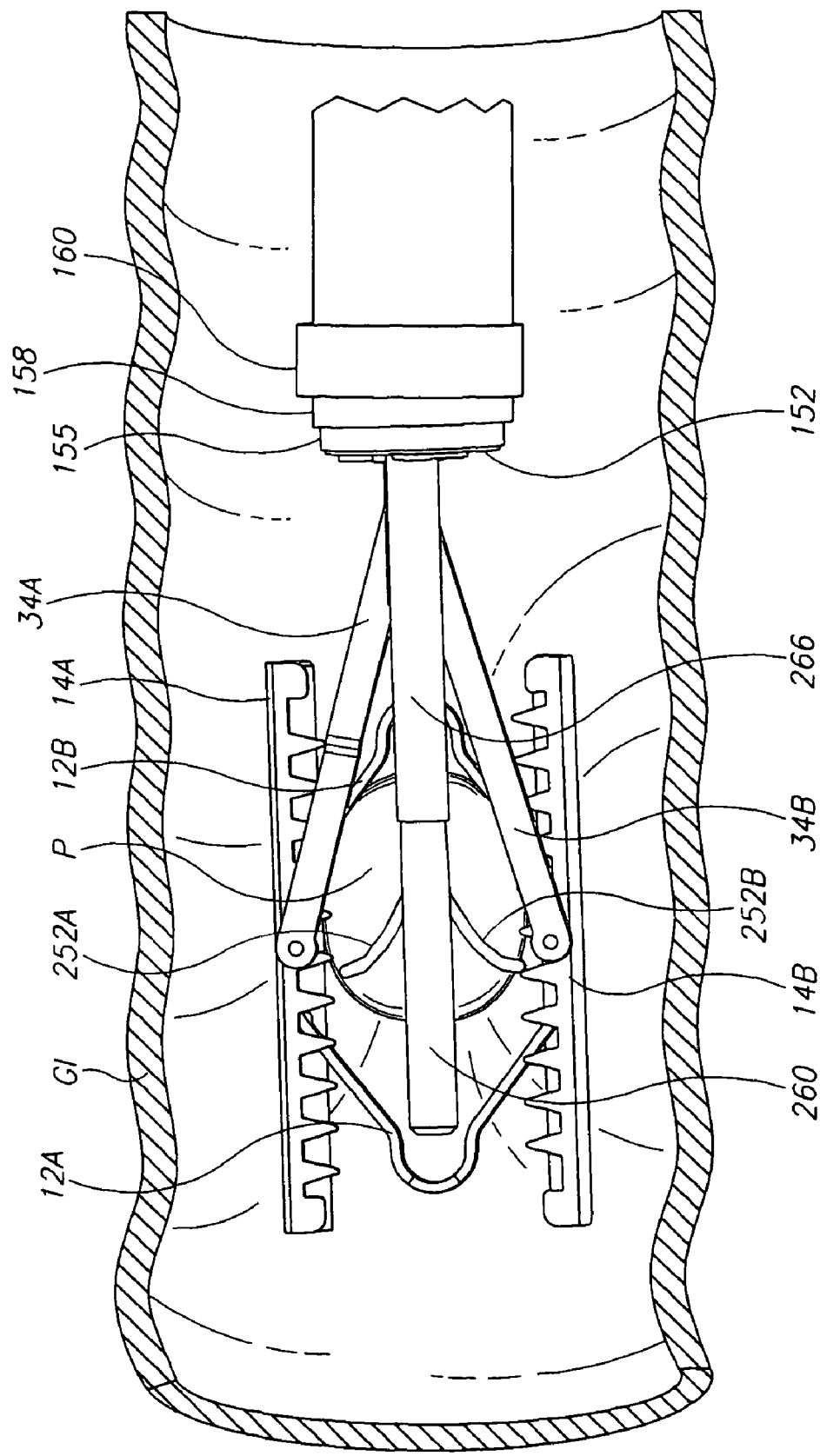
FIG. 53 shows a top view of the grasper of the grasper assembly beginning to pull the polyp through the opened clip shown in FIG. 52.
Figure 54:
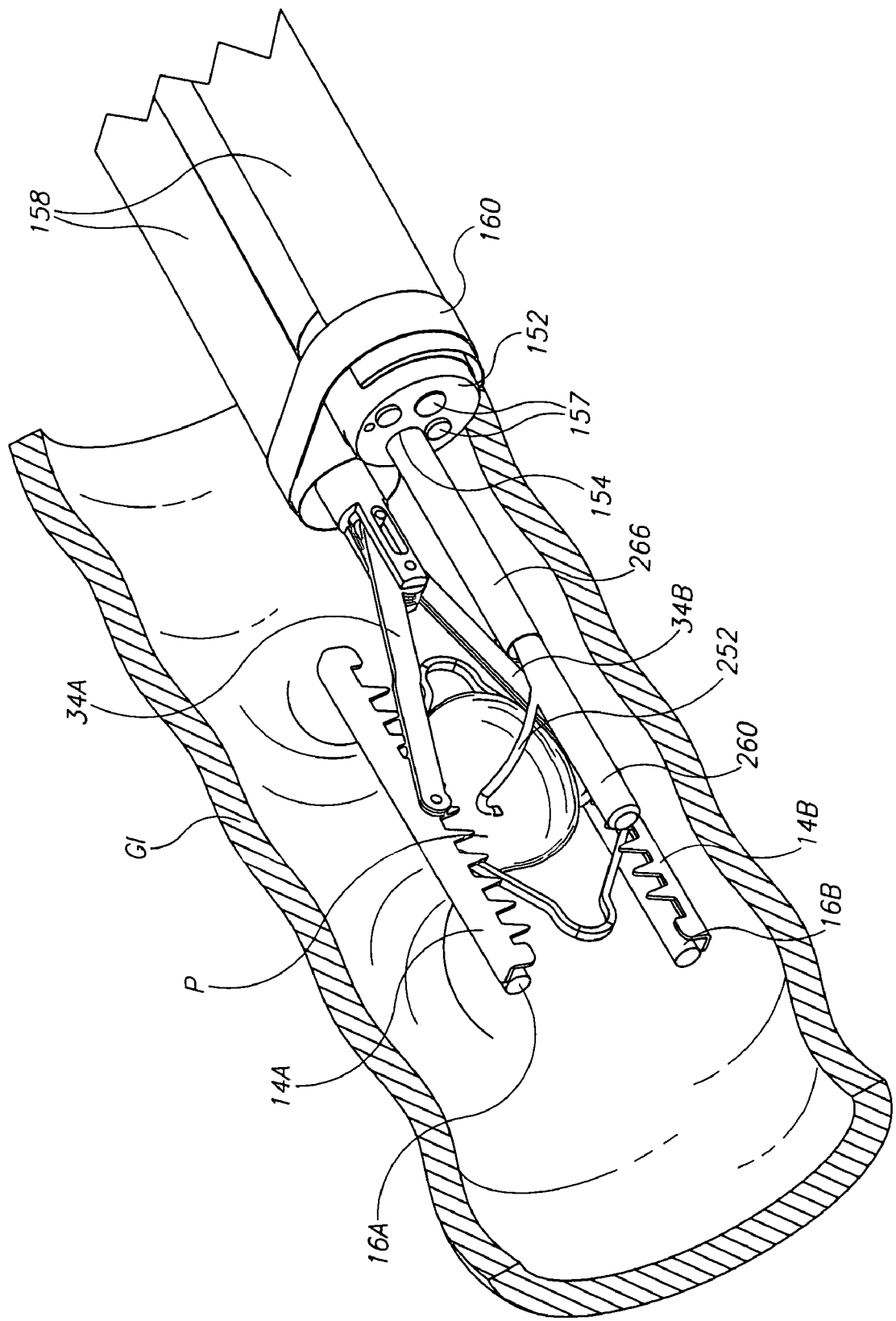
FIG. 54 shows a top side view of the grasper of the grasper assembly grasping the polyp.
Figure 55:
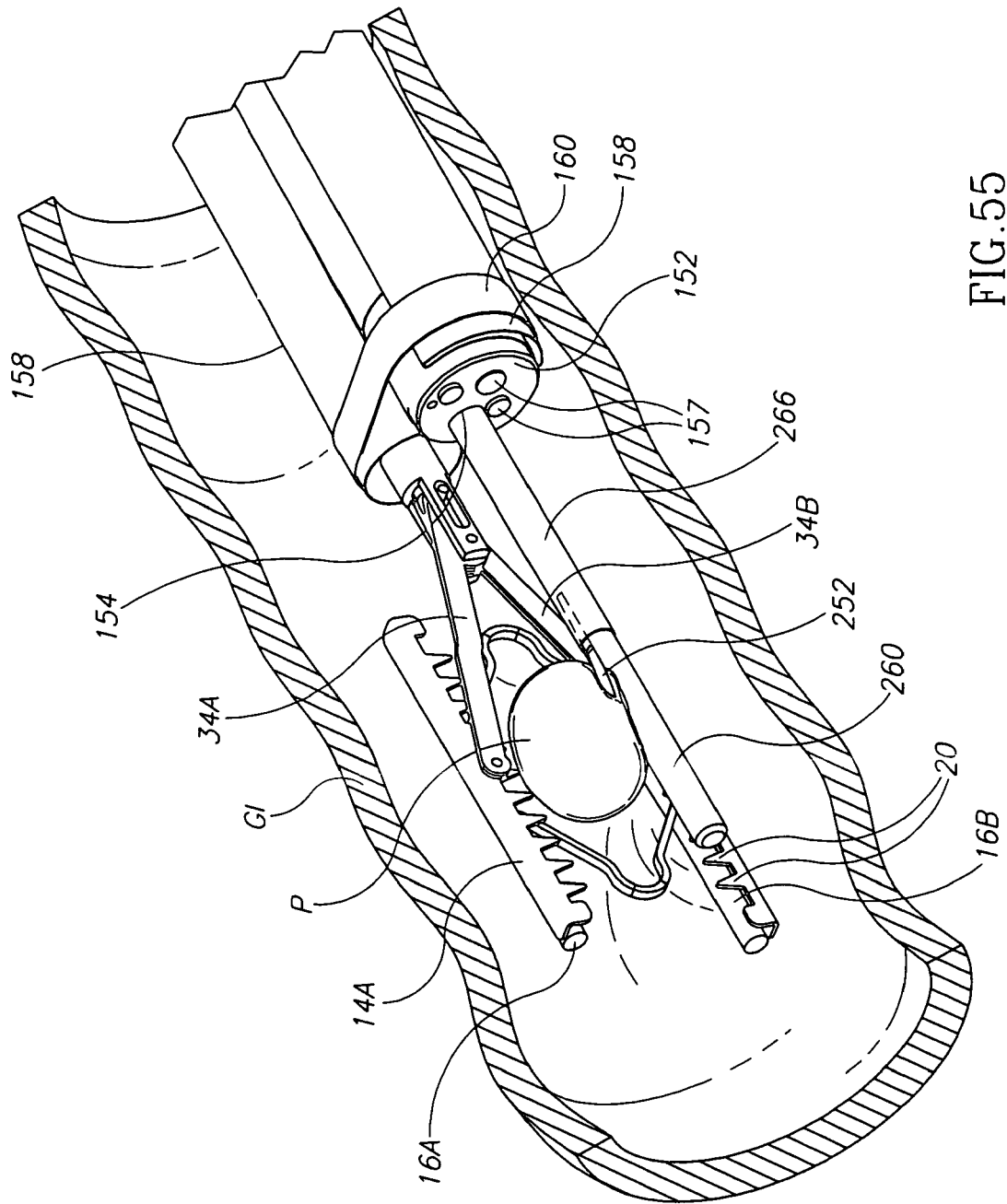
FIG. 55 shows a top side view of the grasper continuing to pull the polyp through the opened surgical clip.
Figure 56:
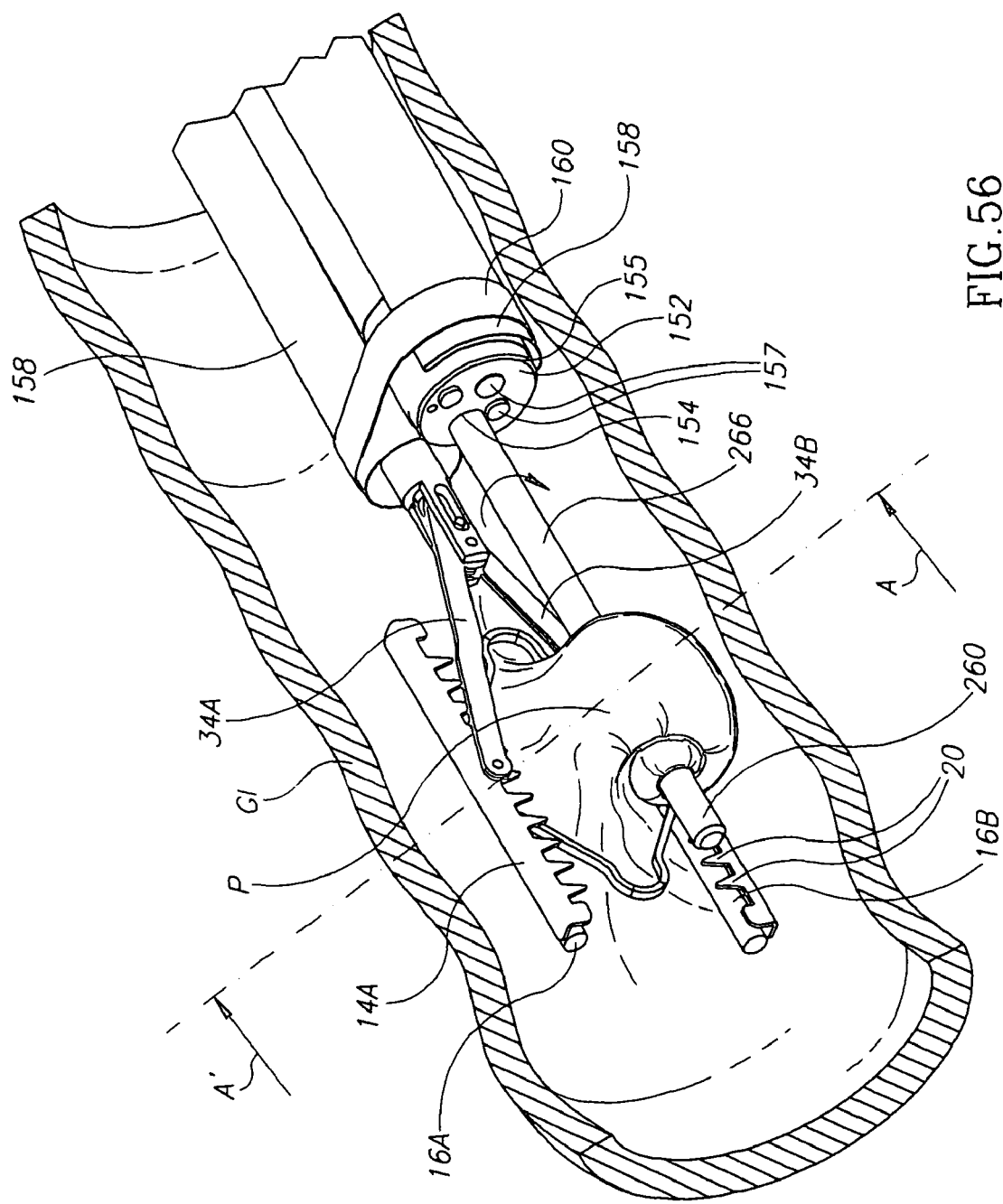
FIG. 56 shows a top side view of the grasper and grasper transporting element rotating and wrapping the pulled polyp around the grasper transporting element.
Figure 57:
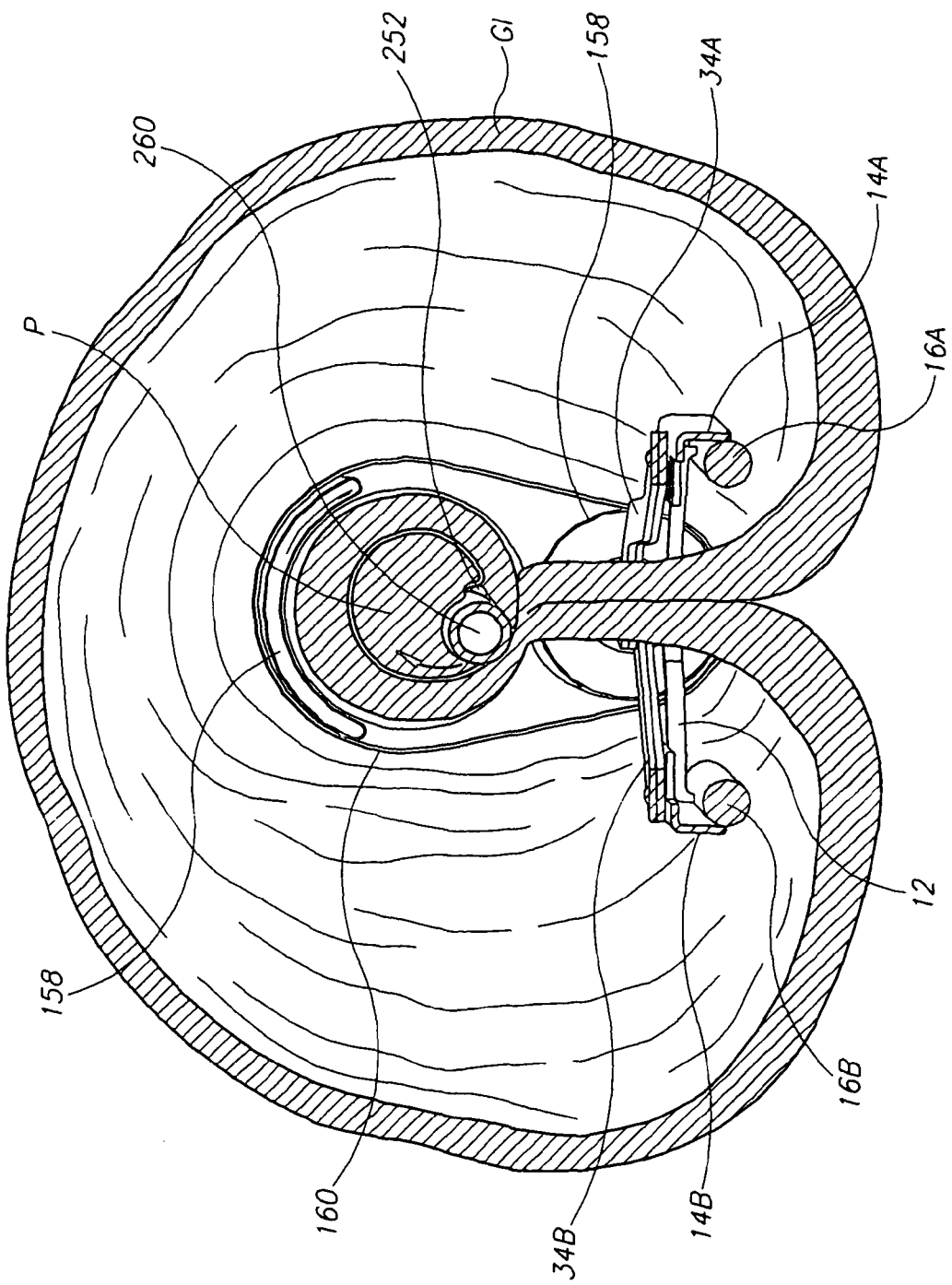
FIG. 57 shows a cross-sectional view along line AA' of FIG. 56 of the grasper and grasper transporting element rotating and wrapping the pulled polyp around the grasper transporting element.

Up to this point, the grasper (not shown) remains inside its grasper transporting element 260. Now the forceps arms 252 of the grasper are ejected from grasper transporting element 260 and positioned to grasp polyp P through the open clip (FIGS. 53 and 54).

Polyp P is then pulled by forceps arms 252 into the separated compressing and securing elements 16A, 16B and 14A, 14B, respectively, of open clip 10. This is shown in a top side view in FIG. 55. In this view, one of the forceps arms 252 of the grasper is barely visible; most of this arm and the entire second forceps arm are obscured by polyp P.

After, or simultaneously with, pulling polyp P, the polyp is rotated over and wrapped around grasper transporting element 260. This rotation is shown in an isometric view in FIG. 56 and a cross section view (FIG. 57) along line AA' of FIG. 56. Rotation is effected by the rotation of the entire grasper assembly, the grasper with forceps arms 252 holding the pulled polyp P, the grasper transporting element 260 and the assembly's shaft (not shown) using a control handle positioned outside the body cavity. Alternatively, rotating the control handle outside the body can be avoided by creating a swivel mechanism in the mechanical connection with the grasper assembly and rotating the swivel mechanism. Rotation ensures that sufficient tissue is being maneuvered into clip 10 and near severing device 310 (shown in FIG. 60) to allow for full transmural resection.

Figure 58:
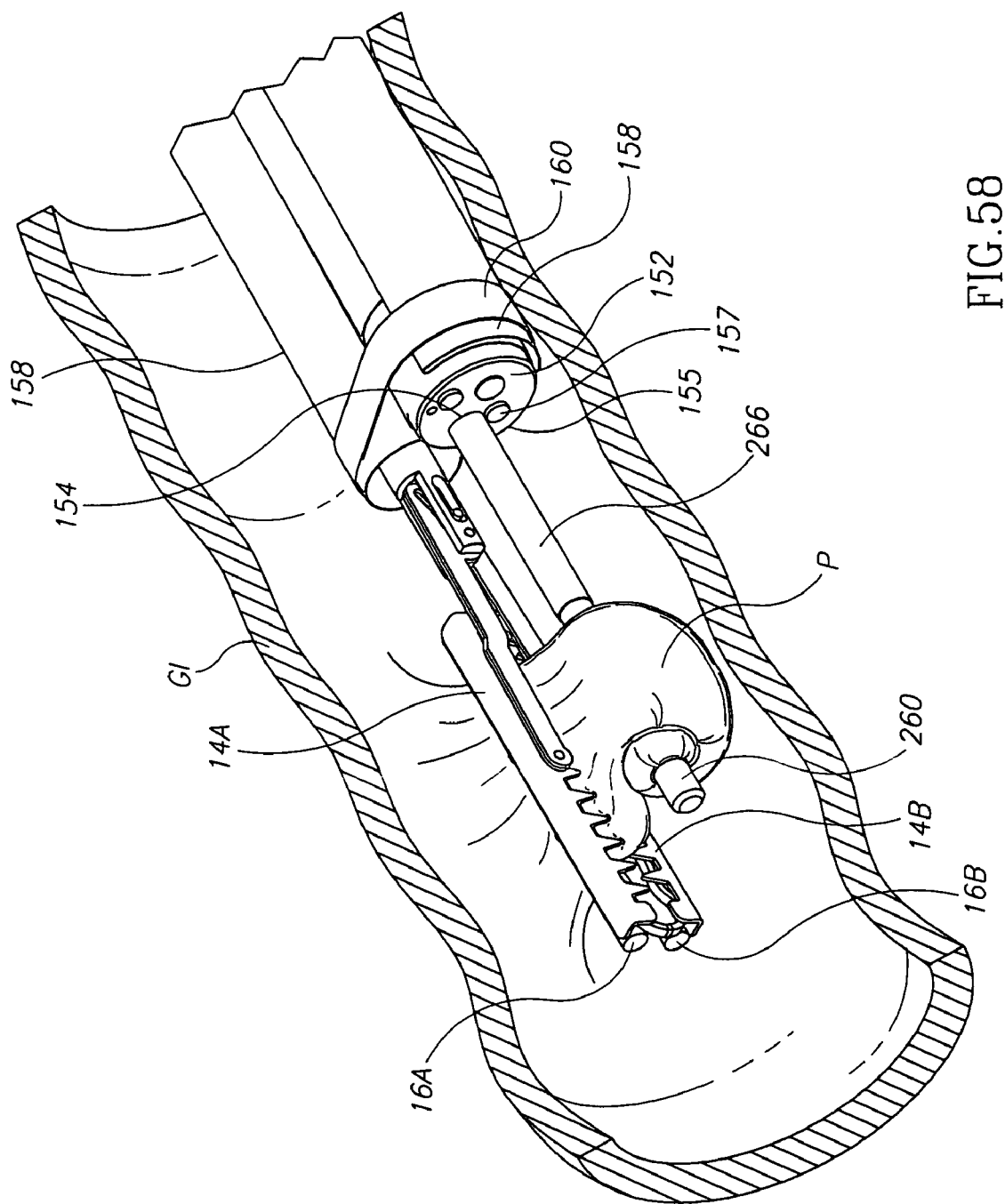
FIG. 58 shows a top side view of the surgical clip closing around the wrapped polyp.
Figure 59:
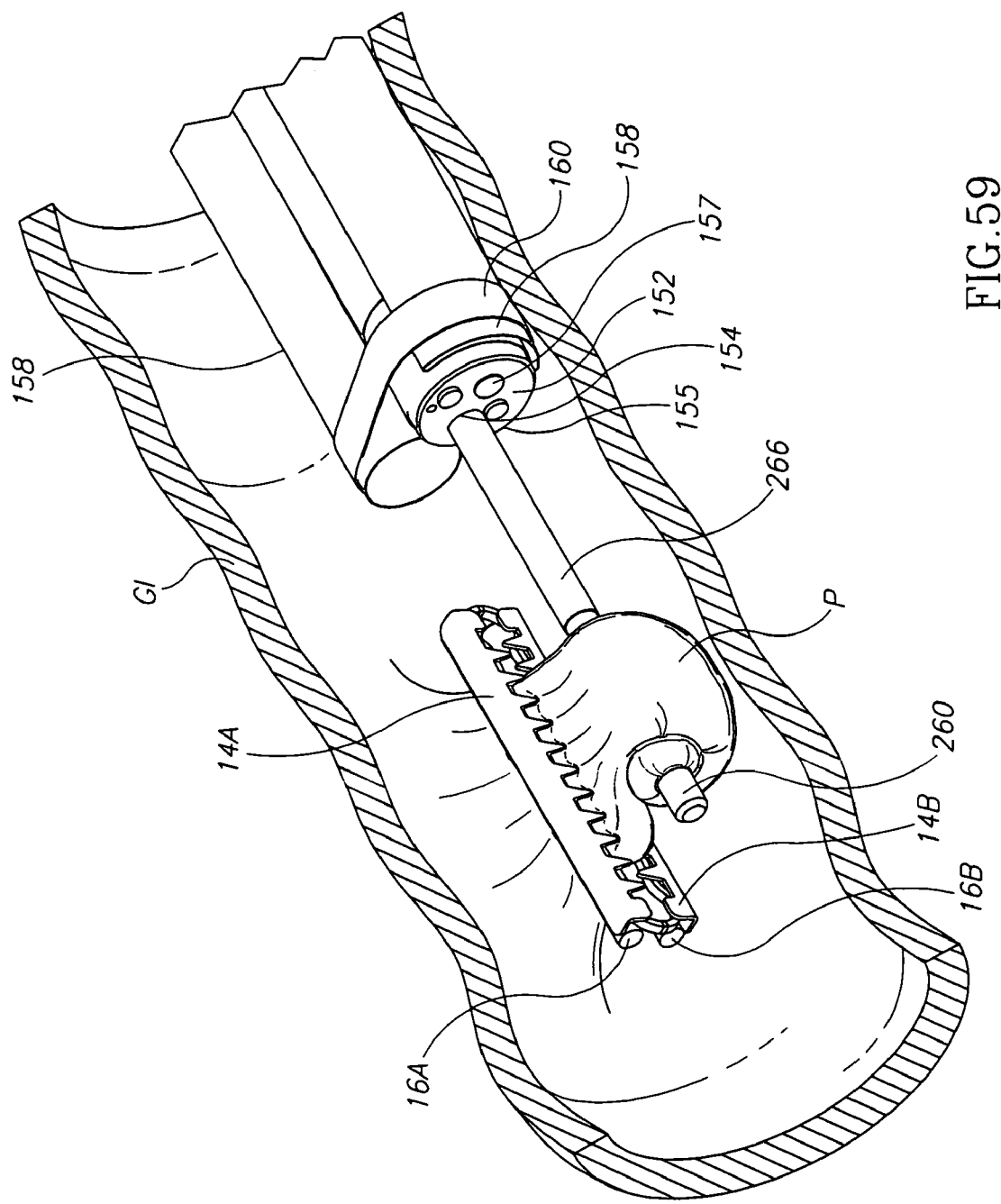
FIG. 59 shows a top side view of the closed surgical clip and polyp without the applier that has been withdrawn through a secondary lumen from the region of the resected polyp.

Clip applier 30 then closes clip 10 around the pulled and rotated polyp P (FIG. 58). Clip applier 30 is detached from the closed clip 10 and withdrawn via the secondary lumen 158 through which it entered (FIG. 59). Alternatively, if the physician feels it will assist him during the tissue resection, clip applier 30 could be detached from clip 10 after tissue resection.

Figure 60:
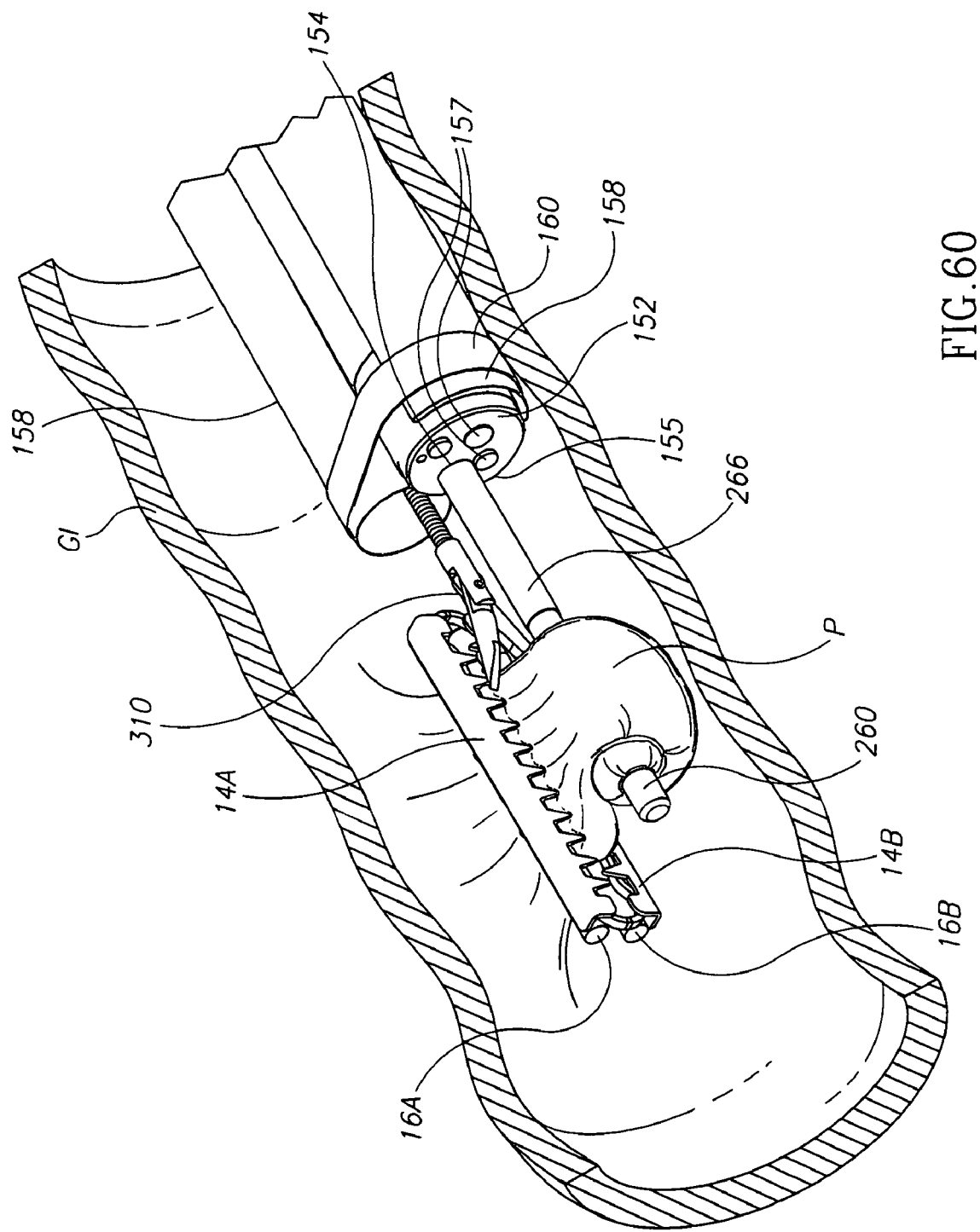
FIG. 60 shows a top side view of the closed surgical clip and polyp with a severing device approaching the rotated polyp for severing.

Polyp P wrapped around grasper transporting element 260 and compressed by clip 10 is severed by a severing device 310 shown being positioned close to polyp P (FIG. 60). Severing device 310 may be advanced to the polyp through the endoscope's working channel 154 or through a secondary lumen 158 of sleeve 150. In FIG. 60, severing device 310 has been advanced to its position for severing through the secondary lumen 158 used for advancing clip 10 and its applier 30. Severing device 310 approaches polyp P and severs it from the wall of the GI tract. The actual step of severing is not shown.

After severance of polyp P, the severed polyp held by the forceps arms of the grasper, together with the remainder of the grasper assembly, the severing device 310 and the endoscope shaft, are retracted in the direction of the proximal end of the endoscope and withdrawn from the body. Withdrawal directly from the body organ is a straight-forward step, and therefore this step of the method is not presented in a separate Figure. Polyp P can then be biopsied or treated as needed by a physician.

Figure 61:
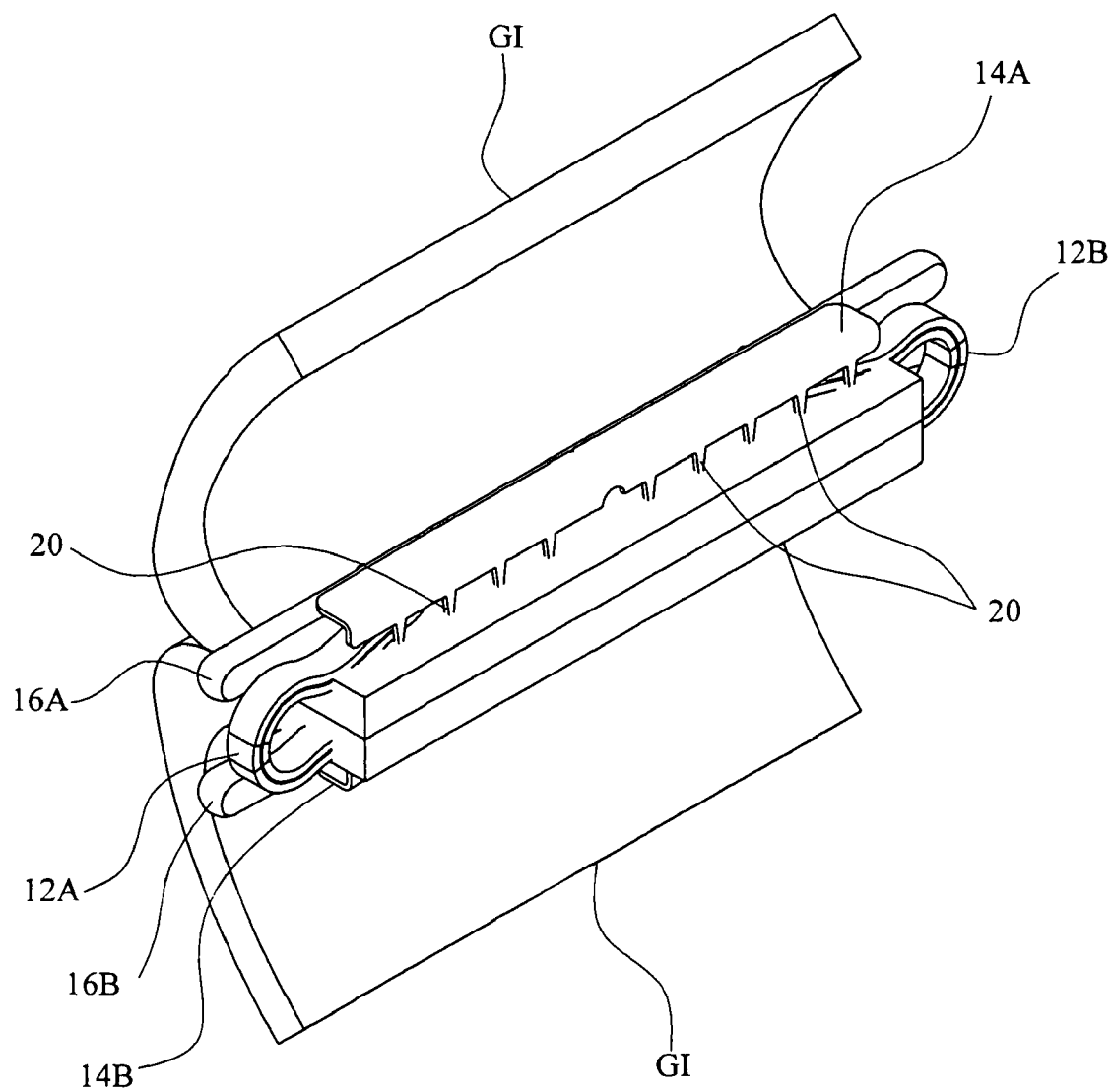
FIG. 61 shows a top side view of the tissue held by the clip at the resection site.
Figure 62A:
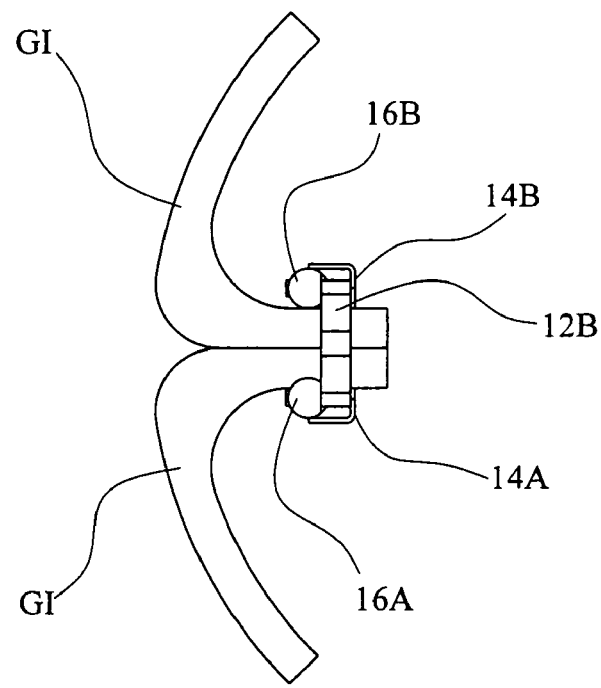
FIGS. 62A and 62B show two side views of the tissue held by the clip at the resection site.
Figure 62B:
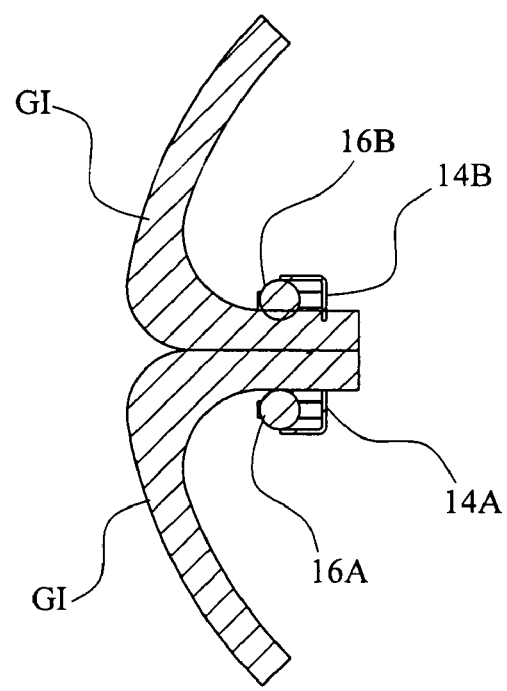

The closed surgical compression clip 10 remains around that portion of the GI wall from which the tissue was resected (FIGS. 61, 62A and 62B). Compression continues until necrosis is induced and healing of the resected site occurs. Clip 10 is naturally expelled from the body through the rectum or retrieved by the physician if needed.

The above described method may be operative when employing most of the clips designed according to embodiments of the present invention.

However, clip embodiment five discussed in conjunction with FIGS. 31A-44 requires some additional and/or modified steps. The element numbering below are those used in conjunction with FIGS. 31A-44 to which reference should be made.

The method for using the clip described in conjunction with FIGS. 31A-44 includes many of the same steps as those described above. However, the following additional or modified steps emphasize the novel aspects of the method associated with clip embodiment five. It does not include all of the steps required, many of which—including the step of rotation can be readily understood by reviewing the method described above.

Additional or modified steps when using clip embodiment five include:

Insertion of clip 70 in its closed position together with its applier 105;

Releasing the force exerted by applier 105 allowing hinge spring 86 to spread apart arms 72 and 74 of clip 70;

Pushing wire 90 forward and extending it to form a loop;

Placing the wire 90 loop over the polyp;

Pulling the polyp with a grasper through the loop created by the extended wire;

Positioning the arms 72 and 74 of clip 70 in their open position and bringing them around the side of the polyp rather than positioning the clip from the top of the polyp as with other clips discussed in the present invention;

Alternatively, the clip may be positioned in proximity to the polyp, after which the polyp is pulled between the open clip arms using a grasper;

Pulling wire 90 taut thereby preventing the polyp from escaping from between arms 72 and 74:

Closing arms 72 and 74 by continuing to pull wire 90 and/or using applier 105, and pulling cable 102 until latch 80 snaps over the second clip arm and latches therewith;

Detaching the anchor element 97 which anchors wire 90 to arm 74; and Pressing applier 105 slightly to release the applier.

The above step of pulling the polyp with a grasper is optional since in most situations wire 90 loop by itself can be maneuvered to encompass, grasp and pull the polyp or its stalk.

Positioning the clip from the side as discussed above is a result of the polyp being encompassed by wire 90 when the latter is in its extended position. When made taut, the wire effectively pulls the polyp from a lateral position into the waiting open arms 72 and 74 of clip 70.

Generally, insertion of closed clip 70 is effected through a secondary lumen of a multi lumen sleeve, but it also may be advanced through a working channel of the endoscope. The step of applying applier 105 occurs only after clip 70 has exited the secondary lumen or working channel.

It is readily understood by one skilled in the art that a full thickness resection with wide lateral areas (margins) is very difficult to achieve using conventional surgical approaches and employing conventional surgical instruments. This is particularly true of large polyps and especially large sessile polyps. Grasping and pulling a large section of a, generally slippery, polyp is very difficult especially given the limited space available in the body lumen for manipulation of the tissue. In order to overcome this difficulty, the step of rotating taught by the method of the present invention is useful. Additionally, a specially designed grasper assembly as described herein is used to effect and execute the step of rotating. Both the grasper assembly and step of rotating may be used to ensure that the entire polyp plus an adequate margin is resected.

In the above discussion of the present invention, the invention has been described as being used in bowel polyp resections. It should be evident to one skilled in the art that other types of lesions, in other organs in other organ systems, can also be resected using the present invention with little or no modification. Such organs include, but are not limited to, the urinary bladder and other organs of the urinary tract, the uterus, the liver, the esophagus, the gall bladder, the lungs and the rectum.

In the above discussion, the system and method of the present invention have been described as being used in endoscopic procedures which do not require a direct incision into the body cavity. The system and method as described herein above has been described as being inserted into the body cavity through one of the body's existing orifices. However, it is readily understood by those skilled in the art that the system and method described herein above can be used in open surgical procedures with little or no modification, where the point of entry of the system is an incision into the body cavity.

It should be readily apparent to one skilled in the art that the device and method of the present invention can be used to excise animal tissue as well as human tissue, particularly, but without being limiting, tissue of other mammalian species.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

It will be appreciated by persons skilled in the art that the present invention is not limited by the drawings and description hereinabove presented. Rather, the invention is defined solely by the claims that follow.

The invention claimed is:

1. A surgical clip assembly which comprises:

a pair of generally linear compression elements for securing tissue therebetween and for applying to the secured tissue a compression force, each compression element having a first end portion and a second end portion, wherein said clip assembly has an initial, open position in which said linear compression elements may be positioned about tissue to be secured therebetween, and a final, closed position whereat said compression elements are substantially parallel to each other, thereby to apply a compressive force to the secured tissue; and a first and a second hinge member, said first hinge member disposed between said first end portions of said pair of compression elements and said second hinge member disposed between said second end portions of said compression elements, said two hinge members being non-unitary with said pair of linear compression elements, wherein said first and second hinge members are in mechanical communication with said first and second end portions of said linear compression elements, respectively, and said hinge members are operative to transmit operational forces therebetween, and wherein said hinge members and compression elements form a closed bounded surface in both the open and closed positions of said clip assembly.

2. A surgical clip assembly according to claim 1, wherein said two hinge members are formed of a shape memory material.

3. A surgical clip assembly according to claim 2, further including a pair of generally linear securing elements, wherein each of said linear compression elements is associated with a different one of said pair of generally linear securing elements, said securing elements operative for securing tissue to be compressed by said compression elements and said securing elements forming a securing line when grasping said tissue, the securing line not collinear with the line of compressive force produced by said compression elements.

4. A surgical clip assembly according to claim 3, wherein each of said securing elements includes a gripping portion having a serrated profile formed of a plurality of teeth-like projections over at least part of the length of said securing elements.

5. A surgical clip assembly according to claim 4, wherein said teeth-like projections of said profile are not uniformly distributed along the length of said gripping portion.

6. A surgical clip assembly according to claim 3, further including at least one receiving structure sized and configured to disengageably receive an attachment element of a clip applier, the clip applier exerting a force counter to the force exerted by said two hinge members and operable for bringing the clip assembly from its closed position to its open position or vice versa.

7. A surgical clip assembly according to claim 3, wherein said pair of securing elements and said pair of compression elements are formed from material selected from the group of materials consisting of: an insulative material and an insulative-coated metal material.

8. A surgical clip assembly according to claim 3, wherein said compression elements and said securing elements are integrally formed with each other.

9. A surgical clip assembly according to claim 3, wherein said compression elements and said securing elements are joined by a method chosen from the group of methods consisting of: welding, gluing, a mechanical clip, fixating joint or a mechanical press.

10. A surgical clip assembly according to claim 2, wherein said first and second hinge members each has a generally planar body that includes two legs each having an end portion, and each of said hinge members has located at each of its end portions a connector having a single insertable end portion, said connector positioned substantially transversely to said planar body and said clip assembly further includes a pair of generally linear securing elements, wherein each of said linear compression elements is associated with a different one of said pair of generally linear securing elements, and wherein said single insertable end portion of said connectors is pivotably connected to said compression elements, thereby allowing concurrent mechanical communication between said hinge members and said compression elements.

11. A surgical clip assembly according to claim 2, wherein :said first and second hinge members each has a generally planar body that includes two legs each having an end portion, and each of said hinge members has located at each of its end portions a connector having a single insertable end portion, said connector positioned substantially transversely to said planar body and said clip assembly further includes a pair of generally linear securing elements, wherein each of said linear compression elements is associated with a different one of said pair of generally linear securing elements, and wherein said single insertable end portion of said connectors is pivotably connected to said securing elements, thereby allowing concurrent mechanical communication between said hinge members and said securing elements.

12. A surgical clip assembly according to claim 2, wherein said first and second hinge members each has a generally planar body that includes two legs each having an end portion, and each of said hinge members has located at each of its end portions a connector having first and second insertable end portions, said connector positioned substantially transversally to said planar body and said clip assembly further includes a pair of generally linear securing elements, wherein each of said linear compression elements is associated with one of said pair of generally linear securing elements, wherein said first end portions of said connectors of said hinge members is pivotably connected to said securing elements, thereby allowing concurrent mechanical communication between said hinge members and said two securing elements, and wherein said second insertable end portions of said connectors is pivotably connected to said compression elements, thereby allowing concurrent mechanical communication between said first and second hinge members and said two compression elements.

13. A surgical clip assembly according to claim 12, wherein said connectors of said first and second hinge members are joined to said legs of said hinge members on an inner surface of said legs, thereby to produce a preloaded clip assembly when said connectors are pivotably connected to at least one of said compression elements and at least one of said securing elements.

14. A surgical clip assembly according to claim 13, wherein said clip assembly further includes at least one gap forming element positioned on at least one end portion of at least one compression element, said gap forming element forming a gap between said compression elements when said clip assembly is in its closed position.

15. A surgical clip assembly according to any of claims 10-13, wherein said two legs of said first and second hinge members are each of the same length.

16. A surgical clip assembly according to any of claims 10-12, wherein said two hinge members are identical but said legs of said hinge members are of different lengths.

17. A surgical clip according to claim 16, wherein one of said compression elements has a hollow tubular structure with an elongated slot at each of its ends positioned on the side of said one of said compression elements proximate to said hinge members, wherein a projection translationally riding in each of said slots is pivotally connected to said hinge elements and said one of said compression elements, so that when said projections ride in said slots away from each other the longer of said legs of each of said hinge members travel in opposite directions from each other thereby causing said hinge members to bring said clip assembly to its open position and when said projections ride in said slots towards each other the longer of said legs of each of said hinge members travel toward each other thereby causing each of said hinge members to bring said clip assembly to its closed position.

18. A surgical clip assembly according to claim 17, wherein said clip assembly further includes two joined threaded bolts positioned inside said hollow compression element, each of said bolts having a different handedness and each having a threaded cylinder with an extension fitted thereon, each of said extensions being pivotably connected to a leg of a different one of said hinge members, said extensions operable as said projections for riding along the elongated slot when said threaded bolts are rotated, wherein when rotating said joined bolts in one direction, said projections, being in mechanical communication with said bolts, travel in said slots in a direction away from each other bringing said clip assembly to its open position and when rotating said joined bolts in a second direction said projections travel in said slots in a direction toward each other thereby bringing said clip assembly to its closed position.

19. A surgical clip assembly according to claim 17, wherein each of said hinge members has a connector positioned near the end portion of one of its legs, said connector operable as said projection for insertion into and translationally riding in said slots, said clip assembly further including wires connected to said connectors, wherein when said wires are pulled said connectors travel in said slots in a direction away from each other thereby bringing said clip assembly to its open position and when said wires are released, said connectors travel in said slots in a direction toward each other thereby bringing said clip assembly to its closed position.

20. A surgical clip assembly which comprises:

a pair of generally linear compression elements for securing tissue therebetween and for applying to the secured tissue a compression force, each compression element having a first end portion and a second end portion, wherein said clip assembly has an initial, open position in which said linear compression elements may be positioned about tissue to be secured therebetween, and a final, closed position whereat said compression elements are substantially parallel to each other, thereby to apply a compressive force to the secured tissue; and a first and a second hinge member, said first hinge member disposed between said first end portions of said pair of compression elements and said second hinge member disposed between said second end portions of said compression elements, wherein said first and second hinge members are in mechanical communication with said first and second end portions of said linear compression elements, respectively, and said hinge members are operative to transmit operational forces therebetween, and wherein said hinge members and compression elements form a closed bounded surface in both the open and closed positions of said clip assembly.

* * * * *